US008987226B2

(12) United States Patent
Koizumi et al.

(10) Patent No.: US 8,987,226 B2
(45) Date of Patent: Mar. 24, 2015

(54) MODIFIED SINGLE-STRANDED POLYNUCLEOTIDES

(75) Inventors: Makoto Koizumi, Tokyo (JP); Yasuhide Hirota, Tokyo (JP); Makiko Nakayama, Tokyo (JP); Mika Ikeda, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/991,209

(22) PCT Filed: Dec. 1, 2011

(86) PCT No.: PCT/JP2011/077758
§ 371 (c)(1),
(2), (4) Date: Jun. 3, 2013

(87) PCT Pub. No.: WO2012/074038
PCT Pub. Date: Jun. 7, 2012

(65) Prior Publication Data
US 2013/0253038 A1 Sep. 26, 2013

(30) Foreign Application Priority Data

Dec. 2, 2010 (JP) ................. 2010-269498
Apr. 27, 2011 (JP) ................. 2011-100159

(51) Int. Cl.
*C12N 15/113* (2010.01)
*A61K 31/7088* (2006.01)
*C12N 15/11* (2006.01)
*C07C 235/08* (2006.01)
*C07C 235/34* (2006.01)
*C07C 235/48* (2006.01)
*C07C 235/56* (2006.01)

(52) U.S. Cl.
CPC .......... *C12N 15/113* (2013.01); *A61K 31/7088* (2013.01); *C12N 15/111* (2013.01); *C07C 235/08* (2013.01); *C07C 235/34* (2013.01); *C07C 235/48* (2013.01); *C07C 235/56* (2013.01); *C12N 2310/531* (2013.01); *C12N 2320/51* (2013.01)
USPC ...................................................... 514/44 A

(58) Field of Classification Search
None
See application file for complete search history.

(56) References Cited

U.S. PATENT DOCUMENTS

2012/0220649 A1   8/2012   Koizumi et al.

FOREIGN PATENT DOCUMENTS

| WO | WO 02/08174 A1 | 1/2002 |
| WO | WO 2004/015075 A2 | 2/2004 |
| WO | WO 2005/019453 A2 | 3/2005 |
| WO | WO 2008/116094 A2 | 9/2008 |
| WO | WO 2010/001909 A1 | 1/2010 |
| WO | WO 2011/052715 A1 | 5/2011 |

OTHER PUBLICATIONS

Corse et al., "Biosynthesis of penicilins, V. substituted phenylacetic acid derivatives as penicilin precursors," *J. Am. Chem. Soc.*, (1948), 70(9): pp. 2837-2843.
Deng et al., "Synthesis and antidepressant-like action of N-(2-hydroxyethyl) cinnamamide derivatives in mice," *Med. Chem. Res.*, (2011), 20(8): pp. 1273-1279.
Gutierrez et al., "Antiplasmodial metabolites isolated from the marine octocoral *Muricea austera*," *J. Nat. Prod.*, (2006), 69(10): pp. 1379-1383.
Marzorati et al., "Incorporation of primary amines into a polyester chain by a combination of chemical and lipase-catalyzed ε-caprolactone ring-opening processes," *Adv. Synth. Catal.*, (2007), (2007), 349(11-12): pp. 1963-1968.
Xifeng et al., "Radical scavenging hydroxyphenyl ethanoic acid derivatives from a marine-derived fungus," *J. Microbiol. Biotechnol.*, (2006), 16(4): pp. 637-638.
International Search Report issued in PCT Application No. PCT/JP2011/077758, Feb. 16, 2012, 3 pages (English translation).
Chiu et al., "RNAi in Human Cells: Basic Structural and Functional Features of Small Interfering RNA," *Molecular Cell*, vol. 10, pp. 549-561 (2002).
Czauderna et al., "Structural variations and stabilizing modifications of synthetic siRNAs in mammalian cells," *Nucleic Acids Research*, vol. 31(11):2705-2716 (2003).
Elbashir et al., "Duplexes of 21-nucleotide RNAs mediate RNA interference in cultured mammalian cells," *Nature*, vol. 411, pp. 494-498 (2001).
Fire et al., "Potent and specific genetic interference by double-stranded RNA in *Caenorhabditis elegans*," *Nature*, vol. 391, pp. 806-811 (1998).
Hamilton et al., "A Species of Small Antisense RNA in Post-transcriptional Gene Silencing in Plants," *Science*, vol. 286, pp. 950-952 (1999).
Harborth et al., "Sequence, Chemical, and Structural Variation of Small Interfering RNAs and Short Hairpin RNAs and the Effect on Mammalian Gene Silencing," *Antisense and Nucleic Acid Drug Development*, vol. 13, pp. 83-105 (2003).
Nguyen et al., "Light controllable siRNAs regulate gene suppression and phenotypes in cells," *Biochimica et Biophysica Acta*, vol. 1758, pp. 394-403 (2006).
Nykanen et al., "ATP Requirements and Small Interfering RNA Structure in the RNA Interference Pathway," *Cell*, vol. 107, pp. 309-321 (2001).

(Continued)

*Primary Examiner* — Tracy Vivlemore
(74) *Attorney, Agent, or Firm* — Dorsey and Whitney LLP

(57) ABSTRACT

It is intended to provide a polynucleotide that is resistant to RNase and has an RNA interference effect, etc. The present invention provides a single-stranded polynucleotide that is derived from a double-stranded polynucleotide comprising a sense strand polynucleotide corresponding to a target gene, and an antisense strand polynucleotide having a nucleotide sequence complementary to the sense strand polynucleotide, and has a structure in which the 5'-end of the antisense strand and the 3'-end of the sense strand are linked via a phenyl group-containing linker to form a phosphodiester structure at each of these ends.

22 Claims, 18 Drawing Sheets

(56) References Cited

OTHER PUBLICATIONS

Parker et al., "Structural insights into mRNA recognition from a PIWI domain—siRNA guide complex," *Nature*, vol. 434, pp. 663-666 (2005).

Schwarz et al., "Evidence that siRNAs Function as Guides, Not Primers, in the *Drosophila* and Human RNAi Pathways," *Molecular Cell*, vol. 10, pp. 537-548 (2002).

Shah et al., "Tolerance of RNA Interference Toward Modifications of the 5' Antisense Phosphate of Small Interfering RNA," *Oligonucleotides*, vol. 17, pp. 35-43 (2007).

Tsui et al., "Stability of Endogenous and Added RNA in Blood Specimens, Serum, and Plasma," *Clinical Chemistry*, vol. 48, No. 10, pp. 1647-1653 (2002).

Weitzer et al., "The human RNA kinase hClp1 is active on 3' transfer RNA exons and short interfering RNAs," *Nature*, vol. 447, pp. 222-226 (2007).

PK-001  5' GCUCGUCUAUGACAAGUAAUU  SEQ ID NO: 15
PK-002    GUCGAGCAGAUACUGUUCAUU 5' SEQ ID NO: 16

PK-009  5' GCTCGUCUAUGACAAGTA     SEQ ID NO: 17
        3' UTCGAGCAGAUACTGTUCATU  SEQ ID NO: 18

US 8,987,226 B2

MODIFIED SINGLE-STRANDED POLYNUCLEOTIDES

This application is a national stage application under 35 U.S.C. §371 of International Application No. PCT/JP2011/077758, filed Dec. 1, 2011, entitled "Modified Single-Stranded Polynucleotide," which claims priority to Japanese Patent Application No. 2010-269498, filed Dec. 2, 2010, and to Japanese Patent Application No. 2011-100159, filed Apr. 27, 2011, the contents of all of which are hereby incorporated in their entirety by reference.

TECHNICAL FIELD

The present invention relates to a single-stranded polynucleotide that has an RNA interference effect and/or a gene expression inhibitory effect, use of the polynucleotide, a method for inhibiting gene expression using the polynucleotide, a pharmaceutical composition comprising the polynucleotide, etc.

BACKGROUND ART

Methods for inhibiting the expression of a target gene in cells, tissues, or individuals include an approach in which double-stranded RNA is introduced into the cells, tissues, or individuals. By this introduction of double-stranded RNA, mRNA having homology to the sequence is degraded such that the expression of the target gene is inhibited. This effect is called "RNA interference" or "RNAi". RNA interference was originally reported in *C. elegans* (see e.g., Non Patent Reference 1) and then also reported in plants (see e.g., Non Patent Reference 2).

Double-stranded RNA consisting of 21-nucleotide sense and antisense strands having a 2-nucleotide overhang at the 3'-end (small interfering RNA: siRNA) has been reported to have an RNA interference effect in cultured cells of vertebrates (see e.g., Non Patent Reference 3). siRNA is considered to be useful for the identification of gene functions, screening of cell strains suitable for useful substance production, regulation of genes involved in disease, etc., but, however, it is characteristically degraded easily by RNase (see e.g., Non Patent Reference 4).

A double-stranded polynucleotide having nucleotide units of alternately combined DNAs and 2'-OMeRNAs, instead of RNAs constituting siRNA, has been reported as being a double-stranded polynucleotide that is resistant to RNase and has an RNA interference effect (see Patent Reference 1).

Some reports have been made on the modification of the 5'-ends of sense and antisense strands in siRNA. It has been reported that siRNA having a 6-aminohexyl phosphate group at the 5'-end of the sense or antisense strand has inhibitory activity against the expression of target mRNA (see Non Patent Reference 5). On the other hand, it has been reported that siRNA having this 6-aminohexyl phosphate group at the 5'-end of the antisense strand has no inhibitory activity against the expression of target mRNA (see e.g., Non Patent Reference 6). It has also been reported that siRNA having a 3-aminopropyl phosphate group at the 5'-end of the sense strand has inhibitory activity against the expression of target mRNA, whereas siRNA having a 3-aminopropyl phosphate group at the 5'-end of the antisense strand has no inhibitory activity against the expression of target mRNA (see e.g., Non Patent Reference 7). It has been reported that inhibitory activity against the expression of target mRNA is observably lower in siRNA having the 6-aminohexyl phosphate group or the 3-aminopropyl phosphate group at the 5'-end of the antisense strand than in unmodified siRNA but it is not completely lost. (see e.g., Non Patent Reference 8).

It has been reported that siRNA having fluorescein at the 5'-end of the sense or antisense strand also has inhibitory activity against the expression of target mRNA (see e.g., Non Patent Reference 9). It has been reported that of siRNAs having a steroid or lipid structure at the 5'-end of the sense or antisense strand, siRNA having a steroid or lipid structure at the 5'-end of the sense strand has inhibitory activity against the expression of target mRNA (see e.g., Non Patent Reference 8). It has been reported that when siRNA has an ortho-nitrobenzyl derivative, which can be eliminated by UV irradiation, at the 5'-end of the antisense strand, its inhibitory activity against the expression of target mRNA can be controlled by using UV irradiation (see e.g., Non Patent Reference 10).

siRNA in which the 3'-end of the sense strand and the 5'-end of the antisense strand are linked via a loop consisting of approximately 4 nucleotide units forms a single-stranded polynucleotide called short hairpin RNA (shRNA). shRNA having a 19-bp stem moiety has been shown to have lower activity than that of a 19-bp siRNA having the same nucleotide sequence thereas (see e.g., Non Patent Reference 9). Although shRNA comprising a 19-bp stem and a loop having two nucleotides replaced with a non-nucleotide linker such as propyl phosphate units was synthesized and examined for its inhibitory activity against the expression of target mRNA, no improvement in activity was observed, compared with unmodified shRNA (see e.g., Non Patent Reference 9). An example using an ortho-nitrobenzyl derivative has been reported as siRNA in which the 3'-end of the sense strand and the 5'-end of the antisense strand are linked via a non-nucleotide linker (see e.g., Non Patent Reference 8). This 19-bp siRNA whose sense and antisense strands are linked via the ortho-nitrobenzyl derivative has lower inhibitory activity against the expression of target mRNA than that of unmodified siRNA. In addition, cultured cells transfected with this siRNA were irradiated with UV for 10 minutes and examined for the inhibitory activity of the siRNA against the expression of target mRNA. As a result, the inhibitory activity against the expression of target mRNA was lower than that of unmodified siRNA. A single-stranded polynucleotide having a structure in which the 5'-end of the antisense strand and the 3'-end of the sense strand are linked via a phenyl group-containing linker to form a phosphodiester structure at each of these ends is not yet known.

X-ray analysis of a complex of an antisense strand with Argonaute protein (Ago) known to participate in RNAi activity has showed that the 5'-terminal phosphate group of the antisense strand and its neighboring nucleotides are strongly bound to the PIWI domain of Ago (see e.g., Non Patent Reference 11). It has been reported that upon introduction of chemically synthesized siRNA into cells, both sense and antisense strands are 5'-terminally phosphorylated (see e.g., Non Patent Reference 12). In human cells, RNA kinase hC1p1 has been reported to be responsible for the 5'-phosphorylation of siRNA (see e.g., Non Patent Reference 13). When 5'-terminally phosphorylated siRNA and siRNA having an unphosphorylated 5'-end were separately introduced into cells and their RNAi activities were compared, no difference in activity was seen therebetween, indicating that the siRNA having an unphosphorylated 5'-end is easily subject to phosphorylation in cells (see e.g., Non Patent Reference 9).

In the case of using the shRNA in which the 3'-end of the sense strand and the 5'-end of the antisense strand are linked via a loop, this shRNA is intracellularly cleaved by the Dicer protein or an endonuclease to form an antisense strand having a 5'-terminal phosphate group (see e.g., Non Patent Reference 9). The shRNA comprising a 19-bp stem and a loop having two nucleotides replaced with propyl phosphate units cannot be expected to undergo intracellular Dicer or endonuclease cleavage, because the propyl phosphate units are resistant to nuclease (see e.g., Non Patent Reference 9). Alternatively, the shRNA comprising a 19-bp stem and an ortho-nitrobenzyl derivative loop can be expected to form an antisense strand having a 5'-terminal phosphate group by UV irradiation. Such UV irradiation, however, is difficult to apply to living bodies due to possible adverse reactions and due to the difficulty of applying UV irradiation inside a living body (see e.g., Non Patent Reference 8). A single-stranded polynucleotide comprising a 19-bp or less stem and a loop having a non-nucleotide linker alone, which is intracellularly cleaved by Dicer or endonuclease without UV irradiation to form an antisense strand having a 5'-terminal phosphate group, is not yet known.

The present inventors have conducted diligent studies to obtain a polynucleotide that has an RNA interference effect and/or a gene expression inhibitory effect, and have consequently completed the present invention by finding a single-stranded polynucleotide having an RNA interference effect and/or a gene expression inhibitory effect, which is derived from a double-stranded polynucleotide comprising a sense strand polynucleotide corresponding to a target gene, and an antisense strand polynucleotide having a nucleotide sequence complementary to the sense strand polynucleotide, and has a structure in which the 5'-end of the antisense strand and the 3'-end of the sense strand are linked via a phenyl group-containing linker to form a phosphodiester structure at each of these ends.

REFERENCE

Patent Reference

Patent Reference 1: International Publication No. WO 2010/001909.

Non Patent Reference

Non Patent Reference 1: Nature, 1998, Vol. 391, p. 806-811.
Non Patent Reference 2: Science, 1999, Vol. 286, p. 950-952.
Non Patent Reference 3: Nature, 2001, Vol. 411, p. 494-498.
Non Patent Reference 4: Clinical Chemistry, 2002, Vol. 48, p. 1647-1653.
Non Patent Reference 5: Molecular Cell, 2002, Vol. 10, p. 537-548.
Non Patent Reference 6: Nucleic Acids Research, 2003, Vol. 31, p. 2705-2716.
Non Patent Reference 7: Molecular Cell, 2002, Vol. 10, p. 549-561.
Non Patent Reference 8: Oligonucleotides, 2007, Vol. 17, p. 35-43.
Non Patent Reference 9: Antisense Nucleic Acid Drug Development, 2003, Vol. 13, p. 83-105.
Non Patent Reference 10: Biochimica Biophysica Acta, 2006, Vol. 1758, p. 394-403.
Non Patent Reference 11: Nature, 2005, Vol. 434, p. 663-666.
Non Patent Reference 12: Cell, 2001, Vol. 107, p. 309-321.
Non Patent Reference 13: Nature, 2007, Vol. 447, p. 222-226.

SUMMARY OF THE INVENTION

Problems to be Solved by the Invention

An object of the present invention is to provide a polynucleotide that has an RNA interference effect and/or a gene expression inhibitory effect.

A further object of the present invention is to provide a polynucleotide that is resistant to RNase and has an RNA interference effect and/or a gene expression inhibitory effect.

A further object of the present invention is to provide a method for inhibiting gene expression using the polynucleotide.

A further object of the present invention is to provide a pharmaceutical composition comprising the polynucleotide.

Means for Solving the Problems

Specifically, the present invention consists of:
(1) A polynucleotide or a salt thereof, the polynucleotide comprising a sense strand polynucleotide corresponding to a target gene, and an antisense strand polynucleotide having a nucleotide sequence complementary to the sense strand polynucleotide, wherein the 5'-end of the antisense strand polynucleotide and the 3'-end of the sense strand polynucleotide are linked via a linker to form a phosphodiester structure at each of these ends, the linker having a structure represented by the following formula:

[Formula 1]

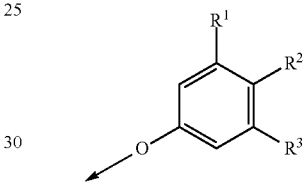

wherein
the oxygen atom bonded to the phenyl group is bound to the 5'-end of the antisense strand to form a phosphodiester structure;
any one of $R^1$, $R^2$, and $R^3$ represents a structure represented by the following formula:

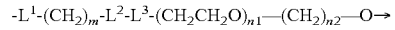

wherein
m represents an integer of 0 to 4,
n1 represents an integer of 0 to 4,
n2 represents 0 or an integer of 2 to 10,
$L^1$ represents a single bond or —O—,
$L^2$ represents a single bond or —CH(—NH-$L^4$-R)—,
$L^3$ represents a single bond, —(C=O)—NH—, or —NH—(C=O)— starting from the bond with $L^2$,
provided that if $L^3$ is not a single bond, then n2 represents an integer of 2 to 10,
provided that if each of $L^1$ and $L^2$ is a single bond, m is 1, and each of n1 and n2 is 0, then $L^3$-O→ represents
—CH(COOH)NH-(amino acid residue)$_j$-Ser,
—CH(COOH)NH-(amino acid residue)$_j$-Thr,
—CH(NH$_2$)CO-(amino acid residue)$_j$-Ser, or
—CH(NH$_2$)CO-(amino acid residue)$_j$-Thr, wherein
the hydroxy group moiety of this serine or threonine is bound to the 3'-terminal phosphate group of the sense strand polynucleotide, and the amino group of this serine or threonine may be further substituted by an acyl group,
j represents an integer of 0 to 2,
$L^4$ represents a single bond, —(C=O)—(CH$_2$)$_k$—NH—, or —(C=O)—(CH$_2$)$_k$—,
k represents an integer of 1 to 6, and
R represents a hydrogen atom, an alkyl group having 1 to 6 carbon atoms, a saturated or unsaturated hydrocarbon-carbonyl group having 2 to 30 carbon atoms, or a saturated or unsaturated hydrocarbon-oxycarbonyl group having 2 to 30 carbon atoms; and the remaining two of $R^1$, $R^2$, and $R^3$ each independently represent a group selected from the group consisting of
a hydrogen atom,
an alkyl group having 1 to 8 carbon atoms which may have a substituent,
an alkoxy group having 1 to 8 carbon atoms which may have a substituent,
a halogen atom,
an alkylcarbonylamino group having an alkyl group having 1 to 9 carbon atoms, and
an alkylcarbonyl group containing an alkyl group having 1 to 8 carbon atoms which may have a substituent;

(2) The polynucleotide or a salt thereof according to (1), wherein each of $R^1$ and $R^3$ is a hydrogen atom;

(3) The polynucleotide or a salt thereof according to (2), wherein each of $L^1$ and $L^2$ is a single bond, $L^3$ is —(C=O)—NH—, and the sum of m and n2 is an integer of 3 or larger;

(4) The polynucleotide or a salt thereof according to (2), wherein each of $L^1$ and $L^2$ is a single bond, $L^3$ is —(C=O)—NH—, and the sum of m and n2 is an integer of 8 or larger;

(5) The polynucleotide or a salt thereof according to (2), wherein each of $L^1$ and $L^2$ is a single bond, $L^3$ is —(C=O)—NH—, m is 0 or 2, and n2 is an integer of 6 or larger;

(6) The polynucleotide or a salt thereof according to (2), wherein each of $L^1$ and $L^2$ is a single bond, $L^3$ is —(C=O)—NH—, m is 0 or 2, and n2 is 6 or 8;

(7) The polynucleotide or a salt thereof according to (2), wherein each of $L^1$ and $L^2$ is a single bond, $L^3$ is —(C=O)—NH—, m is 0 or 2, and n2 is 8;

(8) The polynucleotide or a salt thereof according to (1), wherein each of $R^1$ and $R^3$ is a hydrogen atom, each of $L^1$ and $L^2$ is a single bond, $L^3$ is —(C=O)—NH—, m is 2, and n2 is 8;

(9) A polynucleotide or a salt thereof, the polynucleotide comprising a sense strand polynucleotide corresponding to a target gene, and an antisense strand polynucleotide having a nucleotide sequence complementary to the sense strand polynucleotide and having a structure represented by the following formula, wherein the 5'-end of the antisense strand polynucleotide and the 3'-end of the sense strand polynucleotide are linked via a linker through phosphodiester bonds:

[Formula 2]

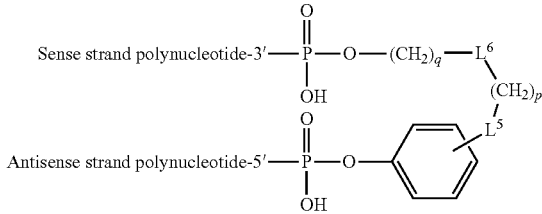

wherein
p represents an integer of 0 to 4,
q represents an integer of 4 to 10,
$L^5$ represents a single bond or —O—,
$L^6$ represents —(C=O)—NH— or —NH—(C=O)— starting from the bond with $(CH_2)_p$,
$L^5$ is bonded to the benzene ring at the para or meta position, and
provided that if $L^5$ is —O—, then p represents an integer of 1 to 4;

(10) The polynucleotide or a salt thereof according to (9), wherein the sum of p and q is an integer of 4 or larger, $L^5$ is a single bond, $L^6$ is —(C=O)—NH—, and $L^5$ is bonded to the benzene ring at the para position;

(11) The polynucleotide or a salt thereof according to (9), wherein the sum of p and q is an integer of 8 or larger, $L^5$ is a single bond, $L^6$ is —(C=O)—NH—, and $L^5$ is bonded to the benzene ring at the para position;

(12) The polynucleotide or a salt thereof according to (9), wherein p is 0 or 2, q is an integer of 6 or larger, $L^5$ is a single bond, $L^6$ is —(C=O)—NH—, and $L^5$ is bonded to the benzene ring at the para position;

(13) The polynucleotide or a salt thereof according to (9), wherein p is 0 or 2, q is 6 or 8, $L^5$ is a single bond, $L^6$ is —(C=O)—NH—, and $L^5$ is bonded to the benzene ring at the para position;

(14) The polynucleotide or a salt thereof according to (9), wherein p is 0 or 2, q is 8, $L^5$ is a single bond, $L^6$ is —(C=O)—NH—, and $L^5$ is bonded to the benzene ring at the para position;

(15) The polynucleotide or a salt thereof according to (9), wherein p is 2, q is 8, $L^5$ is a single bond, $L^6$ is —(C=O)—NH—, and $L^5$ is bonded to the benzene ring at the para position;

(16) The polynucleotide or a salt thereof according to (1) to (15), wherein the sense strand polynucleotide consists of a polynucleotide represented by the following formula (II), the antisense strand polynucleotide consists of a polynucleotide represented by the following formula (III), and the polynucleotide further has the following features (a) to (d):

$$5'\text{-}(\gamma\text{-}\beta)_9\text{-}\gamma\text{-}\lambda_t\text{-}3' \quad \text{(II) and}$$

$$5'\text{-}\beta\text{-}(\gamma\text{-}\beta)_9\text{-}\nu_u\text{-}3' \quad \text{(III),}$$

(a) γ represents an RNA, β represents a 2'-OMeRNA, and λ and ν each represent a DNA;

(b) t and u identically or differently represent any integer from 0 to 5;

(c) $(\gamma\text{-}\beta)_9\text{-}\gamma$ in the polynucleotide represented by the formula (II) has a nucleotide sequence identical to the target gene; and (d) $(\gamma\text{-}\beta)_9\text{-}\gamma$ in the formula (II) and $\beta\text{-}(\gamma\text{-}\beta)_9$ in the formula (III) have nucleotide sequences complementary to each other;

(17) The polynucleotide or a salt thereof according to (1) to (15), wherein the sense strand polynucleotide consists of a polynucleotide represented by the following formula (IV), the antisense strand polynucleotide consists of a polynucleotide represented by the following formula (V), and the polynucleotide further has the following features (a) to (d):

$$5'\text{-}(\alpha\text{-}\beta)_9\text{-}\alpha_p\text{-}\lambda_t\text{-}3' \quad \text{(IV) and}$$

$$5'\text{-}\delta_s\text{-}(\alpha\text{-}\beta)_9\text{-}\nu_u\text{-}3' \quad \text{(V),}$$

(a) α and β differently represent a DNA or a 2'-OMeRNA, δ and λ identically or differently represent a DNA or a 2'-OMeRNA, and ν identically or differently represents any nucleotide selected from a DNA, an RNA, and a 2'-OMeRNA;

(b) p represents an integer of 0 or 1, t is 0 when p is 0 and represents any integer from 0 to 5 when p is 1, s represents an integer of 0 or 1, and u represents any integer from 0 to 5;

(c) $(\alpha\text{-}\beta)_9\text{-}\alpha_p$ in the polynucleotide represented by the formula (IV) has a nucleotide sequence identical to the target gene; and (d) $(\alpha\text{-}\beta)_9$ in the formula (IV) and $(\alpha\text{-}\beta)_9$ in the formula (V) have nucleotide sequences complementary to each other;

(18) The polynucleotide or a salt thereof according to (1) to (15), wherein the sense strand polynucleotide consists of a polynucleotide represented by the following formula (VI), the antisense strand polynucleotide consists of a polynucleotide represented by the following formula (VII), and the polynucleotide further has the following features (a) to (d):

   (VI) and

   (VII), (a) α and β differently represent a DNA or a 2'-OMeRNA, δ and λ identically or differently represent a DNA or a 2'-OMeRNA, and ν identically or differently represents any nucleotide selected from a DNA, an RNA, and a 2'-OMeRNA;

(b) p represents an integer of 0 or 1, t is 0 when p is 0 and represents any integer from 0 to 5 when p is 1, s represents an integer of 0 or 1, and u represents any integer from 0 to 5;

(c) β-(α-β)$_8$-αp in the polynucleotide represented by the formula (VI) has a nucleotide sequence identical to the target gene; and (d) (α-β)$_8$ in the formula (VI) and (α-β)$_8$ in the formula (VII) have nucleotide sequences complementary to each other;

(19) The polynucleotide or a salt thereof according to (17) or (18), wherein α is a DNA, and β is a 2'-OMeRNA;

(20) The polynucleotide or a salt thereof according to any one of (16) to (19), wherein $\lambda_t$ and $\nu_u$ are identically or differently any of: DNAs having a thymine base, an adenine base, or a guanine base; or 2'-OMeRNAs having a uracil base, an adenine base, or a guanine base;

(21) The polynucleotide or a salt thereof according to any one of (16) to (20), wherein t is 0, and u is 2;

(22) The polynucleotide or a salt thereof according to any one of (17) to (20), wherein p and t are 0, s is 1, and u is 2;

(23) The polynucleotide or a salt thereof according to (17) to (20), wherein p and t are 0, s is 0 or 1, u is 2, and $\nu_2$ is a DNA or a 2'-OMeRNA;

(24) The polynucleotide or a salt thereof according to any one of (1) to (15), wherein the sense strand polynucleotide consists of a polynucleotide represented by the following formula (VIII), the antisense strand polynucleotide consists of a polynucleotide represented by the following formula (IX), and the polynucleotide further has the following features (a) to (c):

   (VIII) and

   (IX), (a) α is a DNA, and β is a 2'-OMeRNA;

(b) β-(α-β)$_9$ in the polynucleotide represented by the formula (IX) has a nucleotide sequence complementary to the target gene; and (c) (α-β)$_9$ in the formula (VIII) and (α-β)$_9$ in the formula (IX) have nucleotide sequences complementary to each other;

(25) The polynucleotide or a salt thereof according to any one of (16) to (24), wherein any or all of 1 to 4 2'-OMeRNA residues are substituted by an ENA or a 2',4'-BNA/LNA;

(26) The polynucleotide or a salt thereof according to any one of (16) to (25), wherein any or all of 1 to 4 DNA residues are substituted by an RNA, an ENA or a 2',4'-BNA/LNA;

(27) The polynucleotide or a salt thereof according to any one of (1) to (26), wherein the nucleotides are bonded to each other via a phosphodiester or phosphorothioate bond;

(28) A pharmaceutical composition comprising a polynucleotide or a salt thereof according to any one of (1) to (27) as an active ingredient.

(29) The pharmaceutical composition according to (28), wherein the pharmaceutical composition is for the treatment of a disease derived from gene expression;

(30) A method for inhibiting the expression of a target gene, comprising administering a polynucleotide or a salt thereof selected from (1) to (27) to a mammal;

(31) A reagent comprising a polynucleotide or a salt thereof according to any one of (1) to (27);

(32) A compound represented by the formula (X) or a salt thereof:

[Formula 3]

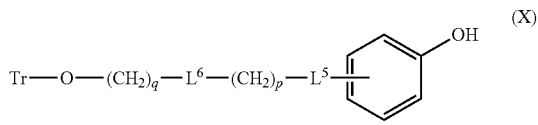   (X)

wherein Tr represents a protective group for the hydroxy group; p represents an integer of 0 to 4; q represents an integer of 4 to 10; $L^5$ represents a single bond or —O—; $L^6$ represents —(C=O)—NH— or —NH—(C=O)— starting from the bond with (CH$_2$)$_p$; and $L^5$ is bonded to the benzene ring at the para or meta position;

(33) The compound or a salt thereof according to (32), wherein Tr is a 4-methoxytrityl group, a 4,4'-dimethoxytrityl group, a pixyl group, a trityl group, a levulinyl group, or a bis(trimethylsilyloxy)(cyclohexyloxy)silyl group;

(34) The compound or a salt thereof according to (32), wherein Tr is a 4-methoxytrityl group or a 4,4'-dimethoxytrityl group, the sum of p and q is an integer of 4 or larger, $L^5$ is a single bond, $L^6$ is —(C=O)—NH—, and $L^5$ is bonded to the benzene ring at the para position;

(35) The compound or a salt thereof according to (32), wherein Tr is a 4-methoxytrityl group or a 4,4'-dimethoxytrityl group, the sum of p and q is an integer of 8 or larger, $L^5$ is a single bond, $L^6$ is —(C=O)—NH—, and $L^5$ is bonded to the benzene ring at the para position;

(36) The compound or a salt thereof according to (32), wherein Tr is a 4-methoxytrityl group or a 4,4'-dimethoxytrityl group, p is 0 or 2, q is an integer of 6 or larger, $L^5$ is a single bond, $L^6$ is —(C=O)—NH—, and $L^5$ is bonded to the benzene ring at the para position;

(37) The compound or a salt thereof according to (32), wherein Tr is a 4-methoxytrityl group or a 4,4'-dimethoxytrityl group, p is 0 or 2, q is 6 or 8, $L^5$ is a single bond, $L^6$ is —(C=O)—NH—, and $L^5$ is bonded to the benzene ring at the para position;

(38) The compound or a salt thereof according to (32), wherein Tr is a 4-methoxytrityl group or a 4,4'-dimethoxytrityl group, p is 0 or 2, q is 8, $L^5$ is a single bond, $L^6$ is —(C=O)—NH—, and $L^5$ is bonded to the benzene ring at the para position;

(39) The compound or a salt thereof according to (32), wherein Tr is a 4-methoxytrityl group or a 4,4'-dimethoxytrityl group, p is 2, q is 8, $L^5$ is a single bond, $L^6$ is —(C=O)—NH—, and $L^5$ is bonded to the benzene ring at the para position;

(40) The compound or a salt thereof according to (32), wherein Tr is a 4,4'-dimethoxytrityl group, p is 2, q is 8, $L^5$ is a single bond, $L^6$ is —(C=O)—NH—, and $L^5$ is bonded to the benzene ring at the para position;

(41) A method for producing a compound represented by the formula (XI), the compound being a polynucleotide comprising a sense strand polynucleotide corresponding to a target gene, and an antisense strand polynucleotide having a nucleotide sequence complementary to the sense strand polynucleotide, wherein the 5'-end of the antisense strand polynucleotide and the 3'-end of the sense strand polynucleotide are linked via X through phosphodiester bonds:

[Formula 4]

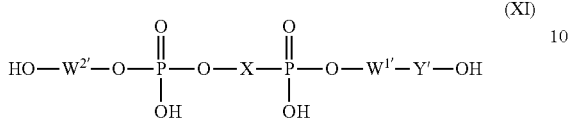

(XI)

wherein $W^{2'}$ represents a sense strand polynucleotide without 5'-terminal and 3'-terminal hydroxy groups; $W^{1'}$-$Y'$ represents an antisense strand polynucleotide without 5'-terminal and 3'-terminal hydroxy groups; and X represents the formula (XII):

[Formula 5]

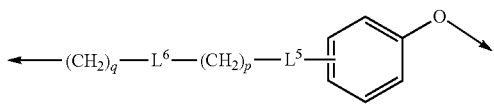

(XII)

wherein p represents an integer of 0 to 4; q represents an integer of 4 to 10; $L^5$ represents a single bond or —O—; $L^6$ represents —(C=O)—NH— or —NH—(C=O)— starting from the bond with $(CH_2)_p$; $L^5$ is bonded to the benzene ring at the para or meta position; provided that if $L^5$ is —O—, then p represents an integer of 1 to 4; and the terminal methylene group is bound to the 3'-end of the sense strand polynucleotide to form a phosphodiester bond; and the oxygen atom bonded to the phenyl group is bound to the 5'-end of the antisense strand polynucleotide to form a phosphodiester bond, the method comprising the steps of:

(i) reacting the hydroxy group of a compound represented by the formula Tr-O—X—H [wherein Tr represents a protective group for the hydroxy group, —$(CH_2)_q$— in X is bonded to Tr-O— and the oxygen atom bonded to the phenyl group is bonded to hydrogen] with a compound represented by the formula (XIII):

[Formula 6]

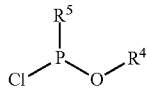

(XIII)

or the formula (XIV):

[Formula 7]

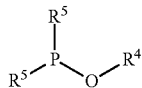

(XIV)

[wherein $R^4$ represents a 2-cyanoethyl group, a methyl group, a methanesulfonylethyl group, a 2,2,2-trichloroethyl group, or a 4-chlorophenylmethyl group, and $R^5$ represents a morpholino group, a diisopropylamino group, a diethylamino group, or a dimethylamino group]

to produce a compound represented by the formula (XV):

[Formula 8]

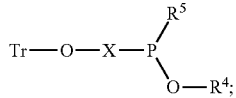

(XV)

(ii) reacting the compound obtained in step (i) with a compound represented by the formula HO—$W^1$—Y-CPG [wherein $W^1$—Y represents a protected antisense strand polynucleotide without 5'-terminal and 3'-terminal hydroxy groups, and CPG represents a polymer support having a linker capable of binding to the polynucleotide] by a phosphoramidite method and subsequently producing a moiety represented by the formula $Tr^1$-O—$W^2$—O—P(=O)($OR^4$)—O— [wherein $Tr^1$ represents a protective group for the hydroxy group, and $W^2$ represents a protected sense strand polynucleotide without 5'-terminal and 3'-terminal hydroxy groups] by a phosphoramidite method to produce a compound represented by the formula (XVI):

[Formula 9]

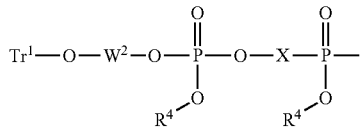

(XVI)

and (iii) excising the compound obtained in step (ii) from CPG and removing the protective group;

(42) The method according to (41), wherein Tr and $Tr^1$ are identically or differently a 4-methoxytrityl group, a 4,4'-dimethoxytrityl group, a pixyl group, a trityl group, a levulinyl group, or a bis(trimethylsilyloxy)(cyclohexyloxy)silyl group;

(43) The method according to (41), wherein Tr and $Tr^1$ are identically or differently a 4-methoxytrityl group or a 4,4'-dimethoxytrityl group, the sum of p and q is an integer of 4 or larger, $L^5$ is a single bond, $L^6$ is —(C=O)—NH—, and $L^5$ is bonded to the benzene ring at the para position;

(44) The method according to (41), wherein Tr and $Tr^1$ are identically or differently a 4-methoxytrityl group or a 4,4'-dimethoxytrityl group, the sum of p and q is an integer of 8 or larger, $L^5$ is a single bond, $L^6$ is —(C=O)—NH—, and $L^5$ is bonded to the benzene ring at the para position;

(45) The method according to (41), wherein Tr and $Tr^1$ are identically or differently a 4-methoxytrityl group or a 4,4'-dimethoxytrityl group, p is 0 or 2, q is an integer of 6 or larger, $L^5$ is a single bond, $L^6$ is —(C=O)—NH—, and $L^5$ is bonded to the benzene ring at the para position;

(46) The method according to (41), wherein Tr and $Tr^1$ are identically or differently a 4-methoxytrityl group or a 4,4'-dimethoxytrityl group, p is 0 or 2, q is 6 or 8, $L^5$ is a single bond, $L^6$ is —(C=O)—NH—, and $L^5$ is bonded to the benzene ring at the para position;

(47) The method according to (41), wherein Tr and $Tr^1$ are identically or differently a 4-methoxytrityl group or a 4,4'-dimethoxytrityl group, p is 0 or 2, q is 8, $L^5$ is a single bond, $L^6$ is —(C=O)—NH—, and $L^5$ is bonded to the benzene ring at the para position;

(48) The method according to (41), wherein Tr and $Tr^1$ are identically or differently a 4-methoxytrityl group or a 4,4'-dimethoxytrityl group, p is 2, q is 8, $L^5$ is a single bond, $L^6$ is —(C=O)—NH—, and $L^5$ is bonded to the benzene ring at the para position;

(49) The method according to (41), wherein each of Tr and $Tr^1$ is a 4,4'-dimethoxytrityl group, p is 2, q is 8, $L^5$ is a single bond, $L^6$ is —(C=O)—NH—, and $L^5$ is bonded to the benzene ring at the para position;

(50) The method according to any one of (41) to (49), wherein $R^4$ is a 2-cyanoethyl group, a methyl group, a methanesulfonylethyl group, a 2,2,2-trichloroethyl group, or a 4-chlorophenylmethyl group, and $R^5$ is a morpholino group, a diisopropylamino group, a diethylamino group, or a dimethylamino group;

(51) The method according to any one of (41) to (49), wherein $R^4$ is a 2-cyanoethyl group or a methyl group, and $R^5$ is a morpholino group or a diisopropylamino group;

(52) The method according to any one of (41) to (49), wherein the compound represented by the formula (XIII) is chloro(morpholino)methoxyphosphine, chloro(morpholino)cyanoethoxyphosphine, chloro(diisopropylamino)methoxyphosphine, or chloro(diisopropylamino)cyanoethoxyphosphine;

(53) The method according to any one of (41) to (49), wherein the compound represented by the formula (XIV) is bis(diisopropylamino)cyanoethoxyphosphine;

(54) A polynucleotide selected from the following or a salt thereof:

HO—$C^p$-$G^{m1p}$-$A^p$-$G^{m1p}$-$A^p$-$C^{m1p}$-$A^p$-$C^{m1p}$-$A^p$-$U^{m1p}$-$G^p$-$G^{m1p}$-$G^p$-$U^{m1p}$-$G^p$-$C^{m1p}$-$T^p$-$A^{m1p}$-X—P(=O)(OH)—O—$U^{m1p}$-$T^p$-$A^{m1p}$-$G^p$-$C^{m1p}$-$A^p$-$C^{m1p}$-$C^p$-$C^{m1p}$-$A^p$-$U^{m1p}$-$G^p$-$U^{m1p}$-$G^p$-$U^{m1p}$-$C^p$-$U^{m1p}$-$C^p$-$G^{m1p}$-$T^p$-$U^{m1t}$-H (HS-005),

HO—$C^p$-$A^{m1p}$-$G^p$-$A^{m1p}$-$C^p$-$A^{m1p}$-$C^p$-$A^{m1p}$-$T^p$-$G^{m1p}$-$G^p$-$G^{m1p}$-$T^p$-$G^{m1p}$-$C^p$-$U^{m1p}$-$A^p$-$U^{m1p}$-X—P(=O)(OH)—O—$U^{m1p}$-$A^p$-$U^{m1p}$-$A^p$-$G^{m1p}$-$C^p$-$A^{m1p}$-$C^{m1p}$-$C^p$-$A^{m1p}$-$T^p$-$G^{m1p}$-$T^p$-$G^{m1p}$-$T^p$-$G^{m1p}$-$T^p$-$G^{m1p}$-$T^p$-$U^{m1t}$-H (HS-006),

HO—P-$G^{m1p}$-$A^p$-$G^{m1p}$-$A^p$-$C^{m1p}$-$A^p$-$C^{m1p}$-$A^p$-$U^{m1p}$-$G^p$-$G^{m1p}$-$G^p$-$U^{m1p}$-$G^p$-$C^{m1p}$-$T^p$-$A^{m1p}$-X—P(=O)(OH)—O—$U^{m1p}$-$T^p$-$A^{m1p}$-$G^p$-$C^{m1p}$-$A^p$-$C^{m1p}$-$C^p$-$C^{m1p}$-$A^p$-$U^{m1p}$-$G^p$-$U^{m1p}$-$G^p$-$U^{m1p}$-$C^p$-$U^{m1p}$-$C^p$-$G^{m1p}$-$T^s$-$U^{m1t}$-H (HS-005s), or,

HO—$C^p$-$A^{m1p}$-$G^p$-$A^{m1p}$-$C^p$-$A^{m1p}$-$C^p$-$A^{m1p}$-$T^p$-$G^{m1p}$-$G^p$-$G^{m1p}$-$T^p$-$G^{m1p}$-$C^p$-$U^{m1p}$-$A^p$-$U^{m1p}$-X—P(=O)(OH)—O—$U^{m1p}$-$A^p$-$U^{m1p}$-$A^p$-$G^{m1p}$-$C^p$-$A^{m1p}$-$C^p$-$C^{m1p}$-$C^p$-$A^{m1p}$-$T^p$-$G^{m1p}$-$T^p$-$G^{m1p}$-$T^p$-$C^{m1p}$-$T^p$-$G^{m1p}$-$T^s$-$U^{m1t}$-H (HS-006s)

wherein each of $A^P$, $G^P$, $C^P$, $T^P$, $T^s$, $A^{m1p}$, $G^{m1p}$, $C^{m1p}$, $U^{m1p}$, and $U^{m1t}$ represents a nucleoside or a nucleotide having a structure represented by the following formula:

[Formula 10]

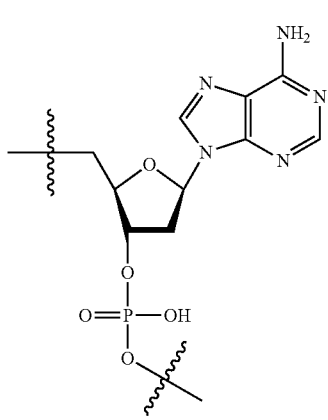

$A^p$

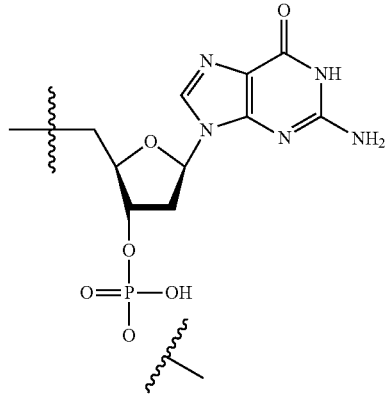

$G^p$

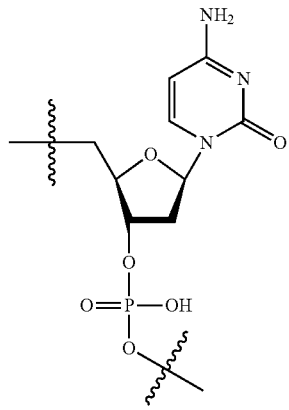

$C^p$

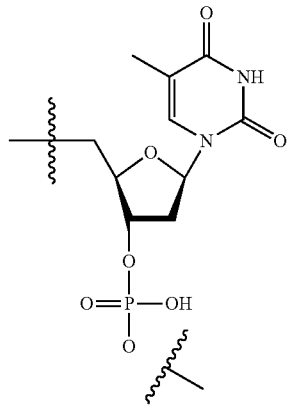

$T^p$

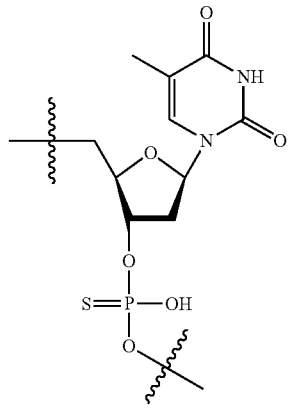

$T^s$

13
-continued

A<sup>m1p</sup>

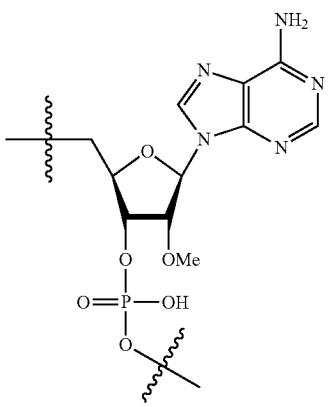

G<sup>m1p</sup>

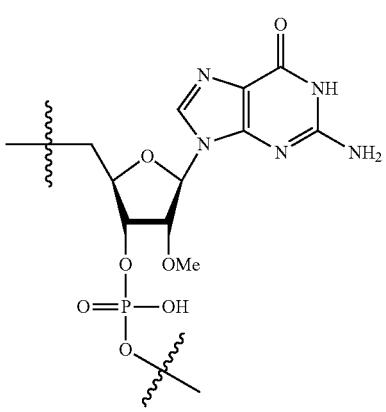

C<sup>m1p</sup>

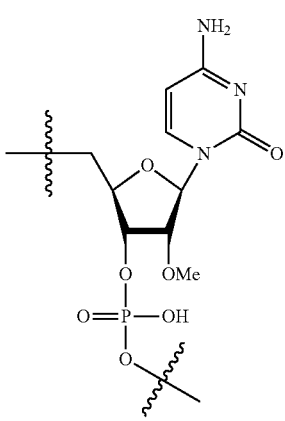

U<sup>m1p</sup>

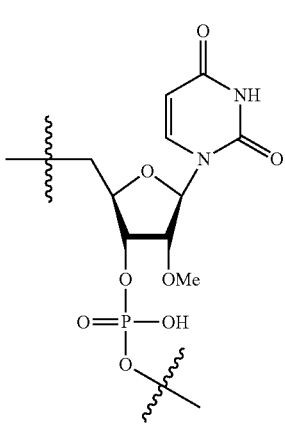

14
-continued

U<sup>m1t</sup>

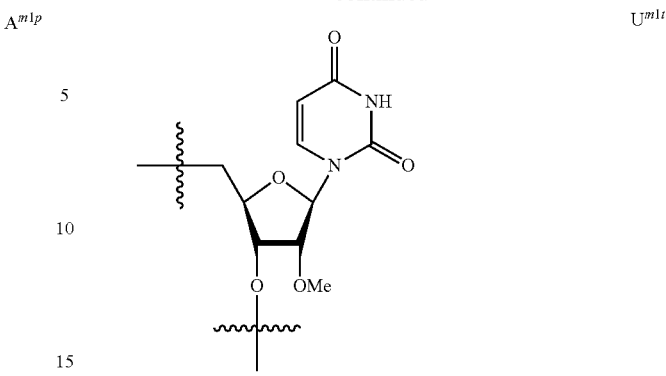

the sequence upstream from X represents a sense strand polynucleotide corresponding to a target gene; the sequence downstream from X represents a polynucleotide having an antisense strand polynucleotide having a nucleotide sequence complementary to the sense strand polynucleotide; X represents a linker having a structure represented by the formula (XVII):

[Formula 11]

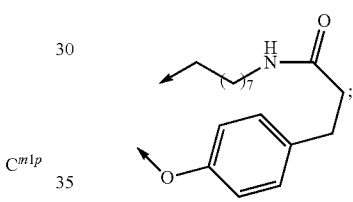

(XVII)

the terminal methylene group is bound to the 3'-end of the sense strand polynucleotide to form a phosphodiester bond; and the oxygen atom bonded to the phenyl group is bound to the 5'-end of the antisense strand polynucleotide to form a phosphodiester bond;

(55) A pharmaceutical composition comprising a polynucleotide or a salt thereof according to (54) as an active ingredient;

(56) The pharmaceutical composition according to (55), wherein the pharmaceutical composition is intended for the treatment of a disease derived from the expression of the Hsp47 gene;

(57) The pharmaceutical composition according to (56), wherein the disease derived from the expression of the Hsp47 gene is fibrosis;

(58) A method for inhibiting the expression of the Hsp47 gene, comprising administering a polynucleotide or a salt thereof according to (54) to a mammal;

(59) A reagent comprising a polynucleotide or a salt thereof according to (54).

Advantages of Invention

The present invention has provided a polynucleotide that has an RNA interference effect and/or a gene expression inhibitory effect. The present invention has also provided a polynucleotide that is resistant to at least any one enzyme selected from RNase, phosphatase, and exonuclease and has an RNA interference effect and/or a gene expression inhibitory effect. The present invention has further provided a polynucleotide that is resistant to RNase, phosphatase, and exonuclease and has an RNA interference effect and/or a gene expression inhibitory effect. The present invention has further provided a polynucleotide having an RNA interference effect and/or a gene expression inhibitory effect without the need of the step of separately producing a sense strand polynucleotide and an antisense strand polynucleotide and without the need of the complicated procedure of accurately mixing these strands in the same amounts to form a duplex. The present invention allows functional analysis of various genes using the polynucleotide and provides a pharmaceutical composition comprising the polynucleotide.

The present invention has also provided a synthetic intermediate useful for obtaining the polynucleotide. The present invention has further provided a method for producing the polynucleotide.

DESCRIPTION OF EMBODIMENTS

1. Description of Terms

Figure 1:
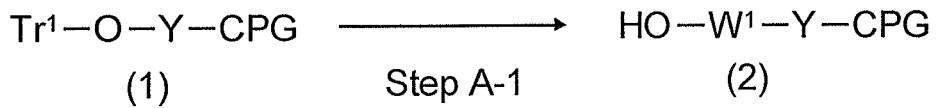
FIG. 1 is a diagram showing the outline of step A-1.

In the present specification, the "target gene" is not particularly limited as long as it is RNA in cells, tissues, or individuals to which or to whom this gene is introduced (hereinafter, they may be referred to as "recipients"). The target gene may be mRNA that is translated into a protein or may be non-coding RNA that is not translated into a protein. Examples of non-coding RNA include functional RNA, for example, an untranslated region of mRNA, tRNA, rRNA, mRNA-like non-coding RNA (mRNA-like ncRNA), long non-coding RNA (long ncRNA), small nuclear RNA (snRNA), small nucleolar RNA (snoRNA), and microRNA (miRNA). Specifically, the target gene may be endogenous to the recipients for introduction or may be exogenous and introduced thereto by an approach such as gene transfer. It may also be a gene present on a chromosome or on an extrachromosomal gene. Examples of the exogenous gene include, but are not limited to, those derived from viruses, bacteria, fungi, and protozoans, which can infect the recipients. The function of the gene may be known or unknown.

Examples of such a target gene can include genes whose expression is specifically increased and/or which are specifically mutated in patients having a particular disease. Examples of the disease can include a central nervous system disease (e.g., Alzheimer's disease, dementia, and eating disorders), inflammatory disease (e.g., allergy, rheumatism, osteoarthritis, and lupus erythematosus), cardiovascular disease (e.g., hypertension, cardiomegaly, angina pectoris, arteriosclerosis, and hypercholesterolemia), cancer (e.g., non-small cell lung cancer, ovarian cancer, prostatic cancer, gastric cancer, pancreatic cancer, liver cancer, bladder cancer, breast cancer, uterine cervix cancer, colorectal cancer, colon cancer, and rectal cancer), respiratory disease (e.g., pneumonia, bronchitis, asthma, and chronic obstructive pulmonary disease), diabetes mellitus, diabetic retinopathy, diabetic nephropathy, anemia (e.g., anemia associated with chronic disease and iron-refractory iron deficiency anemia), age-related macular degeneration, immunological disease (e.g., Crohn's disease, atopic dermatitis, an autoimmune disease, immunodeficiency, and leukemia), liver/gallbladder disease (e.g., non-alcoholic steatohepatitis, liver cirrhosis, hepatitis, liver failure, cholestasis, and calculus), gastrointestinal disease (e.g., an ulcer, enteritis, and malabsorption), infection, adiposity, and fibrosis (lung fibrosis, liver fibrosis, renal fibrosis, myelofibrosis, etc.). Examples of causative genes of these diseases can include, but are not limited to, kinesin spindle protein (KSP), vascular endothelial growth factor, (VEGF), transthyretin (TTR), proprotein convertase subtilisin/kexin type 9(PCSK9), polo-like kinase (PLK), ApoB-100, ribonucleotide reductase M2 subunit (RRM2), clusterin, heat shock protein 27 (Hsp27), survivin, eukaryotic initiation factor-4E (eIF-4E), intercellular adhesion molecule 1 (ICAM-1), the alpha subunit of the interleukin 4 receptor (IL-4R-alpha), Factor XI, Factor VII, N-ras, H-ras, K-ras, bcl-2, bcl-xL, Her-1, Her-2, Her-3, Her-4, MDR-1, human β-catenin gene, DDX3 (DEAD (Asp-Glu-Ala-Asp) box polypeptide 3, X-linked), Myeloid Cell Leukemia Sequence 1 (MCL1) gene, PKR (Eif2ak2), Hsp47 (Serpinh1), Hepcidin, active protein c (APC), signal tranducer and activator of transcription (STAT3).

In the present specification, the "natural nucleoside" refers to a 2'-deoxynucleoside such as 2'-deoxyadenosine, 2'-deoxyguanosine, 2'-deoxycytidine, 2'-deoxy-5-methylcytidine, and thymidine or a ribonucleoside such as adenosine, guanosine, cytidine, 5-methylcytidine, and uridine. Moreover, the "oligonucleotide" refers to an oligonucleotide composed of a compound in which the sugar moiety of the nucleoside forms an ester with phosphoric acid. In the present specification, the terms "oligonucleotide" and "polynucleotide" are used interchangeably.

In the present specification, 2'-deoxyadenosine may be referred to as $A^t$; 2'-deoxyguanosine may be referred to as $G^t$; 2'-deoxycytidine may be referred to as $C^t$; 2'-deoxy-5-methylcytidine may be referred to as $5meC^t$; thymidine may be referred to as $T^t$; 2'-deoxyuridine may be referred to as $U^t$; adenosine may be referred to as $A^{rt}$; guanosine may be referred to as $G^{rt}$; cytidine may be referred to as $C^{rt}$; 5-methylcytidine may be referred to as $5meC^{rt}$; and uridine may be referred to as $U^{rt}$. Moreover, in the present specification, 2'-deoxyadenosine nucleotide may be referred to as $A^P$; 2'-deoxyguanosine nucleotide may be referred to as $G^P$; 2'-deoxycytidine nucleotide may be referred to as $C^P$; 2'-deoxy-5-methylcytidine nucleotide may be referred to as $5meC^P$; a thymidine nucleotide may be referred to as $T^P$; a 2'-deoxyuridine nucleotide may be referred to as $U^P$; an adenosine nucleotide may be referred to as $A^{rp}$; a guanosine nucleotide may be referred to as $G^{rp}$; a cytidine nucleotide may be referred to as $C^{rp}$; a 5-methylcytidine nucleotide may be referred to as $5meC^{rp}$; and a uracil nucleotide may be referred to as $U^{rp}$.

In the present specification, where there are phosphorothioate ester forms instead of phosphoester forms of a nucleotide, a counterpart of $A^P$ may be referred to as $A^s$; a counterpart of $G^P$ may be referred to as $G^s$; a counterpart of $C^P$ may be referred to as $C^s$; a counterpart of $5meC^P$ may be referred to as $5meC^s$; a counterpart of $T^P$ may be referred to as $T^s$; a counterpart of $U^P$ may be referred to as $U^s$; a counterpart of $A^{rp}$ may be referred to as $A^{rs}$; a counterpart of $G^{rp}$ may be referred to as $G^{rs}$; a counterpart of $C^{rp}$ may be referred to as $C^{rs}$; a counterpart of $5meC^{rp}$ may be referred to as $5meC^{rs}$; and a counterpart of $U^{rp}$ may be referred to as $U^{rs}$.

In the present specification, the term "sugar-modified nucleoside" refers to a nucleoside whose sugar moiety has been modified.

In particular, examples of 2'-O-methyl modification include 2'-O-methylnucleoside and 2'-O-methylnucleotide; a counterpart of $A^{rt}$ may be referred to as $A^{m1t}$; a counterpart of $G^{rt}$ may be referred to as $G^{m1t}$; a counterpart of $C^{rt}$ may be referred to as $C^{m1t}$; a counterpart of $5meC^{rt}$ may be referred to as $5meC^{m1t}$; a counterpart of $U^{rt}$ may be referred to as $U^{m1t}$; a counterpart of $A^{rp}$ may be referred to as $A^{m1p}$; a counterpart of $G^{rp}$ may be referred to as $G^{m1p}$; a counterpart of $C^{rp}$ may be referred to as $C^{m1p}$; a counterpart of $5meC^{rp}$ may be referred to as $5meC^{m1p}$; a counterpart of $U^{rp}$ may be referred to as $U^{m1p}$; a counterpart of $A^{rs}$ may be referred to as $A^{m1s}$; a counterpart of $G^{rs}$ may be referred to as $G^{m1s}$; a counterpart of $C^{rs}$ may be referred to as $C^{m1s}$; a counterpart of $5meC^{rs}$ may be referred to as $5meC^{m1s}$; and a counterpart of $U^{rs}$ may be referred to as $U^{m1s}$.

In the present specification, the 2'-O,4'-C-ethylene nucleotide unit and the "ENA unit" refer to those nucleosides and nucleotides having an ENA and also refer to nucleosides and nucleotides having an ENA unit: a counterpart of $A^t$ may be referred to as $A^{2t}$; a counterpart of $A^P$ may be referred to as $A^{e2p}$; a counterpart of $A^s$ may be referred to as $A^{e2s}$; a counterpart of $G^t$ may be referred to as $G^{2t}$; a counterpart of $G^P$ may be referred to as $G^{e2p}$; a counterpart of $G^s$ may be referred to as $G^{e2s}$; a counterpart of $5meC^t$ may be referred to as $C^{2t}$; a counterpart of $5meC^P$ may be referred to as $C^{e2p}$; a counterpart of $5meC^s$ may be referred to as $C^{e2s}$; a counterpart of $T^t$ may be referred to as $T^{2t}$; a counterpart of $T^P$ may be referred to as $T^{e2p}$; and a counterpart of $T^s$ may be referred to as $T^{e2s}$.

In the present specification, the 2'-O,4'-C-methylene nucleotide unit and the "2',4'-BNA/LNA unit" refer to those nucleosides and nucleotides having a 2',4'-BNA/LNA and also refer to nucleosides and nucleotides having a 2',4'-BNA/LNA unit: a counterpart of $A^t$ may be referred to as $A^{1t}$; a counterpart of $A^P$ may be referred to as $A^{e1p}$; a counterpart of As may be referred to as $A^{e1s}$; a counterpart of $G^t$ may be referred to as $G^{1t}$; a counterpart of $G^P$ may be referred to as $G^{e1p}$; a counterpart of $G^s$ may be referred to as $G^{e1s}$; a counterpart of $5meC^t$ may be referred to as $C^{1t}$; a counterpart of $5meC^P$ may be referred to as $C^{e1p}$; a counterpart of $5meC^s$ may be referred to as $C^{e1s}$; a counterpart of $T^t$ may be referred to as $T^{1t}$; a counterpart of $T^P$ may be referred to as $T^{e1p}$; and a counterpart of $T^s$ may be referred to as $T^{e1s}$.

Hereinafter, the structural formula of each nucleotide is shown.

[Formula 12]

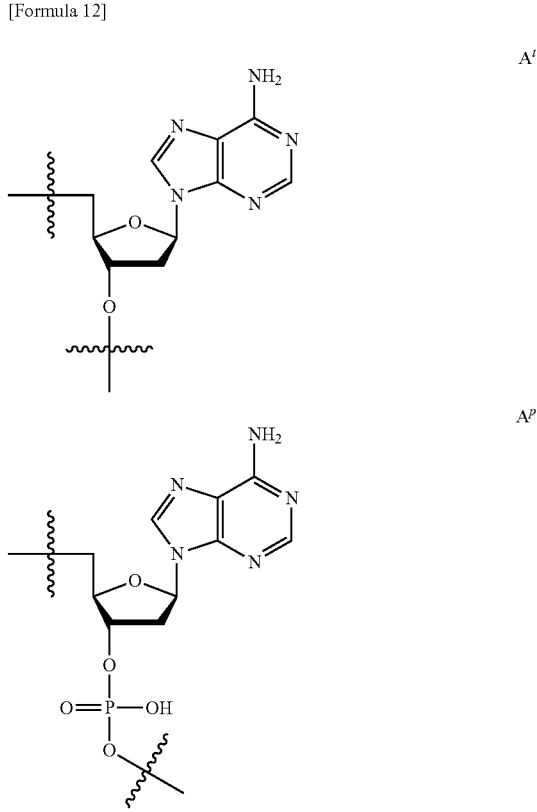

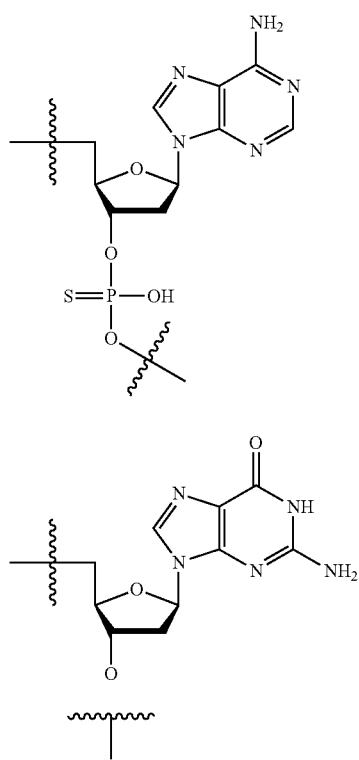
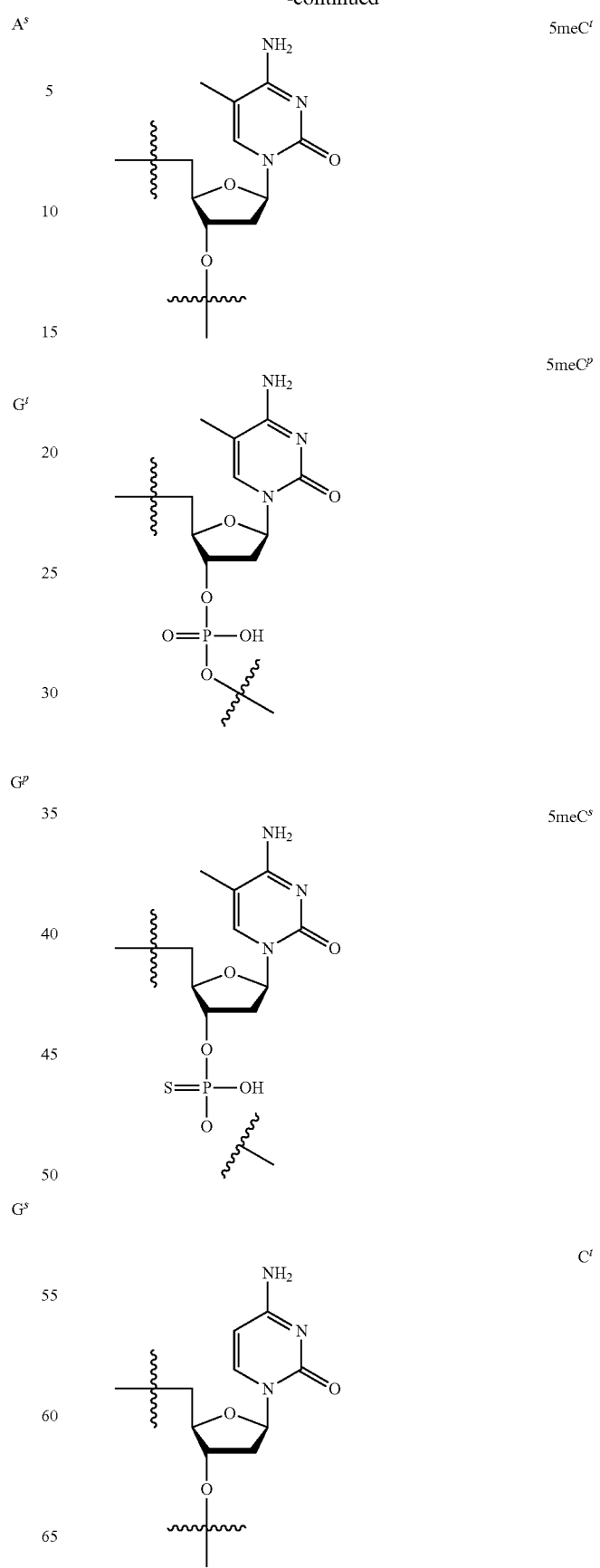

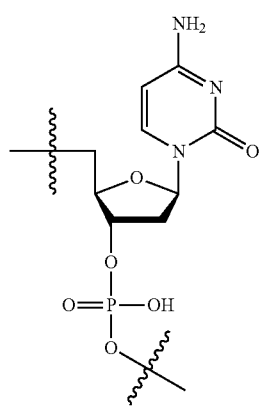
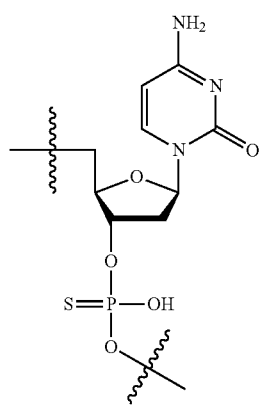
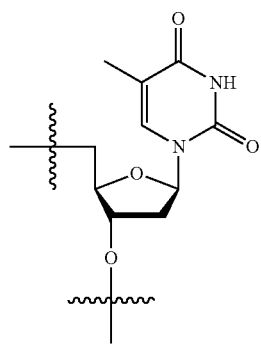
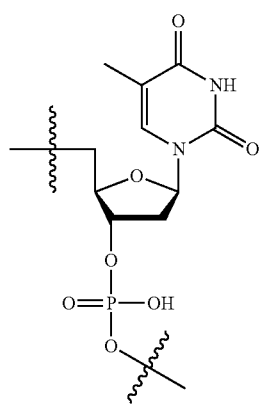
C^p
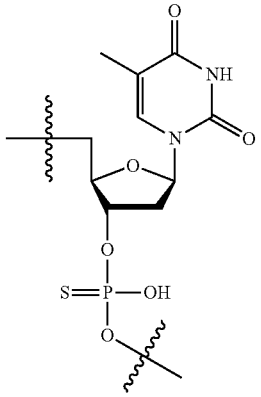
C^s
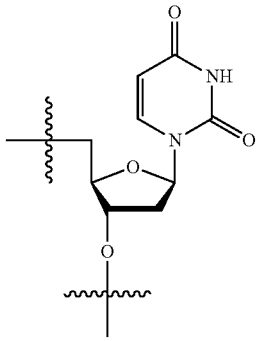
T^t
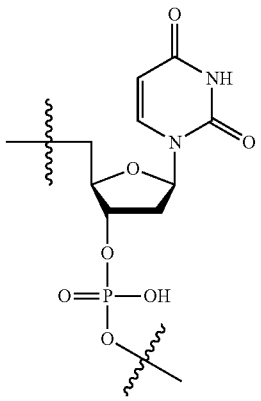
T^p
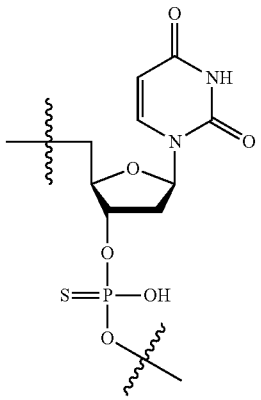
T^s
U^t
U^p
U^s 23
-continued
[Formula 13]
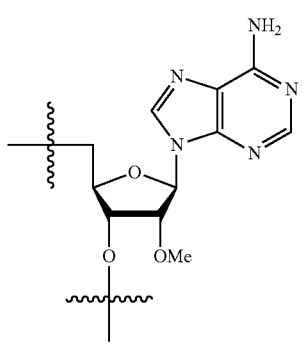
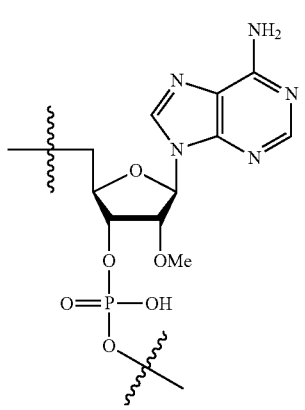
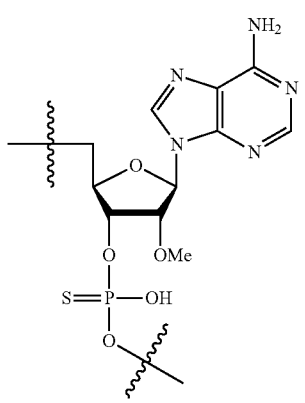
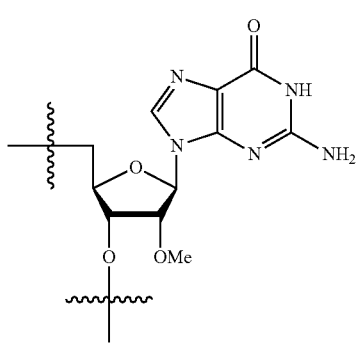
24
-continued
A$^{m1t}$
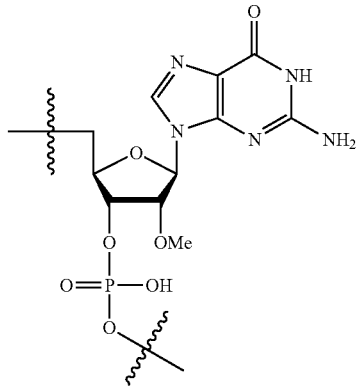 G$^{m1p}$
A$^{m1p}$
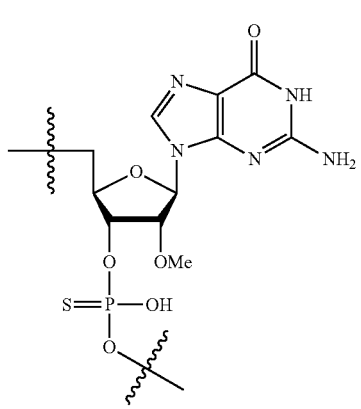 G$^{m1s}$
A$^{m1s}$
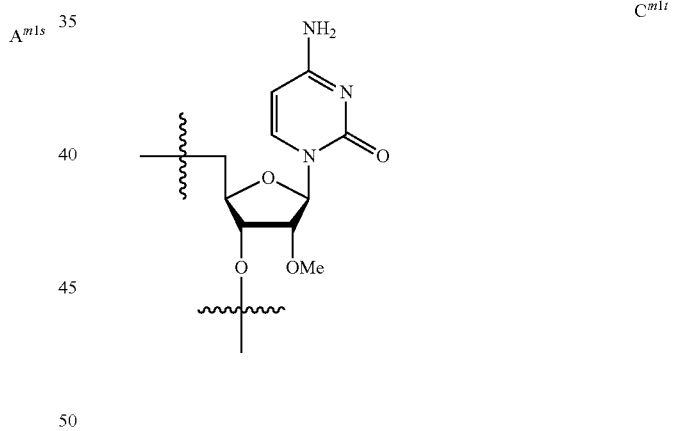 C$^{m1t}$
G$^{m1t}$
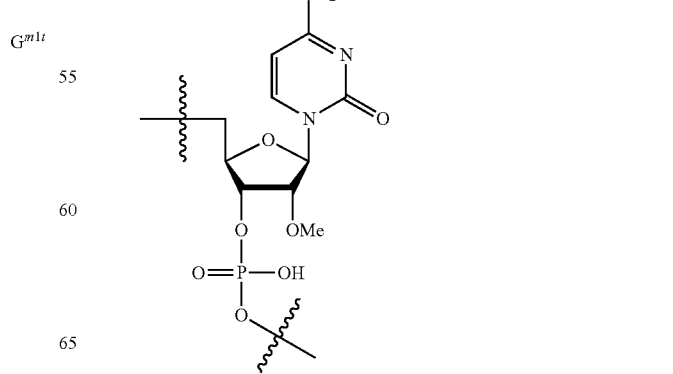 C$^{m1p}$ -continued
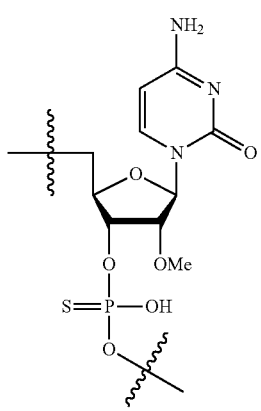
C^{m1s}
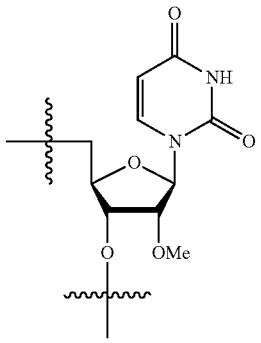
U^{m1t}
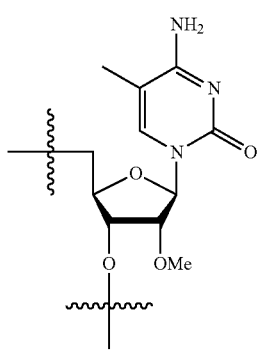
5meC^{m1t}
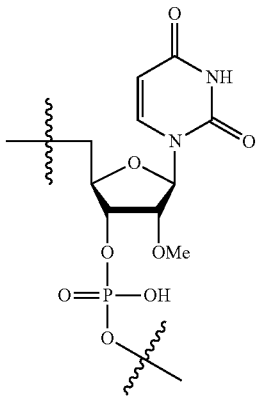
U^{m1p}
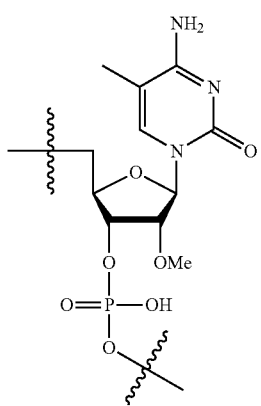
5meC^{m1p}
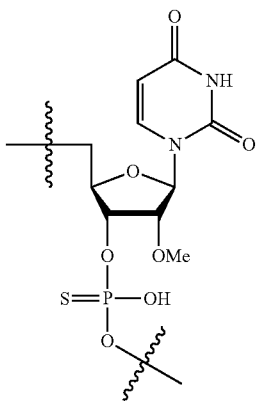
U^{m1s}
[Formula 14]
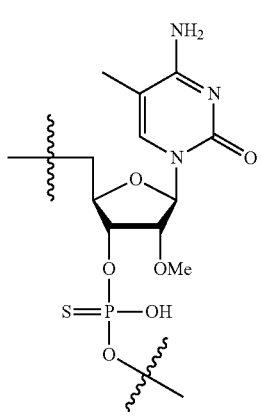
5meC^{m1s}
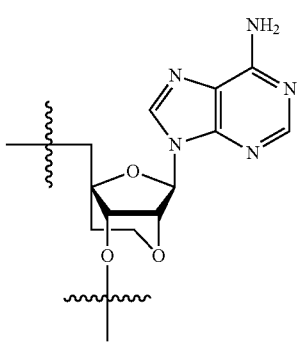
A^{2t}

27
-continued
A<sup>e2p</sup>
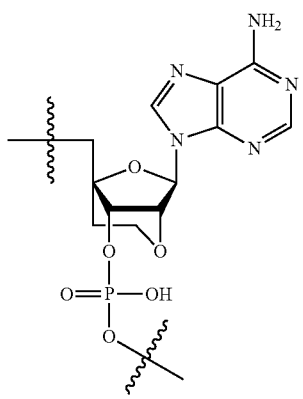
A<sup>e2s</sup>
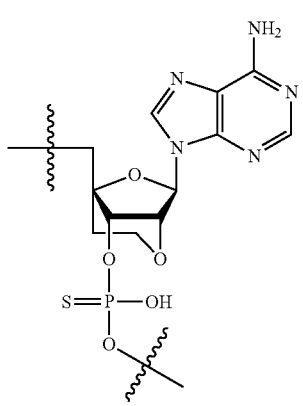
G<sup>2t</sup>
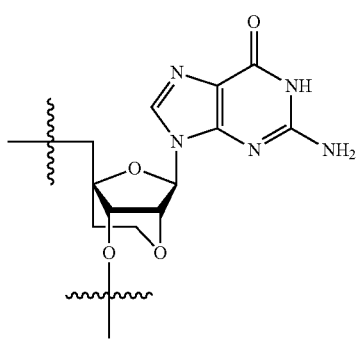
G<sup>e2p</sup>
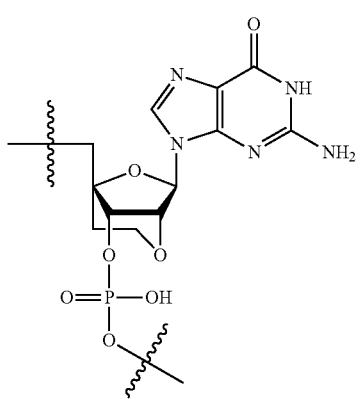
28
-continued
G<sup>e2s</sup>
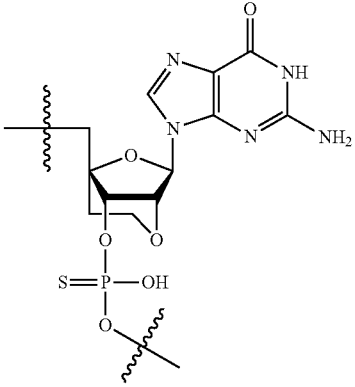
C<sup>2t</sup>
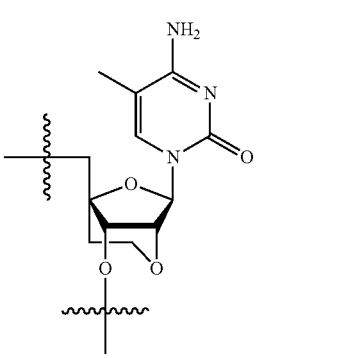
C<sup>e2p</sup>
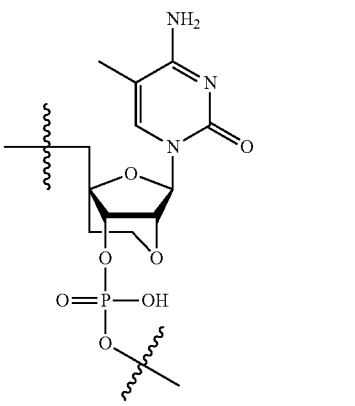
C<sup>e2s</sup>
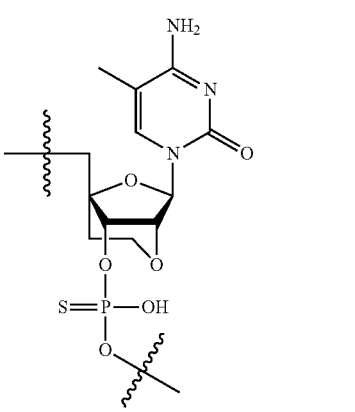

29
-continued
$T^{2t}$
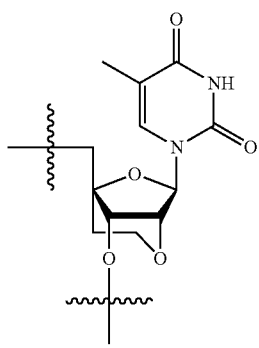
$T^{e2p}$
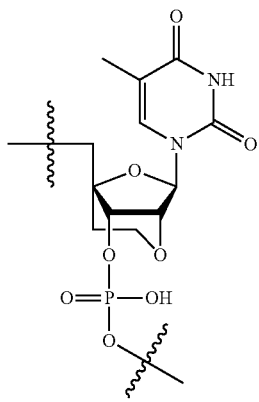
$T^{e2s}$
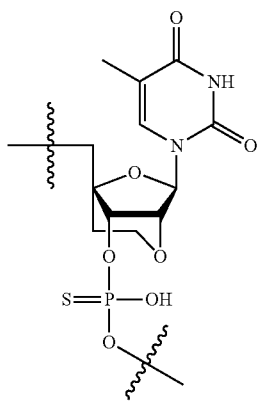
[Formula 15]
$A^{1t}$
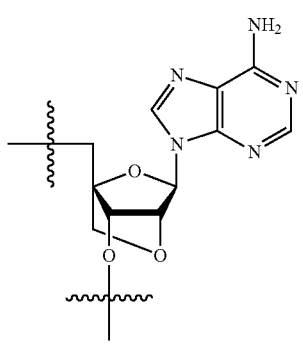
30
-continued
$A^{e1p}$
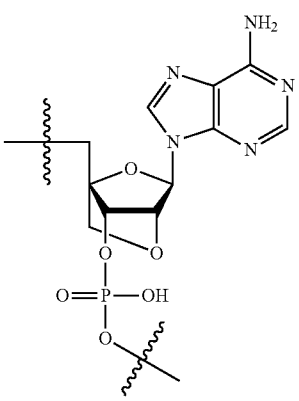
$A^{e1s}$
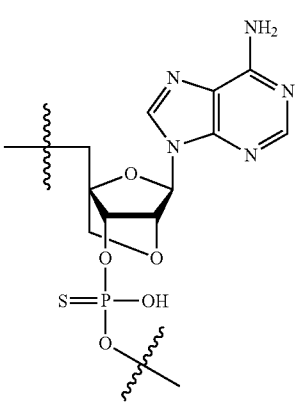
$G^{1t}$
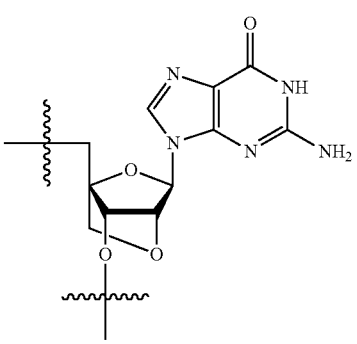
$G^{e1p}$
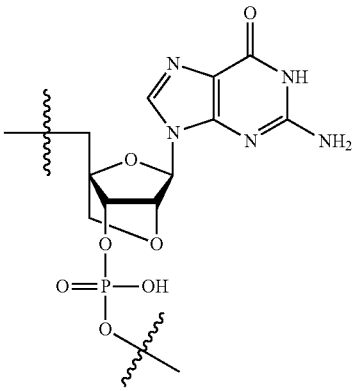

$G^{els}$
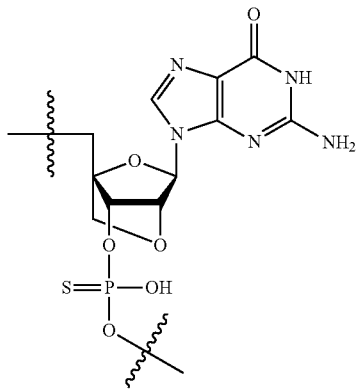
$T^{lt}$
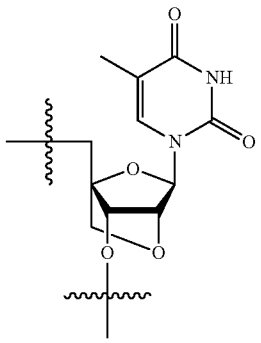
$C^{lt}$
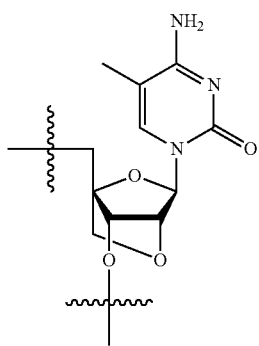
$T^{elp}$
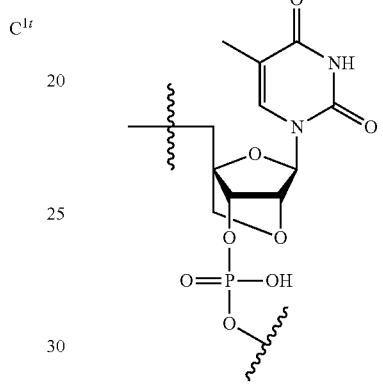
$C^{elp}$
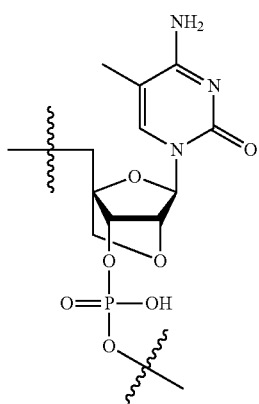
$T^{els}$
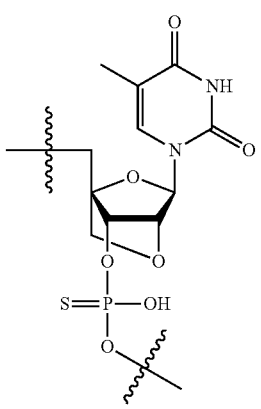
$C^{els}$
[Formula 16]
$A^{m2t}$
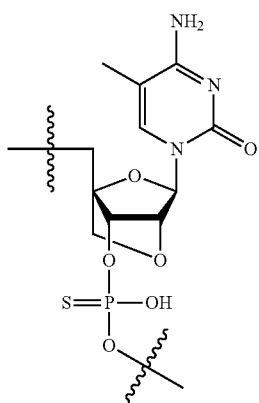
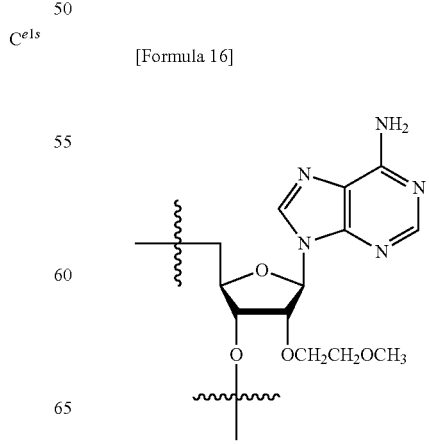

33
-continued
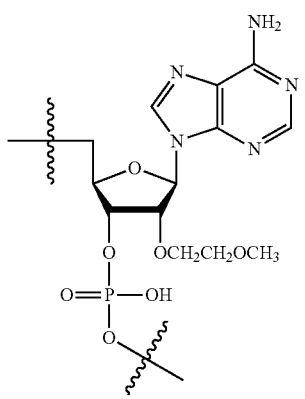
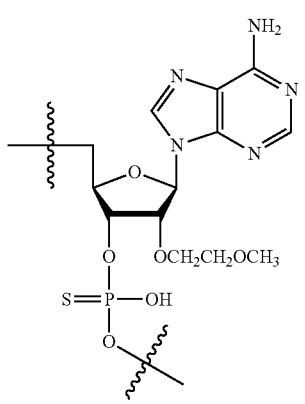
$A^{m2p}$
$A^{m2s}$
$G^{m2t}$
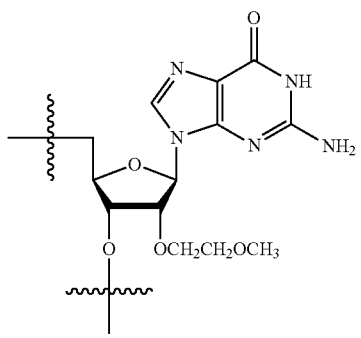
$G^{m2p}$
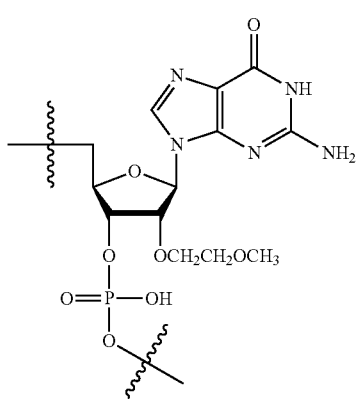
34
-continued
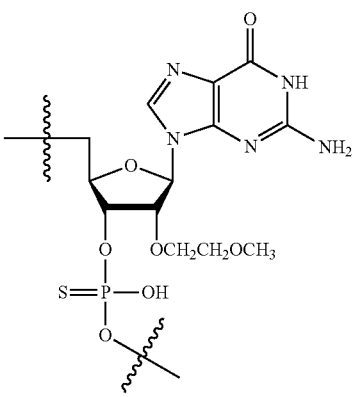
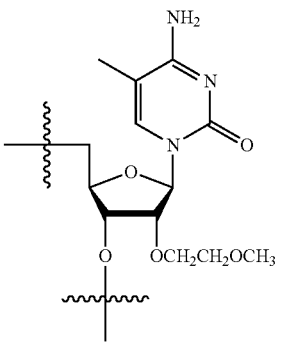
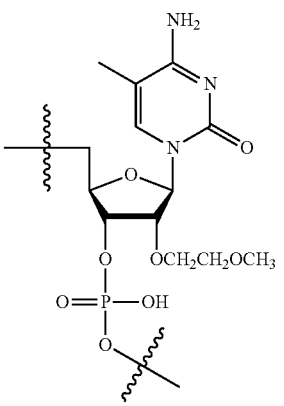
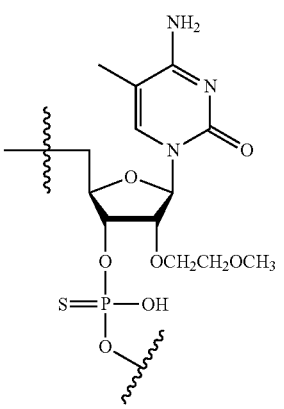
$G^{m2s}$
$5meC^{m2t}$
$5meC^{m2p}$
$5meC^{m2s}$ 35
-continued
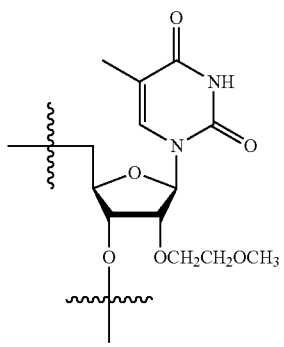
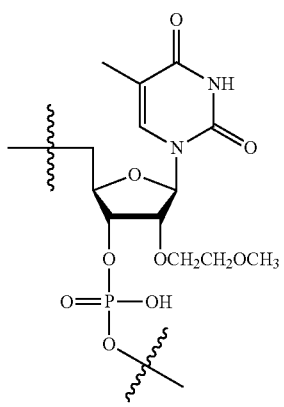
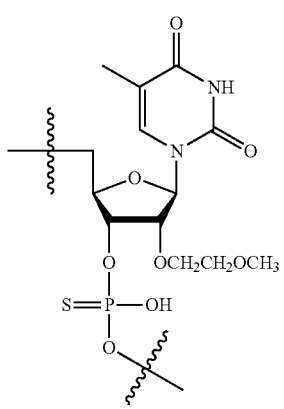
[Formula 17]
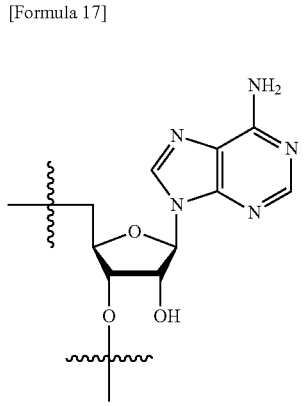
36
-continued
T^{m2t}
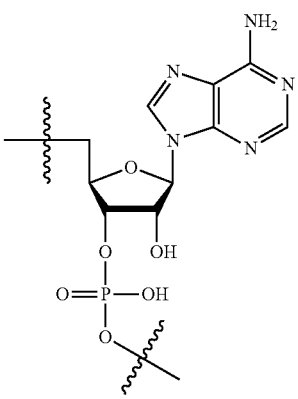 A^{rp}
T^{m2p}
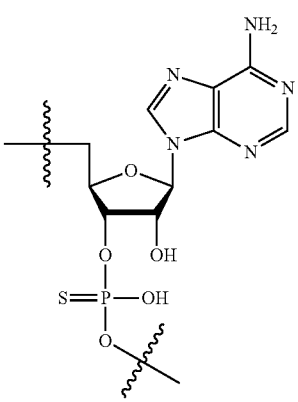 A^{rs}
T^{m2s}
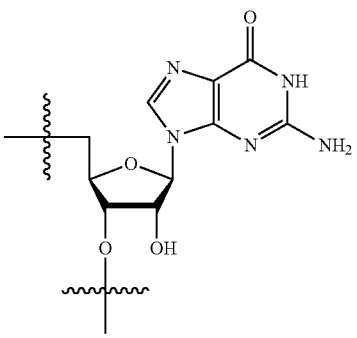 G^{rt}
A^{rt}
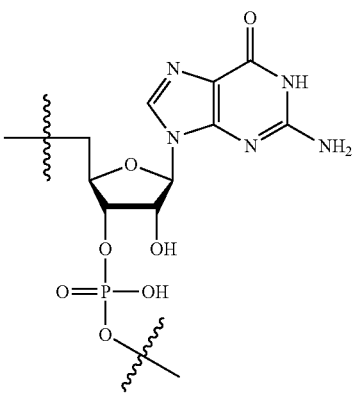 G^{rp}

G<sup>rs</sup>

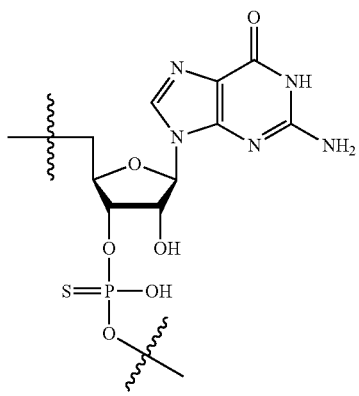

C<sup>rt</sup>

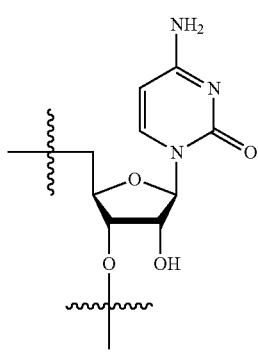

C<sup>rp</sup>

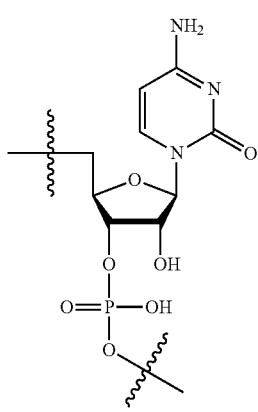

C<sup>rs</sup>

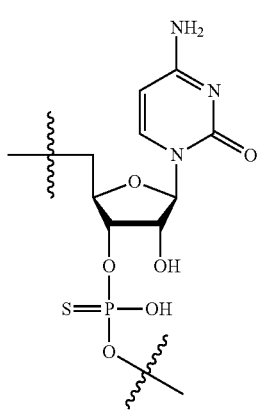

U<sup>rt</sup>

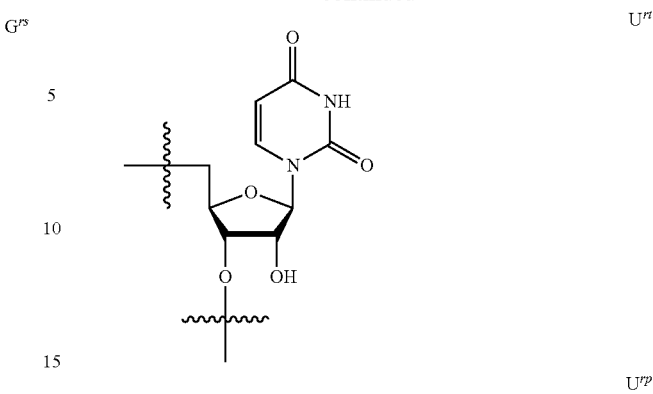

U<sup>rp</sup>

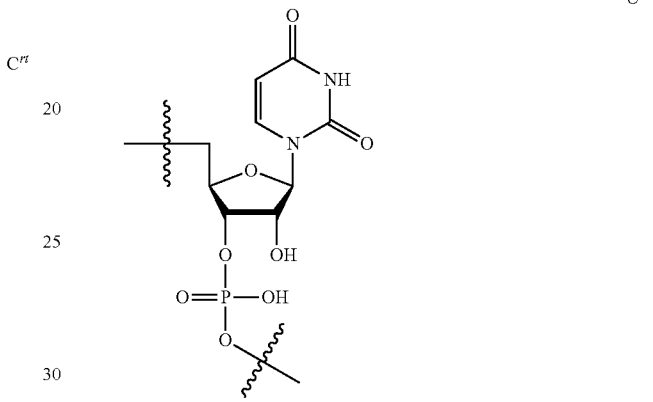

U<sup>rs</sup>

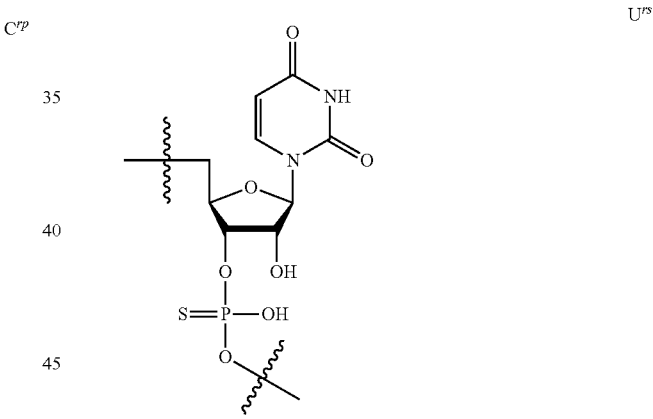

In the present specification, a feature of the polynucleotide or a salt thereof is that the polynucleotide is derived from a double-stranded polynucleotide comprising a sense strand polynucleotide corresponding to a target gene, and an antisense strand polynucleotide having a nucleotide sequence complementary to the sense strand polynucleotide, and has a single-stranded structure in which the 5'-end of the antisense strand and the 3'-end of the sense strand are linked via a linker structurally defined by a structural formula shown below to form a phosphodiester structure at each of these ends. Specifically, the polynucleotide has the following structure: polynucleotide-3'-P(=O)(OH)-[linker]-P(=O)(OH)-5'-polynucleotide wherein "polynucleotide-3'" represents the structure of the polynucleotide without a hydrogen atom on its 3'-terminal hydroxy group, and "5'-polynucleotide" represents the structure of the polynucleotide without a hydrogen atom on its 5'-terminal hydroxy group.

This linker contains a phenyl group. The linker is bound, at an oxygen atom moiety (which refers to an oxygen atom defined by the structural formula shown in Formula 18 below) bonded to the phenyl group, to the 5'-end of the antisense strand to form a phosphodiester bond at this 5'-end. This phenyl group further has $R^1$, $R^2$, and $R^3$, one of which serves as a site bound to the 3'-end of the sense strand to form a phosphodiester bond at this 3'-end. Even if $R^1$, $R^2$, and $R^3$ are bonded to the phenyl group via oxygen atoms, these oxygen atoms do not serve as sites bound to the 5'-end of the antisense strand. The structure of this linker is as follows:

[Formula 18]

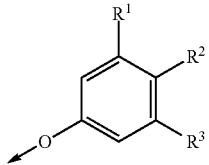

wherein
the shown oxygen atom bonded to the phenyl group is bound to the 5'-end of the antisense strand to form a phosphodiester structure;
any one of $R^1$, $R^2$, and $R^3$ represents a structure represented by the following formula:

wherein
m represents an integer of 0 to 4,
n1 represents an integer of 0 to 4,
n2 represents 0 or an integer of 2 to 10,
$L^1$ represents a single bond or —O—,
$L^2$ represents a single bond or —CH(—NH-$L^4$-R)—,
$L^3$ represents a single bond, —(C=O)—NH—, or —NH—(C=O)—,
provided that if $L^3$ is not a single bond, then n2 represents an integer of 2 to 10,
provided that if each of $L^1$ and $L^2$ is a single bond, m is 1, and each of n1 and n2 is 0, then $L^3$-O→ represents
—CH(COOH)NH-(amino acid residue)$_j$-Ser,
—CH(COOH)NH-(amino acid residue)$_j$-Thr,
—CH(NH$_2$)CO-(amino acid residue)$_j$-Ser, or
—CH(NH$_2$)CO-(amino acid residue)$_j$-Thr, wherein
the hydroxy group moiety of this serine or threonine is bound to the 3'-terminal phosphate group of the sense strand polynucleotide to form a phosphodiester structure,
j represents an integer of 0 to 2,
$L^4$ represents a single bond, —(C=O)—(CH$_2$)$_k$—NH—, or —(C=O)—(CH$_2$)$_k$—,
k represents an integer of 1 to 6, and
R represents a hydrogen atom, an alkyl group having 1 to 6 carbon atoms, a saturated or unsaturated hydrocarbon-carbonyl group having 2 to 30 carbon atoms, or a saturated or unsaturated hydrocarbon-oxycarbonyl group having 2 to 30 carbon atoms; and
the remaining two of $R^1$, $R^2$, and $R^3$ each independently represent a group selected from the group consisting of
a hydrogen atom,
an alkyl group having 1 to 8 carbon atoms which may have a substituent,
an alkoxy group having 1 to 8 carbon atoms which may have a substituent,
a halogen atom,
an alkylcarbonylamino group having an alkyl group having 1 to 9 carbon atoms, and
an alkylcarbonyl group containing an alkyl group having 1 to 8 carbon atoms which may have a substituent.

The phenyl group contained in the linker has $R^1$, $R^2$, and $R^3$, one of which has a linker function and serves as a site bound to the 3'-end of the sense strand. The structural feature of this moiety is to form a phosphodiester structure. The remaining two moieties are merely substituents, without the linker function, on the phenyl group.

A moiety other than the phenyl group moiety in the structure having the linker function, i.e., -$L^1$-(CH$_2$)$_m$-$L^2$-$L^3$-(CH$_2$CH$_2$O)$_{n1}$—(CH$_2$)$_{n2}$—O→, will be described.

$L^1$ is a single bond or a divalent oxygen atom —O—.

$L^2$ is a single bond or a structure having an amino group which may have a substituent on the carbon atom of methylene. This amino group has a substituent R via a linker structure $L^4$.

$L^4$ is a single bond, a methylene group, a polymethylene group having 2 to 4 carbon atoms, or a structure —(C=O)—CH$_2$—CH$_2$—(C=O)—O—. A carbonyl group in the structure —(C=O)—CH$_2$—CH$_2$—(C=O)—O— is bonded to the amino group at the left end of the structural formula to form a structure —NH—(C=O)—CH$_2$—CH$_2$—(C=O)—.

When R is an alkyl group having 1 to 6 carbon atoms, this alkyl group may be linear or branched. Examples thereof can include a methyl group, an ethyl group, a propyl group, an isopropyl group, a butyl group, an isobutyl group, a secondary butyl group, a pentyl group, and a hexyl group.

When R is an alkyl group having 1 to 6 carbon atoms, this group may be linear or branched. Examples thereof can include a methyl group, an ethyl group, a propyl group, an isopropyl group, a butyl group, an isobutyl group, a secondary butyl group, a pentyl group, and a hexyl group.

When R is a saturated or unsaturated hydrocarbon-carbonyl group having 2 to 30 carbon atoms (hydrocarbon group-(C=O)—) or is a saturated or unsaturated hydrocarbon-oxycarbonyl group having 2 to 30 carbon atoms (hydrocarbon group-O—(C=O)—), these hydrocarbon group moieties may be linear or branched. Also, the hydrocarbon group may be saturated or unsaturated. Examples of such a hydrocarbon group can include a group derived from aliphatic hydrocarbon. Examples of the hydrocarbon group can include an alkyl group having up to 30 carbon atoms. In addition, alkanes that are unsaturated by a carbon-carbon double bond in this alkyl group may be used. Alternatively, this hydrocarbon group moiety may contain an unsaturated bond to form a condensed ring structure. Examples of such a cyclic hydrocarbon group can include a cholesteryl group.

[Formula 19]

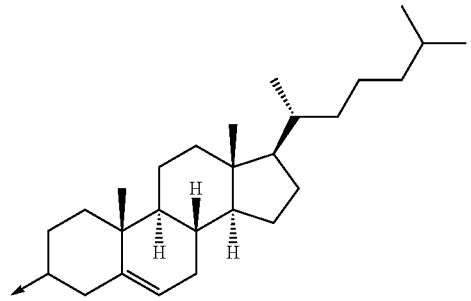

$L^3$ is a single bond or a structure —(C=O)—NH— or —NH—(C=O)—. $L^3$ is bonded at its left end to $L^2$ and, in some cases, may be bonded directly to the phenyl group shown in Formula 8. When $L^3$ is not a single bond, i.e., when $L^3$ is —(C=O)—NH— or —NH—(C=O)—, the structure bonded thereto as shown below inevitably contains a methylene group or a polymethylene group. This means that n2 is not 0 in this case.

$L^3$ is bonded at its right end to the structure —(CH$_2$CH$_2$O)$_{n1}$—(CH$_2$)$_{n2}$—O→. $L^3$ may be bonded to one dimethyleneoxy structure (n1=1) or 2 to 4 repeats of this unit (n1=2 to 4). In some cases, this dimethyleneoxy structure may be absent. 2 or 3 repeats of the dimethyleneoxy structure are preferable. In other words, n1 is preferably 2 or 3. Two dimethyleneoxy structures, i.e., n1 is 2, are more preferable.

This dimethyleneoxy structure is bonded at its right end to a methylene group or a polymethylene (up to decamethylene) group. This methylene group or polymethylene group may be absent. The methylene group or polymethylene group is preferably a polymethylene group. When the polymethylene group is present, its chain length is preferably 2 to 10 carbon atoms. A longer polymethylene chain is more preferable. A polymethylene chain having 5 or more carbon atoms is preferable. A polymethylene chain having 7 or more carbon atoms is more preferable.

The dimethyleneoxy structure and the methylene group or polymethylene group may coexist with each other. In this case, the chain length can be approximately 2 to 10 atoms.

When each of $L^1$ and $L^2$ is a single bond, m is 1, and each of n1 and n2 is 0, the moiety -L-(CH$_2$)$_m$-L$^2$-L$^3$-(CH$_2$CH$_2$O)$_{n1}$—(CH$_2$)$_{n2}$—O→ is $L^3$-O→. This $L^3$-O→ represents one of structures —CH(COOH)NH-(amino acid residue)$_j$-Ser, —CH(COOH)NH-(amino acid residue)$_j$-Thr, —CH(NH$_2$)CO-(amino acid residue)$_j$-Ser, and —CH(NH$_2$)CO-(amino acid residue)$_j$-Thr.

Each of these structures forms a polypeptide. This polypeptide can have tyrosine at one end and a hydroxy group-containing amino acid at the other end. The phenyl group of this tyrosine residue serves as a site bound to the phosphodiester structure at the 5'-end, while the hydroxy group moiety of the amino acid at the other end serves as a site bound to the phosphodiester structure at the 3'-end. The amino acid bound to the 3'-end may be any hydroxy group-containing amino acid and can be serine or threonine. The amino group of this serine or threonine may be substituted by an acyl group. This acyl group can be a phenylcarbonyl group or an alkylcarbonyl group. The phenyl group of the phenylcarbonyl group may be substituted by an alkyl group having 1 to 6 carbon atoms, an alkoxy group having 1 to 6 carbon atoms, a halogen atom, or the like. The alkyl group of the alkylcarbonyl group can be an alkyl group having 1 to 6 carbon atoms which may be linear or branched. This alkyl group may be further substituted by an alkoxy group having 1 to 6 carbon atoms, a halogen atom, or the like. Of such acyl groups, an alkylcarbonyl group is preferable, and an acetyl group is particularly preferable.

For example, the structure ←O-Ph-CH(COOH)NH-(amino acid residue)$_j$-Ser is a structure in which the amino group of tyrosine is bound to serine or a polypeptide having terminal serine. This peptide structure may be bound thereto at the carboxy terminal of tyrosine to form a polypeptide, as in ←O-Ph-CH(NH$_2$)CO-(amino acid residue)$_j$-Ser.

The amino acids constituting the polypeptide may be in an L-, D-, or DL-form.

The polypeptide may be any of a dipeptide to a tetrapeptide. The amino acid bound to tyrosine and serine or threonine is not particularly limited and can be any amino acid selected from glycine, alanine, β-alanine, valine, leucine, isoleucine, methionine, phenylalanine, tryptophan, proline, histidine, arginine, lysine, cysteine, glutamine, asparagine, serine, threonine, tyrosine, aspartic acid, glutamic acid, and the like. The amino acid is preferably glycine, alanine, or f-alanine. The diamino acid bound to tyrosine and serine or threonine is not particularly limited and may be any diamino acid composed of the amino acids described above. The amino acids are preferably glycine-glycine, glycine-alanine, glycine-β-alanine, alanine-glycine, alanine-alanine, alanine-β-alanine, β-alanine-glycine, β-alanine-alanine, or β-alanine-β-alanine.

Any one of $R^1$, $R^2$, and $R^3$ present on the phenyl group constituting the linker serves as a linker function with the structure represented by -L-(CH$_2$)$_m$-L$^2$-L$^3$-(CH$_2$CH$_2$O)$_{n1}$—(CH$_2$)$_{n2}$—O→. The remaining two of $R^1$, $R^2$, and $R^3$ are substituents on the phenyl group. Such substituents can each be independently a group selected from the group consisting of a hydrogen atom, an alkyl group having 1 to 8 carbon atoms which may have a substituent, an alkoxy group having 1 to 8 carbon atoms which may have a substituent, a halogen atom, an alkylcarbonylamino group having an alkyl group having 1 to 9 carbon atoms, and an alkylcarbonyl group containing an alkyl group having 1 to 8 carbon atoms which may have a substituent.

When two of $R^1$, $R^2$, and $R^3$ are each independently an alkyl group having 1 to 8 carbon atoms and optionally having a substituent, the alkyl group may be linear or branched. Examples thereof can include a methyl group, an ethyl group, a propyl group, an isopropyl group, a butyl group, an isobutyl group, a secondary butyl group, a pentyl group, a hexyl group, a heptyl group, and an octyl group. When the alkyl group has a substituent, the alkyl group may have, as the substituent, 1 or 2 or more groups selected from the substituent group consisting of a hydroxy group, an amino group, a halogen atom, an alkylthio group having 1 to 6 carbon atoms, an alkoxy group having 1 to 6 carbon atoms, a carboxy group, and an alkoxycarbonyl group containing an alkoxy group having 1 to 6 carbon atoms. The 1 or more substituents may be the same or different. When a hydroxy group or an amino group is used as the substituent in the alkyl group, it is more preferred that the alkyl group should be substituted by this group on the terminal carbon atom thereof. The alkyl group having a hydroxy group is preferably a hydroxymethyl group, a 2-hydroxyethyl group, a 2-hydroxypropyl group, or a 3-hydroxypropyl group. When a halogen atom is used as the substituent in the alkyl group, the alkyl group can be any of linear or branched alkyl groups having 1 to 6 carbon atoms and is more preferably a methyl group or an ethyl group, particularly preferably a methyl group, having a halogen atom. When a halogen atom is used as the substituent in the alkyl group, the halogen atom is preferably a fluorine atom. The fluorine atom(s) may be a mono-substitution or a per-fluoro-substitution. Examples of such an alkyl group can include a monofluoromethyl group, a difluoromethyl group, a trifluoromethyl group, and a 2,2,2-trifluoroethyl group. A monofluoromethyl group, a difluoromethyl group, and a trifluoromethyl group are preferable. The alkyl group in the alkylthio group having 1 to 6 carbon atoms and the alkoxy group having 1 to 6 carbon atoms may be linear or branched, and examples thereof can include a methyl group, an ethyl group, a propyl group, an isopropyl group, a butyl group, an isobutyl group, and a secondary butyl group. When a carboxy group or an alkoxycarbonyl group containing an alkoxy group having 1 to 6 carbon atoms is used as the substituent in the alkyl group, it is more preferred that the alkyl group should be substituted by this group on the terminal carbon atom thereof. The alkyl group in the alkoxycarbonyl group containing an alkoxy group having 1 to 6 carbon atoms may be linear or branched, and examples thereof can include a methyl group, an ethyl group, a propyl group, an isopropyl group, a butyl group, an isobutyl group, and a secondary butyl group.

When two of $R^1$, $R^2$, and $R^3$ are each independently an alkoxy group having 1 to 8 carbon atoms and optionally having a substituent, this alkoxy group can be any alkoxy group composed of the alkyl group shown above and an oxygen atom.

When two of $R^1$, $R^2$, and $R^3$ are each independently a halogen atom, this halogen atom can be a fluorine atom, a chlorine atom, a bromine atom, or an iodine atom. Of these, a chlorine atom or a fluorine atom is preferable. A fluorine atom is more preferable.

When two of $R^1$, $R^2$, and $R^3$ are each independently an alkylcarbonyl group (aliphatic acyl group) containing an alkyl group having 1 to 9 carbon atoms which may have a substituent, this alkyl moiety can be an alkyl group having up to 9 carbon atoms, which includes the alkyl group having 1 to 8 carbon atoms as shown above. The alkylcarbonyl group can be constituted of such an alkyl group and a carbonyl group. The alkylcarbonyl group is preferably an acetyl group.

$R^1$, $R^2$, and $R^3$ are preferably a hydrogen atom for each of $R^1$ and $R^3$ and a linker structure represented by -$L^1$-$(CH_2)_m$-$L^2$-$L^3$-$(CH_2CH_2O)_{n1}$—$(CH_2)_{n2}$—O→ for $R^2$.

When each of $R^1$ and $R^3$ is a hydrogen atom, the linker structure represented by $R^2$ is preferably a combination as follows:

each of $L^1$ and $L^2$ is a single bond, $L^3$ is —(C=O)—NH—, and the sum of m and n2 is an integer of 3 or larger;

each of $L^1$ and $L^2$ is a single bond, $L^3$ is —(C=O)—NH—, and the sum of m and n2 is an integer of 8 or larger;

each of $L^1$ and $L^2$ is a single bond, $L^3$ is —(C=O)—NH—, m is 0 or 2, and n2 is an integer of 6 or larger;

each of $L^1$ and $L^2$ is a single bond, $L^3$ is —(C=O)—NH—, m is 0 or 2, and n2 is 6 or 8;

each of $L^1$ and $L^2$ is a single bond, $L^3$ is —(C=O)—NH—, m is 0 or 2, and n2 is 8; or each of $L^1$ and $L^2$ is a single bond, $L^3$ is —(C=O)—NH—, m is 2, and n2 is 8.

In the present specification, the polynucleotide described above, a feature of which is that the polynucleotide is derived from a double-stranded polynucleotide comprising a sense strand polynucleotide corresponding to a target gene, and an antisense strand polynucleotide having a nucleotide sequence complementary to the sense strand polynucleotide, and has a single-stranded structure in which the 5'-end of the antisense strand and the 3'-end of the sense strand are linked via a linker structurally defined by a structural formula shown below to form a phosphodiester structure at each of these ends, the single-stranded structure being polynucleotide-3'-P(=O)(OH)—[linker]-P(=O)(OH)-5'-polynucleotide, is also referred to as a "3L5-polynucleotide".

The 3L5-polynucleotide is preferably a polynucleotide having a structure represented by the following formula:

[Formula 20]

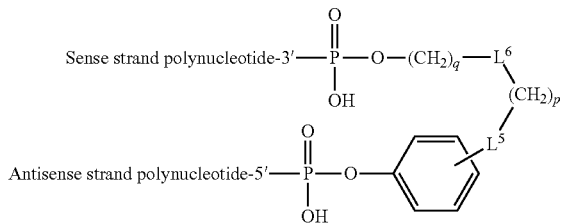

wherein
p represents an integer of 0 to 4,
q represents an integer of 4 to 10,
$L^5$ represents a single bond or —O—,
$L^6$ represents —(C=O)—NH— or —NH—(C=O)— starting from the bond with $(CH_2)_p$,
$L^5$ is bonded to the benzene ring at the para or meta position, and provided that if $L^5$ is —O—, then p represents an integer of 1 to 4.

Furthermore, the following combinations are more preferable:

the sum of p and q is an integer of 4 or larger, $L^5$ is a single bond, $L^6$ is —(C=O)—NH—, and $L^5$ is bonded to the benzene ring at the para position;

the sum of p and q is an integer of 8 or larger, $L^5$ is a single bond, $L^6$ is —(C=O)—NH—, and $L^5$ is bonded to the benzene ring at the para position;

p is 0 or 2, q is an integer of 6 or larger, $L^5$ is a single bond, $L^6$ is —(C=O)—NH—, and $L^5$ is bonded to the benzene ring at the para position;

p is 0 or 2, q is 6 or 8, $L^5$ is a single bond, $L^6$ is —(C=O)—NH—, and $L^5$ is bonded to the benzene ring at the para position;

p is 0 or 2, q is 8, $L^5$ is a single bond, $L^6$ is —(C=O)—NH—, and $L^5$ is bonded to the benzene ring at the para position; or p is 2, q is 8, $L^5$ is a single bond, $L^6$ is —(C=O)—NH—, and $L^5$ is bonded to the benzene ring at the para position.

In the present specification, the term "complementary nucleotides" refers to nucleotides whose base moieties are complementary to each other and refers, for example, to nucleotides complementary to each other by way of adenine and thymine, guanine and cytosine, guanine and 5-methylcytosine, and adenine and uracil as base moieties.

In the present specification, the "complementary nucleotide sequence" includes a nucleotide sequence consisting of nucleotides, all of which are complementary to a target nucleotide sequence, and also includes a nucleotide sequence forming base pairs with nucleotides in a polynucleotide, albeit with one or more nucleotides that are not complementary.

In the present specification, the double-stranded structure of the polynucleotide refers to a double-stranded structure formed by Watson-Crick base pairs between the respective complementary nucleotide sequences of two polynucleotides and a double-stranded structure (within a single-stranded polynucleotide) formed by Watson-Crick base pairs between complementary sequences within the single-stranded polynucleotide.

In the present specification, the 3L5-polynucleotide is a single-stranded polynucleotide forming a double-stranded structure by Watson-Crick base pairs formed between complementary nucleotides, though not all the nucleotides in the polynucleotide may form Watson-Crick base pairs.

In the present specification, of polynucleotides constituting the 3L5-polynucleotide, a strand comprising a nucleotide sequence identical to a target gene is called a passenger strand or sense strand corresponding to the target gene, whereas a strand comprising a nucleotide sequence complementary to the target gene is called a guide strand or antisense strand against the target gene. The antisense strand against the target gene has a nucleotide sequence complementary to the mRNA of the target gene.

In the present specification, the phrase "having a nucleotide sequence identical to a target gene" refers to having a sequence identical to at least a partial nucleotide sequence of the target gene. It includes a completely identical sequence and also includes a substantially identical sequence as long as the resulting 3L5-polynucleotide has an RNA interference effect and/or gene expression inhibitory effect on the target gene. The phrase "having a nucleotide sequence complementary to the target gene" refers to having a sequence complementary to at least a partial nucleotide sequence of the target gene. It includes a completely complementary sequence and also includes a substantially complementary identical sequence as long as the resulting 3L5-polynucleotide has RNA interference effect and/or gene expression inhibitory effect on the target gene. Moreover, when the target gene is known to have SNPs or the like, a sequence having these variations is also included as an identical nucleotide sequence. In the present specification, a polynucleotide that comprises a nucleotide sequence complementary to a target gene and has RNA interference effect and/or gene expression inhibitory effect on the target gene is referred to as a polynucleotide corresponding to the target gene.

The nucleotide sequence of the 3L5-polynucleotide corresponding to the target gene is not particularly limited as long as it has RNA interference effect and/or gene expression inhibitory effect on the target gene. For example, it can be determined by determining the sequences of sense and antisense strands on the basis of a sequence predicted to have RNA interference effect on the target gene using computer software (e.g., GENETYX (registered trademark): manufactured by GENETYX CORPORATION), and can also be determined by further confirming the RNA interference effect and/or gene expression inhibitory effect of a 3L5-polynucleotide prepared on the basis of the selected sequence.

In the present specification, the term "gene expression inhibitory effect" includes the effect of completely inhibiting gene expression and also includes the effect of reducing gene expression, compared with a control. Moreover, gene silencing is also included within the term "gene expression inhibitory effect". Moreover, in the present specification, the term "gene expression inhibitory effect" is used with the same meaning as the term "gene expression inhibitory activity".

The RNA interference effect and/or the gene expression inhibitory effect can be confirmed by a method usually performed by those skilled in the art and can be confirmed, for example, by: administering a 3L5-polynucleotide corresponding to a target gene to cells expressing the target gene; after a lapse of the given time, quantifying a protein, which is a translation product of the target gene, by Western blot analysis; and comparing the protein expression level with a control. Moreover, the RNA interference effect and/or the gene expression inhibitory effect can also be confirmed by measuring in real time the expression level of the target gene after administration of the single-stranded polynucleotide corresponding to the target gene by the technique of real-time PCR.

A polynucleotide having a sequence identical or substantially identical to at least a partial nucleotide sequence of the target gene is a polynucleotide having a sequence identical or substantially identical to any 18-nucleotide or more sequence in the nucleotide sequence of the target gene. In this context, the "substantially identical sequence" refers to a sequence having 70% or higher, preferably 80% or higher, more preferably 90% or higher homology, to the nucleotide sequence of the target gene. The homology of the nucleotide sequence can be calculated using gene analysis software known in the art such as BLAST (registered trademark).

In the item <223> for each sequence in the Sequence Listing attached to the present specification, "cm" represents 2'-O-methylcytidine; "um" represents 2'-O-methyluridine; and "gm" represents 2'-O-methylguanosine.

2. 3L5-polynucleotide

The respective chain lengths of the sense and antisense strands constituting the 3L5-polynucleotide according to the present invention may be any length from 18 nucleotides to the full length of the open reading frame (ORF) of the target gene as long as the resulting 3L5-polynucleotide has an RNA interference effect and/or a gene expression inhibitory effect. The sense strand is preferably 18 to 21 nucleotides, more preferably 18 or 19 nucleotides, in chain length. The antisense strand is preferably 19 to 21 nucleotides, more preferably 21 nucleotides, in chain length. The 3L5-polynucleotide does not have to be a double-stranded structure as a whole and includes those partially overhanging at the 5' and/or 3'-ends. The overhanging end has 1 to 5 nucleotides, preferably 1 to 3 nucleotides, more preferably 2 nucleotides. Moreover, the most preferable examples of the 3L5-polynucleotide include a polynucleotide having a structure in which the 3'-end of the antisense strand polynucleotide overhangs by 2 nucleotides (overhang structure), and having 18 base pairs.

The 3L5-polynucleotide has at least any one property selected from the following (a) to (h):

(a) having an RNA interference effect and/or a gene expression inhibitory effect on the target gene;

(b) being resistant to RNase and having an RNA interference effect and/or a gene expression inhibitory effect on the target gene;

(c) being resistant to phosphatase and having an RNA interference effect and/or a gene expression inhibitory effect on the target gene;

(d) being resistant to exonuclease and having an RNA interference effect and/or a gene expression inhibitory effect on the target gene;

(e) being resistant to RNase, phosphatase, and exonuclease and having an RNA interference effect and/or a gene expression inhibitory effect on the target gene;

(f) having an antisense strand that is resistant to phosphatase and having an RNA interference effect and/or a gene expression inhibitory effect on the target gene;

(g) having an antisense strand that is resistant to exonuclease and having an RNA interference effect and/or a gene expression inhibitory effect on the target gene; and (h) having an antisense strand that is resistant to 5'-3'-exonuclease and having an RNA interference effect and/or a gene expression inhibitory effect on the target gene.

2-1.

One example of the 3L5-polynucleotide can include a polynucleotide, a feature of which is that the polynucleotide is derived from a double-stranded polynucleotide comprising a sense strand polynucleotide corresponding to a target gene, and an antisense strand polynucleotide having a nucleotide sequence complementary to the sense strand polynucleotide, and has a structure in which the 5'-end of the antisense strand and the 3'-end of the sense strand are linked via a linker structurally defined by a structural formula shown below to form a phosphodiester structure at each of these ends, the structure being the following structure: polynucleotide-3'-P(=O)(OH)-[linker]-P(=O)(OH)-5'-polynucleotide wherein "polynucleotide-3'" represents the structure of the polynucleotide without a hydrogen atom on its 3'-terminal hydroxy group, and "5'-polynucleotide" represents the structure of the polynucleotide without a hydrogen atom on its 5'-terminal hydroxy group.

A further example of the 3L5-polynucleotide can include an isolated RNA molecule having a double-stranded structure comprising sense and antisense strands 18 to 23 bases long, each of which is 18 to 23 bases in length and at least one of which has a 3'-overhang consisting of 1 to 3 bases, wherein the RNA molecule is an RNA molecule that is capable of target-specific RNA interference and has one strand consisting of a sequence 100% identical to the predetermined target mRNA molecule except for the 3'-overhang, the target mRNA molecule being present in a cell or an organism, and wherein the RNA molecule is a polynucleotide having a structure in which the 5'-end of the antisense strand and the 3'-end of the sense strand are linked via a linker to form a phosphodiester structure at each of these ends.

A further example of the 3L5-polynucleotide can include a polynucleotide or a salt thereof, the polynucleotide comprising a sense strand polynucleotide consisting of a polynucleotide represented by the following formula (II) and an antisense strand polynucleotide consisting of a polynucleotide represented by the following formula (III), having a structure in which the 5'-end of the antisense strand and the 3'-end of the sense strand are linked via a linker to form a phosphodiester structure at each of these ends, and further having the following features (a) to (d):

 (II) and

 (III), (a) γ represents an RNA, β represents a 2'-OMeRNA, and λ and ν each represent a DNA;

(b) t and u identically or differently represent any integer from 0 to 5;

(c) $(\gamma\text{-}\beta)_9\text{-}\gamma$ in the polynucleotide represented by the formula (II) has a nucleotide sequence identical to the target gene; and (d) $(\gamma\text{-}\beta)_9\text{-}\gamma$ in the formula (II) and $\beta\text{-}(\gamma\text{-}\beta)_9$ in the formula (III) have nucleotide sequences complementary to each other.

γ, β, λ, and ν each represent a nucleoside unit. The line between the nucleosides represents a phosphodiester bond or a phosphorothioate bond. The nucleoside unit refers to an N-glucosyl form of a nucleic-acid base (e.g., the "natural nucleoside" or "sugar-modified nucleoside" described above), which is a constituent unit of the polynucleotide.

A further example of the 3L5-polynucleotide can include a polynucleotide or a salt thereof, the polynucleotide comprising a sense strand polynucleotide consisting of a polynucleotide represented by the following formula (IV) and an antisense strand polynucleotide consisting of a polynucleotide represented by the following formula (V), having a structure in which the 5'-end of the antisense strand and the 3'-end of the sense strand are linked via a linker to form a phosphodiester structure at each of these ends, and further having the following features (a) to (d)

 (IV) and

 (V), (a) α and β differently represent a DNA or a 2'-OMeRNA, δ and λ identically or differently represent a DNA or a 2'-OMeRNA, and ν identically or differently represents any nucleotide selected from a DNA, an RNA, and a 2'-OMeRNA;

(b) p represents an integer of 0 or 1, t is 0 when p is 0 and represents any integer from 0 to 5 when p is 1, s represents an integer of 0 or 1, and u represents any integer from 0 to 5;

(c) $(\alpha\text{-}\beta)_9\text{-}\alpha_p$ in the polynucleotide represented by the formula (IV) has a nucleotide sequence identical to the target gene; and (d) $(\alpha\text{-}\beta)_9$ in the formula (IV) and $(\alpha\text{-}\beta)_9$ in the formula (V) have nucleotide sequences complementary to each other.

α, β, δ, and λ each represent a nucleoside unit. The line between the nucleosides represents a phosphodiester bond or a phosphorothioate bond. The nucleoside unit refers to an N-glucosyl form of a nucleic-acid base (e.g., the "natural nucleoside" or "sugar-modified nucleoside" described above), which is a constituent unit of the polynucleotide.

A further example of the 3L5-polynucleotide can include a polynucleotide or a salt thereof, the polynucleotide comprising a sense strand polynucleotide consisting of a polynucleotide represented by the following formula (VI) and an antisense strand polynucleotide consisting of a polynucleotide represented by the following formula (VII), having a structure in which the 5'-end of the antisense strand and the 3'-end of the sense strand are linked via a linker to form a phosphodiester structure at each of these ends, and further having the following features (a) to (d):

 (VI) and

 (VII), (a) α and β differently represent a DNA or a 2'-OMeRNA, δ and a identically or differently represent a DNA or a 2'-OMeRNA, and ν identically or differently represents any nucleotide selected from a DNA, an RNA, and a 2'-OMeRNA;

(b) p represents an integer of 0 or 1, t is 0 when p is 0 and represents any integer from 0 to 5 when p is 1, s represents an integer of 0 or 1, and u represents any integer from 0 to 5;

(c) $\beta\text{-}(\alpha\text{-}\beta)_8\text{-}\alpha_p$ in the polynucleotide represented by the formula (VI) has a nucleotide sequence identical to the target gene; and (d) $(\alpha\text{-}\beta)_8$ in the formula (VI) and $(\alpha\text{-}\beta)_8$ in the formula (VII) have nucleotide sequences complementary to each other.

A further example of the 3L5-polynucleotide can include the polynucleotide or a salt thereof, the polynucleotide comprising a sense strand polynucleotide consisting of a polynucleotide represented by the following formula (VIII) and an antisense strand polynucleotide consisting of a polynucleotide represented by the following formula (IX), having a structure in which the 5'-end of the antisense strand and the 3'-end of the sense strand are linked via a linker to form a phosphodiester structure at each of these ends, and further having the following features (a) to (c):

 (VIII) and

 (IX), (a) α is a DNA, and β is a 2'-OMeRNA;

(b) $\beta\text{-}(\alpha\text{-}\beta)_9$ in the polynucleotide represented by the formula (IX) has a nucleotide sequence complementary to the target gene; and (c) $(\alpha\text{-}\beta)_9$ in the formula (VIII) and $(\alpha\text{-}\beta)_9$ in the formula (IX) have nucleotide sequences complementary to each other.

The 3L5-polynucleotide also includes a polynucleotide in which arbitrary 1 to 4 residues in the 3L5-polynucleotide are substituted by other sugar-modified nucleotides as long as the polynucleotide has an RNA interference effect and/or a gene expression inhibitory effect.

The sugar-modified nucleotide encompasses all manner of sugar modification known in the technical field to which the present invention belongs. The sugar-modified nucleotide can retain every heterocyclic base site and internucleoside bond and further includes sugar-modified nucleotides different from the sugar modifications described above. The group of sugar-modified nucleotides includes 2'-modified nucleosides, 4'-thio-modified nucleosides, 4'-thio-2'-modified nucleosides, and bicyclic sugar-modified nucleosides.

The 2'-modified nucleosides are, for example, halo, allyl, amino, azide, O-allyl, O—$C_1$-$C_{10}$ alkyl, $OCF_3$, O—$(CH_2)_2$—O—$CH_3$, 2'-O$(CH_2)_2SCH_3$, O—$(CH_2)_2$—O—$N(R_m)(R_n)$, and O—$CH_2$—C(=O)—$N(R_m)(R_n)$, wherein $R_m$ and $R_n$ are each individually H, an amino protective group, or substituted or unsubstituted $C_1$-$C_{10}$ alkyl. A preferable 2'-modification is —F, —$OCH_3$, or —O—$(CH_2)_2$—O—$CH_3$, more preferably —$OCH_3$.

Examples of the 4'-thio-modified nucleosides can include β-D-ribonucleosides in which the 4'-oxygen atom has been substituted by a sulfur atom (Hoshika, S. et al. FEBS Lett. 579, p. 3115-3118, (2005); Dande, P. et al. J. Med. Chem. 49, p. 1624-1634 (2006); and Hoshika, S. et al. Chem Bio Chem. 8, p. 2133-2138, (2007)).

Examples of the 4'-thio-2'-modified nucleosides can include 4'-thio-2'-modified nucleosides retaining 2'-H or 2'-O-methyl (Matsugami, et al. Nucleic Acids Res. 36, 1805 (2008)).

Examples of the bicyclic sugar-modified nucleosides can include nucleosides retaining the second ring formed by bridging two atoms of the ribose ring. Examples of such nucleosides can include: 2',4'-BNAs/LNAs (bridged nucleic acids/locked nucleic acids) in which the 2'-oxygen atom and the 4'-carbon atom are bridged by a methylene chain (Obika, S. et al. Tetrahedron Lett., 38, p. 8735-(1997); Obika, S. et al., Tetrahedron Lett., 39, p. 5401-(1998); A. A. Koshkin, A. A. et al. Tetrahedron, 54, p. 3607 (1998); and Obika, S. Bioorg. Med. Chem., 9, p. 1001 (2001).); and ENAs (2'-O,4'-C-ethylene-bridged nucleic acids) bridged by an ethylene chain longer by one carbon than the methylene chain of the 2',4'-BNA/LNA (Morita, K. et al. Bioorg. Med. Chem. Lett., 12, p. 73 (2002); and Morita, K. et al. Bioorg. Med. Chem., 11, p. 2211 (2003).).

When arbitrary 1 to 4 2'-OMeRNA residues in the 3L5-polynucleotide containing 2'-OMeRNA are substituted by sugar-modified nucleotides, out of the above sugar-modified nucleotides, the more preferable sugar-modified nucleotides are identically or differently an ENA or a 2',4'-BNA/LNA.

The 3L5-polynucleotide also includes a polynucleotide in which 1 to 4 DNA residues in the polynucleotide are identically or differently substituted by an RNA, an ENA, or a 2',4'-BNA/LNA.

2-2 Method for Synthesizing Sense Strand in 3L5-Polynucleotide

The method for preparing the polynucleotide constituting the 3L5-polynucleotide is not particularly limited as long as a desired polynucleotide can be synthesized, and a known chemical synthesis method can be used, for example, a phosphotriester, phosphoramidite, or H-phosphonate method. For example, it can be synthesized using a commercially available nucleic acid synthesizer and commercially available reagents used in DNA/RNA synthesis.

2-3 Method for Synthesizing 3L5-Polynucleotide

The method for manufacturing the 3L5-polynucleotide is not limited as long as the 3L5-polynucleotide can be synthesized. It can be synthesized by, for example, the following method:

2-3-1 Method A
2-3-1-1 Step A-1

The outline of Step A-1 is shown in FIG. 1.

The present step is the step of using a polymer support (1) bound with the desired nucleosides (referred to as Tr$^1$-O—Y-CPG in Step A 1, wherein CPG represents a polymer support having a linker capable of binding to the polynucleotide, Y represents a nucleoside unit, with a protected amino group on the nucleobase moiety, without 5'- and 3'-hydroxy groups and Tr$^1$ represents a protective group for the hydroxy group) to produce a compound (2) (referred to as HO—W$^1$-Y-CPG in Step A-1, wherein W$^1$-Y represents a protected polynucleotide without 5'-terminal and 3'-terminal hydroxy groups, which is an oligonucleotide analog consisting of the desired nucleotide sequence.

Tr$^1$ is not particularly limited as long as it is a protective group for the hydroxy group that can be deprotected without eliminating the protective group in the nucleic acid. Examples thereof can include a 4-methoxytrityl group, a 4,4'-dimethoxytrityl group, a pixyl group, a trityl group, a levulinyl group, and a bis(trimethylsilyloxy)(cyclohexyloxy)silyl group. A 4-methoxytrityl group or a 4,4'-dimethoxytrityl group is preferable.

The protective group for the amino group on the base moiety of the nucleic acid is not particularly limited as long as it is usually applicable. Examples thereof include a benzoyl group, an isobutyryl group, an acetyl group, a phenoxyacetyl group, a 4-(t-butyl)phenoxyacetyl group, an allyloxycarbonyl group, and a p-nitrophenylethylcarbonyl group.

Examples of CPG include controlled pore glass, long chain alkylamino controlled pore glass (Oligonucleotide synthesis Edited by M. J. Gait, IRL Press, 1984, pp. 84-115), and polystyrene beads (Tetrahedron Lett. 34, 3373 (1994)). Another example of CPG includes a polymer support having an aminoalkyl group such as an aminopropyl group or an aminohexyl group.

Examples of the linker capable of binding to the polynucleotide include a succinic acid linker —OC(=O)—CH$_2$CH$_2$C(=O)— that forms an ester bond via the oxygen atom to the 3' position of Y and forms an amide bond via the other carboxylic acid group of the succinic acid to the amino group on the polymer support. Examples of the linker other than the succinic acid linker include sarcosine (—OC(=O)—CH$_2$CH$_2$C(=O)—) and oxalic acid (—OC(=O)C(=O)—) linkers.

Examples of commercially available Tr$^1$-O—Y-CPG wherein Tr$^1$ is 4,4'-dimethoxytrityl group, and CPG has a succinic acid linker —OC(=O)—CH$_2$CH$_2$C(=O)— that forms an ester bond via the oxygen atom to the 3' position of Y and forms an amide bond via the other carboxylic acid group of the succinic acid to the amino group on the polymer support include 2'-OMe-A-RNA-CPG (20-3600-10), 2'-OMe-C-RNA-CPG (20-3610-10), 2'-OMe-G-RNA-CPG (20-3621-10), 2'-OMe-U-RNA-CPG (20-3630-10), Bz-A-RNA-CPG (20-3303-10), Ac-C-RNA-CPG (20-3315-10), iPr-Pac-G-RNA-CPG (20-3324-10), U-RNA-CPG (20-3330-10), dA-CPG (20-2000-10), dC-CPG (20-2010-10), dG-CPG (20-2020-10), and dT-CPG (20-2030-10) from Glen Research Corp.

The compound (2) is produced by a usual phosphoramidite method using an automatic DNA synthesizer and a phosphoramidite reagent, etc., necessary for producing the compound (2). The oligonucleotide analog having the desired nucleotide sequence can be synthesized according to a method described in the literature (Nucleic Acids Research, 12, 4539 (1984)) using a DNA synthesizer, for example, model 392 (manufactured by PerkinElmer Inc.), which is based on the phosphoramidite method.

Moreover, when the oligonucleotide analog is converted, if desired, to a thioate form, a thioate derivative can be obtained according to methods described in the literature (Tetrahedron Letters, 32, 3005 (1991); and J. Am. Chem. Soc., 112, 1253 (1990)) using sulfur or a reagent such as tetraethylthiuram disulfide (TETD, Applied Biosystems), Beaucage reagent, or a phenylacetyl disulfide/pyridine-acetonitrile (1:1 v/v) solution (Ravikumar, V. T. et al., Bioorg. Med. Chem. Lett. (2006) 16, p. 2513-2517).

2-3-2 Method C

Figure 2:
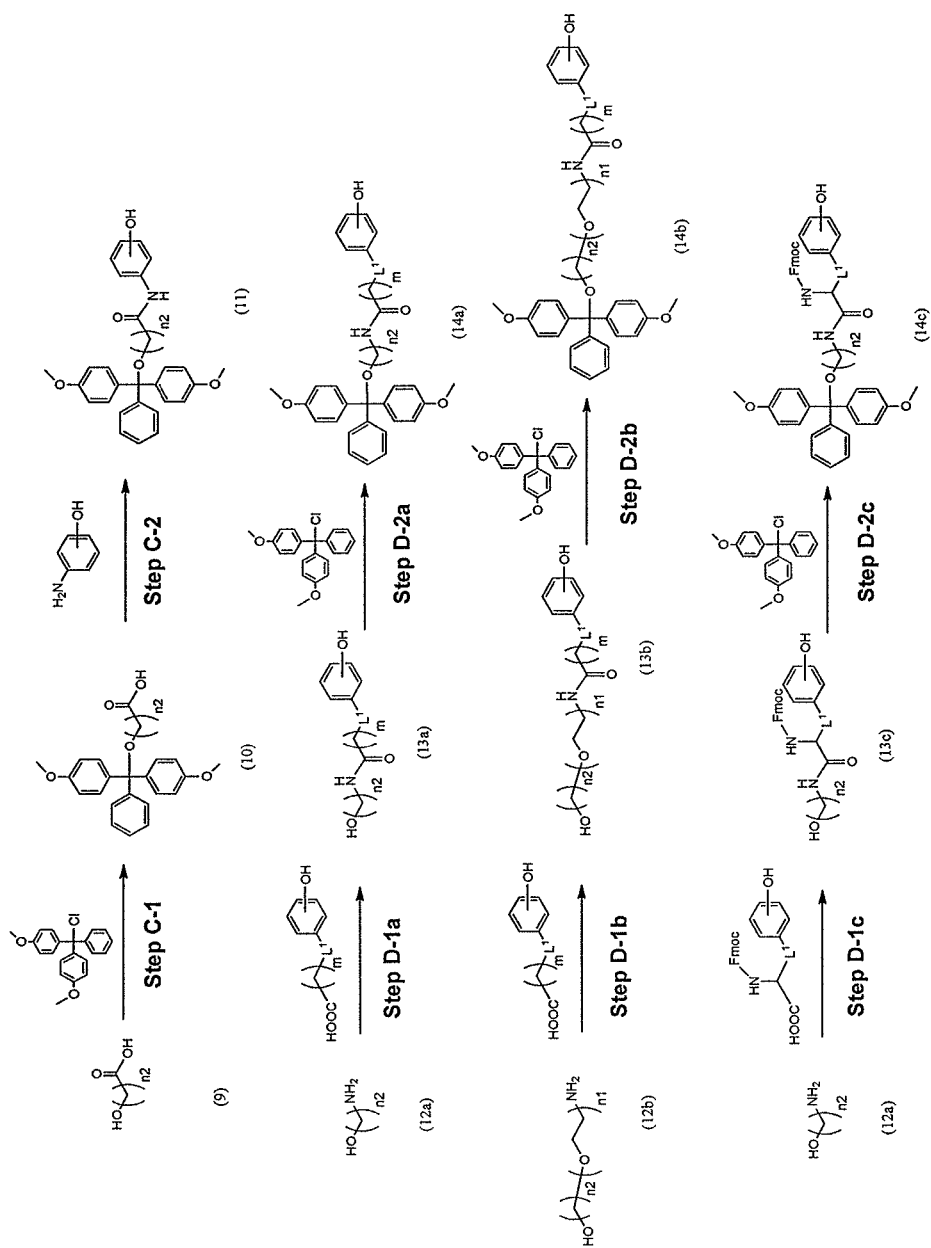
FIG. 2 is a diagram showing the outlines of Methods C and D.

The outline of Method C is shown in FIG. 2.

2-3-2-1 Step C-1

The present step is the step of reacting the compound (9) with a protecting reagent (preferably, dimethoxytrityl chloride) removable under acidic conditions, in the presence of a deoxidizer in an inert solvent to obtain a compound (10) with a protected hydroxy group on the compound (9).

The solvent used is not particularly limited as long as it does not inhibit the reaction and dissolves starting materials to some extent. Examples thereof can include: aromatic hydrocarbons such as benzene, toluene, and xylene; halogenated hydrocarbons such as methylene chloride and chloroform; ethers such as ether, tetrahydrofuran, dioxane, and dimethoxyethane; amides such as dimethylformamide, dimethylacetamide, and hexamethylphosphoric triamide; sulfoxides such as dimethyl sulfoxide; ketones such as acetone and methyl ethyl ketone; heterocyclic amines such as pyridine; and nitriles such as acetonitrile. Preferable examples thereof include heterocyclic amines (particularly, pyridine).

Examples of the protecting reagent used include trityl halides such as trityl chloride, monomethoxytrityl chloride, dimethoxytrityl chloride, and trimethoxytrityl chloride. Monomethoxytrityl chloride or dimethoxytrityl chloride is preferable.

The deoxidizer used is not particularly limited as long as it neither inhibits the reaction nor decomposes products and starting materials. Aromatic amines such as pyridine and dimethylaminopyridine are preferable.

The reaction temperature and time differ depending on the types of the protecting reagent and the deoxidizer used. In the case of using dimethoxytrityl chloride as the protecting reagent and using pyridine both as the solvent and as the deoxidizer, the reaction is performed at room temperature for 2 hours.

After completion of the reaction, the compound of interest is collected from the reaction mixture according to a standard method. The compound of interest is obtained, for example, by: appropriately neutralizing the reaction mixture, or removing insoluble matter, if any, by filtration; then adding water and a water-immiscible organic solvent such as ethyl acetate; after washing with water, separating the organic layer containing the compound of interest; drying the organic layer over anhydrous magnesium sulfate or the like; and then distilling off the solvent. The obtained compound of interest can be further purified, if necessary, by a standard method, for example, recrystallization, reprecipitation, or chromatography.

2-3-2-2 Step C-2

The present step is the step of reacting the carboxyl group of the compound (10) with phenol having an amino group in an inert solvent to form a compound (11) having an amide bond.

The solvent used is not particularly limited as long as it does not inhibit the reaction. Examples thereof include: aromatic hydrocarbons such as benzene, toluene, and xylene; halogenated hydrocarbons such as methylene chloride, chloroform, carbon tetrachloride, dichloroethane, chlorobenzene, and dichlorobenzene; esters such as ethyl formate, ethyl acetate, propyl acetate, butyl acetate, and diethyl carbonate; ketones such as acetone, methyl ethyl ketone, methyl isobutyl ketone, isophorone, and cyclohexanone; nitro compounds such as nitroethane and nitrobenzene; nitriles such as acetonitrile and isobutyronitrile; amides such as formamide, dimethylformamide (DMF), dimethylacetamide, and hexamethylphosphoric triamide; and sulfoxides such as dimethyl sulfoxide and sulfolane. Halogenated hydrocarbons (particularly, methylene chloride) or amides (particularly, dimethylformamide) are preferable.

Examples of the phenol used can include 4-aminophenol and 3-aminophenol. 4-aminophenol is preferable.

Examples of an amide-forming reagent used include: N-hydroxy compounds such as N-hydroxysuccinimide, 1-hydroxybenzotriazole, and N-hydroxy-5-norbornene-2,3-dicarboximide; diimidazole compounds such as 1,1'-oxalyldiimidazole and N,N'-carbonyldiimidazole; disulfide compounds such as 2,2'-dipyridyl disulfide; succinic acid compounds such as N,N'-disuccinimidyl carbonate; phosphinic chloride compounds such as N,N'-bis(2-oxo-3-oxazolidinyl)phosphinic chloride; oxalate compounds such as N,N'-disuccinimidyl oxalate (DSO), N,N'-diphthalimidyl oxalate (DPO), N,N'-bis(norbornenylsuccinimidyl)oxalate (BNO), 1,1'-bis(benzotriazolyl)oxalate (BBTO), 1,1'-bis(6-chlorobenzotriazolyl)oxalate (BCTO), and 1,1'-bis(6-trifluoromethylbenzotriazolyl)oxalate (BTBO); and carbodiimides such as dicyclohexylcarbodiimide (DCC) and 1-(3-dimethylaminopropyl)-3-ethylcarbodiimide (EDC). Particularly, diimidazole compounds or carbodiimides (particularly EDC) are preferable.

1-hydroxybenzotriazole (HOBT) may be added as a reaction auxiliary reagent.

The reaction temperature and time differ depending on the types of the amide-forming reagent and the solvent used and are 0° C. to 100° C. for 5 to 50 hours. Particularly, in the case of using 4-aminophenol and EDC in methylene chloride, the reaction is performed at room temperature for 18 hours.

After completion of the reaction, the compound of interest is collected from the reaction mixture according to a standard method. The compound of interest is obtained, for example, by: appropriately neutralizing the reaction mixture, or removing insoluble matter, if any, by filtration; then adding water and a water-immiscible organic solvent such as ethyl acetate; after washing with water, separating the organic layer containing the compound of interest; drying the organic layer over anhydrous magnesium sulfate or the like; and then distilling off the solvent. The obtained compound of interest can be further purified, if necessary, by a standard method, for example, recrystallization, reprecipitation, or chromatography.

2-3-3 Method D

The outline of Method D is shown in FIG. 2. In the diagram, n1, n2, m, and $L^1$ are as defined above. Specifically, m represents an integer of 0 to 4, and $L^1$ represents a single bond or —O—.

2-3-3-1 Step D-1a

The present step is the step of reacting the amino group of the compound (12a) with phenol having a carboxyl group in an inert solvent to form a compound (13a) having an amide bond.

Examples of the phenol used can include 3-hydroxyphenylacetic acid, 4-hydroxyphenylacetic acid, 3-(3-hydroxyphenyl)propionic acid, 3-(4-hydroxyphenyl)propionic acid, 4-(3-hydroxyphenyl)valeric acid, 4-(4-hydroxyphenyl)valeric acid, 3-hydroxyphenoxyacetic acid, and 4-hydroxyphenoxyacetic acid. 3-(4-hydroxyphenyl)propionic acid is preferable.

The present step can be performed in the same way as for step C-2.

2-3-3-2 Step D-2a

The present step is the step of reacting the compound (13a) with a protecting reagent (preferably, dimethoxytrityl chloride) removable under acidic conditions, in the presence of a deoxidizer in an inert solvent to obtain a compound (14a) with a protected hydroxy group on the compound (13a).

The present step can be performed in the same way as for step C-1.

2-3-3-3 Step D-1b

The present step is the step of reacting the amino group of the compound (12b) with phenol having a carboxyl group in an inert solvent to form a compound (13b) having an amide bond.

Examples of the phenol used can include 3-hydroxyphenylacetic acid, 4-hydroxyphenylacetic acid, 3-(3-hydroxyphenyl)propionic acid, 3-(4-hydroxyphenyl)propionic acid, 4-(3-hydroxyphenyl)valeric acid, 4-(4-hydroxyphenyl)valeric acid, 3-hydroxyphenoxyacetic acid, and 4-hydroxyphenoxyacetic acid. 3-(4-hydroxyphenyl)propionic acid is preferable.

The present step can be performed in the same way as for step C-2.

2-3-3-4 Step D-2b

The present step is the step of reacting the compound (13b) with a protecting reagent (preferably, dimethoxytrityl chloride) removable under acidic conditions, in the presence of a deoxidizer in an inert solvent to obtain a compound (14b) with a protected hydroxy group on the compound (13b).

The present step can be performed in the same way as for step C-1.

2-3-3-5 Step D-1c

The present step is the step of reacting the amino group of the compound (12a) with phenol having a carboxyl group in an inert solvent to form a compound (13c) having an amide bond.

Examples of the phenol used can include N-[(9H-fluoren-9-ylmethoxy)carbonyl]-L-tyrosine.

The present step can be performed in the same way as for step C-2.

2-3-3-6 Step D-2c

The present step is the step of reacting the compound (13c) with a protecting reagent (preferably, dimethoxytrityl chloride) removable under acidic conditions, in the presence of a deoxidizer in an inert solvent to obtain a compound (14c) with a protected hydroxy group on the compound (13c).

The present step can be performed in the same way as for step C-1.

2-3-4 Method E

Figure 3:
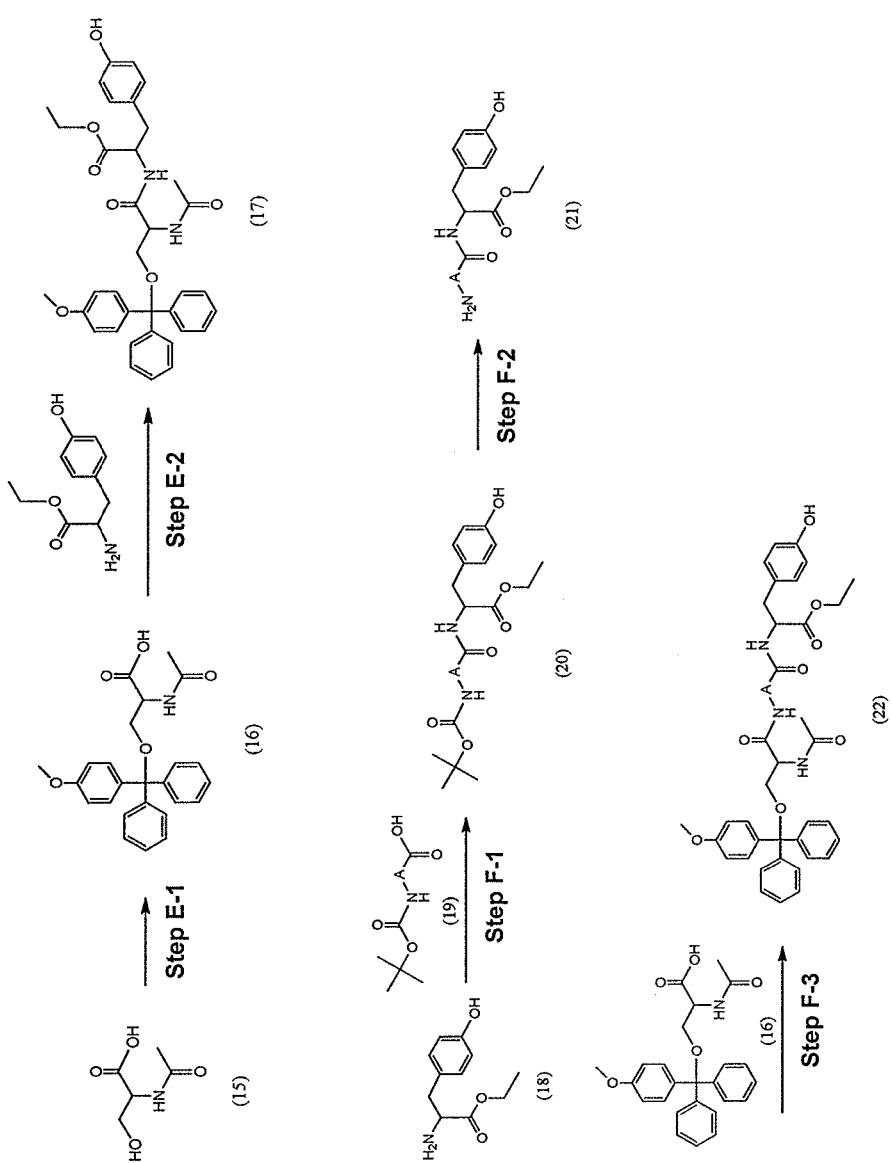
FIG. 3 is a diagram showing the outlines of Methods E and F.

The outline of Method E is shown in FIG. 3.

2-3-4-1 Step E-1

The present step is the step of reacting the compound (15) with a protecting reagent (preferably, monomethoxytrityl chloride) removable under acidic conditions, in the presence of a deoxidizer in an inert solvent to obtain a compound (16) with a protected hydroxy group on the compound (15).

The present step can be performed in the same way as for step C-1.

2-3-4-2 Step E-2

The present step is the step of reacting the carboxyl group of the compound (16) with tyrosine ester in an inert solvent to form a compound (17) having an amide bond.

Examples of the tyrosine ester used can include tyrosine methyl ester and tyrosine ethyl ester. Tyrosine ethyl ester is preferable.

The present step can be performed in the same way as for step C-2.

The outline of Method F is shown in FIG. 3. In the diagram, A represents —CH$_2$—, —CH(CH$_3$)—, —CH$_2$CH$_2$, —CH[CH$_2$CH(CH$_3$)$_2$]—, or —CH[CH(CH$_3$)CH$_2$CH$_3$]—.

2-3-5-1 Step F-1

The present step is the step of reacting the amino group of the compound (18) with an amino acid (19) having an amino group protected with a t-Boc group in an inert solvent to form a compound (20) having an amide bond.

Examples of the type of the amino acid protected with a t-Boc group can include glycine, alanine, β-alanine, leucine, and isoleucine. Glycine, alanine, or β-alanine is preferable.

The present step can be performed in the same way as for step C-2.

2-3-5-2 Step F-2

The present step is the step of reacting the compound (20) with a deprotecting reagent for selective removal of the protective group in the amino group in an inert solvent to produce a compound (21).

Preferable examples of the solvent used include: aromatic hydrocarbons such as benzene, toluene, and xylene; halogenated hydrocarbons such as methylene chloride, chloroform, carbon tetrachloride, dichloroethane, chlorobenzene, and dichlorobenzene; esters such as ethyl formate, ethyl acetate, propyl acetate, butyl acetate, and diethyl carbonate; ethers such as diethyl ether, diisopropyl ether, tetrahydrofuran, dioxane, dimethoxyethane, and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol, and methylcellosolve; ketones such as acetone, methyl ethyl ketone, methyl isobutyl ketone, isophorone, and cyclohexanone; nitro compounds such as nitroethane and nitrobenzene; nitriles such as acetonitrile and isobutyronitrile; amides such as formamide, dimethylformamide, dimethylacetamide, and hexamethylphosphoric triamide; and sulfoxides such as dimethyl sulfoxide and sulfolane. More preferable examples thereof include alcohols (particularly, methanol and ethanol), methylene chloride, and, in the case of using acetic acid as the deprotecting reagent, a mixed solution of acetic acid and water.

The deprotecting reagent used is not particularly limited as long as it is usually applicable. In the case of using a t-Boc group as the protective group, examples of the deprotecting reagent include Lewis acids such as acetic acid, dichloroacetic acid, trifluoroacetic acid, hydrochloric acid, and zinc bromide. Acetic acid, dichloroacetic acid, or trifluoroacetic acid is preferable.

The reaction temperature differs depending on reagents, starting materials, solvents, etc. used and is usually −10 to 100° C., preferably 0 to 50° C.

The reaction time differs depending on starting materials used, reagents, reaction temperature, etc., and is usually 1 minute to 50 hours, preferably 1 minute to 24 hours.

After completion of the reaction, the compound of interest is collected from the reaction mixture according to a standard method.

2-3-5-3 Step F-3

The present step is the step of reacting the amino group of the compound (21) with a compound (16) in an inert solvent to form a compound (22) having an amide bond.

The present step can be performed in the same way as for step C-2.

2-3-6 Method G

Figure 4:
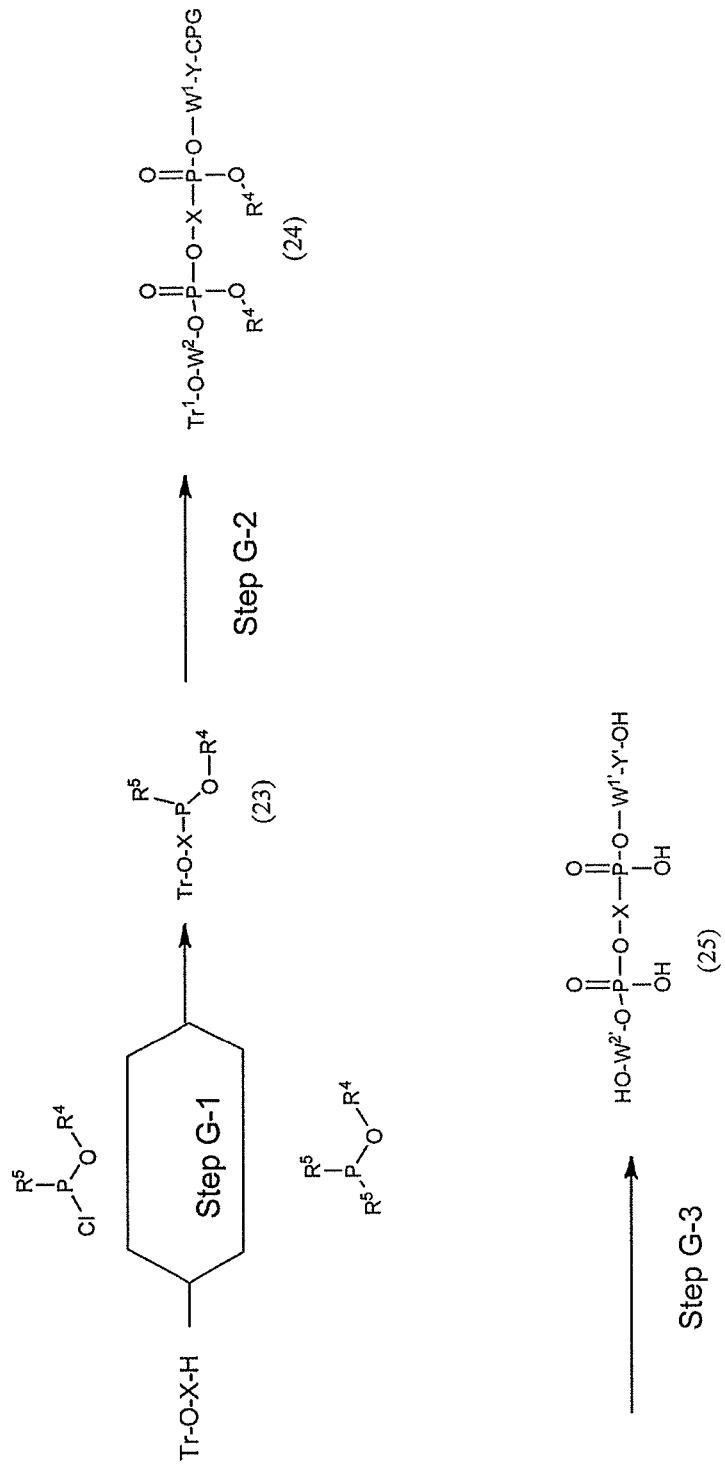
FIG. 4 is a diagram showing the outline of Method G.

The outline of Method G is shown in FIG. 4.

2-3-6-1 Step G-1

The present step is the step of reacting the hydroxy group of phenol (referred to as Tr-O—X—H in FIG. 4, wherein Tr represents a protective group for the hydroxy group) in the compound (11) produced in step C-2, the compound (14a) produced in step D-2a, the compound (14b) produced in step D-2b, the compound (14c) produced in step D-2c, the compound (17) produced in step E-2, or the compound (22) produced in step F-3 with mono-substituted chloro(alkoxy)phosphines (referred to as R$^5$—P(—O—R$^4$)—Cl in FIG. 4) or di-substituted alkoxyphosphines (referred to as (R$^5$—)$_2$P(—O—R$^4$) in FIG. 4) for use in conversion to an amidite form to produce a compound (23).

Tr is not particularly limited as long as it is a protective group for the hydroxy group that can be deprotected without eliminating the protective group in the nucleic acid.

Examples thereof can include a 4-methoxytrityl group, a 4,4'-dimethoxytrityl group, a pixyl group, a trityl group, a levulinyl group, and a bis(trimethylsilyloxy)(cyclohexyloxy)silyl group. A 4-methoxytrityl group or a 4,4'-dimethoxytrityl group is preferable.

The solvent used is not particularly limited as long as it does not influence the reaction. Preferable examples thereof include: ethers such as tetrahydrofuran, diethyl ether, and dioxane; and halogenated hydrocarbons such as methylene chloride, chloroform, carbon tetrachloride, dichloroethane, chlorobenzene, and dichlorobenzene.

Examples of $R^4$ in the present step can include a 2-cyanoethyl group, a methyl group, a methanesulfonylethyl group, a 2,2,2-trichloroethyl group, and an allyl group. A cyanoethyl group or a methyl group is preferable.

Examples of $R^5$ in the present step can include a morpholino group, a diisopropylamino group, a diethylamino group, and a dimethylamino group. A diisopropylamino group is preferable.

Examples of the mono-substituted chloro(alkoxy)phosphines used include phosphines such as chloro(morpholino)methoxyphosphine, chloro(morpholino)cyanoethoxyphosphine, chloro(dimethylamino)methoxyphosphine, chloro(dimethylamino)cyanoethoxyphosphine, chloro(diisopropylamino)methoxyphosphine, and chloro(diisopropylamino)cyanoethoxyphosphine. Chloro(morpholino)methoxyphosphine, chloro(morpholino)cyanoethoxyphosphine, chloro(diisopropylamino)methoxyphosphine, or chloro(diisopropylamino)cyanoethoxyphosphine is preferable.

When the mono-substituted chloro(alkoxy)phosphines are used, a deoxidizer is used. In this case, examples of the deoxidizer used include: heterocyclic amines such as pyridine and dimethylaminopyridine; and aliphatic amines such as trimethylamine, triethylamine, and diisopropylethylamine. Aliphatic amines (particularly, diisopropylethylamine) are preferable.

Examples of the di-substituted alkoxyphosphines used can include phosphines such as bis(diisopropylamino)cyanoethoxyphosphine, bis(diethylamino)methanesulfonylethoxyphosphine, bis(diisopropylamino) (2,2,2-trichloroethoxy) phosphine, and bis(diisopropylamino)(4-chlorophenylmethoxy)phosphine. Bis(diisopropylamino)cyanoethoxyphosphine is preferable.

When the di-substituted alkoxyphosphines are used, an acid is used. In this case, the acid used is preferably tetrazole, acetic acid, or p-toluenesulfonic acid.

The reaction temperature is not particularly limited and is usually 0 to 80° C., preferably room temperature.

The reaction time differs depending on starting materials used, reagents, temperature, etc., and is usually 5 minutes to 30 hours, preferably 30 minutes to 10 hours for reaction at room temperature.

After completion of the reaction, the compound (23) of interest in the present reaction is obtained, for example, by: appropriately neutralizing the reaction mixture, or removing insoluble matter, if any, by filtration; then adding water and a water-immiscible organic solvent such as ethyl acetate; after washing with water, separating the organic layer containing the compound of interest; drying the organic layer over anhydrous magnesium sulfate or the like; and then distilling off the solvent.

The obtained compound of interest can be further purified, if necessary, by a standard method, for example, recrystallization, reprecipitation, or chromatography.

2-3-6-2 Step G-2

The present step is the step of reacting the compound (2) produced in step A-1 with the compound (23) produced in step G-1 by a usual phosphoramidite method using an automatic DNA synthesizer to produce a compound (24) (in the diagram, $W^2$ represents a protected sense strand polynucleotide without 5'-terminal and 3'-terminal hydroxy groups, $W^1$—Y represents a protected antisense strand polynucleotide without 5'-terminal and 3'-terminal hydroxy groups, and $Tr^1$ represents a protective group for the hydroxy group).

$Tr^1$ is not particularly limited as long as it is a protective group for the hydroxy group that can be deprotected without eliminating the protective group in the nucleic acid. Examples thereof can include a 4-methoxytrityl group, a 4,4'-dimethoxytrityl group, a pixyl group, a trityl group, a levulinyl group, and a bis(trimethylsilyloxy)(cyclohexyloxy)silyl group. A 4-methoxytrityl group or a 4,4'-dimethoxytrityl group is preferable.

The compound (24) is produced by a usual phosphoramidite method using an automatic DNA synthesizer. The oligonucleotide analog having the desired nucleotide sequence can be synthesized according to a method described in the literature (Nucleic Acids Research, 12, 4539 (1984)) using a DNA synthesizer, for example, model 392 (manufactured by PerkinElmer Inc.), which is based on the phosphoramidite method.

Moreover, when the oligonucleotide analog is converted, if desired, to a thioate form, a thioate derivative can be obtained according to methods described in the literature (Tetrahedron Letters, 32, 3005 (1991); and J. Am. Chem. Soc., 112, 1253 (1990)) using sulfur or a reagent such as tetraethylthiuram disulfide (TETD, Applied Biosystems), Beaucage reagent, or a phenylacetyl disulfide/pyridine-acetonitrile (1:1 v/v) solution (Ravikumar, V. T. et al., Bioorg. Med. Chem. Lett. (2006) 16, p. 2513-2517)

2-3-6-3 Step G-3

The present step is the step of excising the compound (24) produced in step G-2 from CPG and removing the protective group to produce a final compound (25) (in the diagram, $W^{2'}$ represents a sense strand polynucleotide without 5'-terminal and 3'-terminal hydroxy groups, and $W^{1'}$—Y' represents an antisense strand polynucleotide without 5'-terminal and 3'-terminal hydroxy groups).

Examples of the base used can include concentrated ammonia water, methanolic ammonia, ethanolic ammonia, a concentrated ammonia water-ethanol (3:1 v/v) mixed solution, a concentrated ammonia water-40% aqueous methylamine solution (1:1 v/v) mixed solution, methylamine, a 0.5 M aqueous LiOH solution, and a 3.5 M triethylamine-methanol solution (1:10 v/v) mixed solution. Concentrated ammonia water or a concentrated ammonia water-ethanol (3:1 v/v) mixed solution is preferable.

The reaction temperature is not particularly limited and is usually −50 to 80° C., preferably room temperature to 60° C.

The reaction time differs depending on starting materials used, reagents, temperature, etc., and is usually 5 minutes to 30 hours, preferably 5 hours for reaction at 60° C.

When a compound obtained by distilling off the solvent after completion of the reaction is bound to $Tr^1$, the compound can be purified by purification procedures, for example, various chromatography techniques such as reverse-phase and ion-exchange chromatography (including high-performance liquid chromatography).

When, for example, a 4-methoxytrityl group, a 4,4'-dimethoxytrityl group, a pixyl group, or a trityl group, remains without being deprotected under basic conditions, Tr¹ can be deprotected under acidic conditions in the same way as for step F-2. The conditions preferably involve an 80% aqueous acetic acid solution.

The reaction mixture containing the compound (25) thus obtained can be purified by purification procedures; used in usual nucleic acid purification, for example, various chromatography techniques such as reverse-phase chromatography and ion-exchange chromatography (including high-performance liquid chromatography) to obtain the compound (25).

A 3L5-polynucleotide and a double-stranded polynucleotide having an unmodified 3'-terminal phosphate of a sense strand and an unmodified 5'-terminal phosphate of an antisense strand can be obtained by the present method.

The 3L5-polynucleotide also includes: a 3L5-polynucleotide comprising a cholesterol, lipid, or vitamin E unit introduced therein (see e.g., Lorenz, C. et al. Bioorg. Med. Chem. Lett., 14, p. 4975-4977 (2004); Soutschek, J., et al. Nature, 432, p. 173-178, (2004); Wolfrum, C. et al. Nature Biotech. 25, p. 1149-1157, (2007); Kubo, T. et al. Oligonucleotides, 17, p. 1-20, (2007); Kubo, T., et al. Biochem. Biophys. Res. Comm. 365, p. 54-61, (2008); and Nishina, K., et al., Mol. Ther. 16, p. 734-740, (2008)); and a 3L5-polynucleotide bound at the end with an aptamer, a protein-binding nucleic acid molecule.

The 3L5-polynucleotide also includes a 3L5-polynucleotide bound to a monoclonal antibody (or an appropriate binding fragment thereof) or a protein (or an appropriate oligopeptide fragment thereof) (see e.g., Song, et al. Nature Biotech. 23, p. 709-717 (2005); Xia et al. Pharm. Res. 24, p. 2309-2316 (2007); and Kumar, et al. Nature, 448, p. 39-43 (2007)).

Moreover, the 3L5-polynucleotide also includes a positively charged complex of a 3L5-polynucleotide supplemented with a cationic polymer (see, as successful examples achieving distribution in organs and cells, Leng et al. J. Gen. Med. 7, p. 977-986 (2005); Baigude et al. 2, p. 237-241, ACS Chem. Biol. (2007); and Yadava et al. Oligonucleotide 17, p. 213-222 (2007)).

The 3L5-polynucleotide includes every pharmaceutically acceptable salt or ester of the 3L5-polynucleotide, or salts of such esters.

Preferable examples of the pharmaceutically acceptable salt of the 3L5-polynucleotide can include: alkali metal salts such as a sodium salt, a potassium salt, and a lithium salt; alkaline earth metal salts such as a calcium salt and a magnesium salt, and metal salts such as an aluminum salt, an iron salt, a zinc salt, a copper salt, a nickel salt, and a cobalt salt; amine salts including inorganic salts such as an ammonium salt and organic salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt, a tris(hydroxymethyl)aminomethane salt; inorganic acid salts such as a hydrohalide (e.g., a hydrofluoride, a hydrochloride, a hydrobromide, and a hydroiodide), a nitrate, a perchlorate, a sulfate, and a phosphate; organic acid salts such as lower alkanesulfonates (e.g., a methanesulfonate, a trifluoromethanesulfonate, and an ethanesulfonate), arylsulfonates (e.g., a benzenesulfonate and a p-toluenesulfonate), an acetate, a malate, a fumarate, a succinate, a citrate, a tartrate, an oxalate, and a maleate; and amino acid salts such as a glycine salt, a lysine salt, an arginine salt, an ornithine salt, a glutamate, and an aspartate.

A composition comprising the 3L5-polynucleotide is mixed, encapsulated, or conjugated with another molecule, molecular structure, or mixture of compounds, for example, as a liposome, a receptor-targeting molecule, an oral, rectal, or local formulation, or other formulations for assisting in uptake, distribution, and/or absorption.

When the 3L5-polynucleotide is used as a preventive or therapeutic drug for disease, the polynucleotide or a pharmacologically acceptable salt thereof can be administered either by itself or after mixing with an appropriate pharmacologically acceptable excipient, diluent, or the like, as an oral formulation such as tablets, capsules, granules, powders, or syrups or as a parenteral formulation such as injections, suppositories, patches, or external preparations.

These preparations are produced by a well-known method using additives such as excipients (examples thereof can include organic excipients including: sugar derivatives such as lactose, saccharose, glucose, mannitol, and sorbitol; starch derivatives such as corn starch, potato starch, a starch, and dextrin; cellulose derivatives such as crystalline cellulose; gum arabic; dextran; and pullulan, and inorganic excipients including: silicate derivatives such as light anhydrous silicic acid, synthetic aluminum silicate, calcium silicate, and magnesium aluminometasilicate; a phosphate such as calcium hydrogen phosphate; a carbonate such as calcium carbonate; and a sulfate such as calcium sulfate), lubricants (examples thereof can include: metal salts of stearic acid such as stearic acid, calcium stearate, and magnesium stearate; talc; colloidal silica; waxes such as beeswax and spermaceti; boric acid; adipic acid; a sulfate such as sodium sulfate; glycol; fumaric acid; sodium benzoate; DL leucine; a lauryl sulfate such as sodium lauryl sulfate and magnesium lauryl sulfate; silicic acids such as anhydrous silicic acid and silicic hydrate; and the starch derivatives described above), binders (examples thereof can include hydroxypropylcellulose, hydroxypropylmethylcellulose, polyvinylpyrrolidone, macrogol, and the same compounds as the excipients), disintegrants (examples thereof can include: cellulose derivatives such as low substituted hydroxypropylcellulose, carboxymethylcellulose, carboxymethylcellulose calcium, and internally bridged carboxymethylcellulose sodium; and chemically modified starches/celluloses such as carboxymethyl starch, carboxymethyl starch sodium, and bridged polyvinylpyrrolidone), emulsifier (examples thereof can include: colloidal clay such as bentonite and veegum; a metal hydroxide such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester), stabilizers (examples thereof can include: p-oxybenzoic acid esters such as methylparaben and propylparaben; alcohols such as chlorobutanol, benzyl alcohol, and phenylethyl alcohol; benzalkonium chloride; phenols such as phenol and cresols; thimerosal; dehydroacetic acid; and sorbic acid), corrigents (examples thereof can include sweeteners, acidulants, and flavors that are usually used), and diluents.

3. Introduction of 3L5-Polynucleotide to Cells, Tissues, or Individuals, and Regulation of Expression of Target Gene Recipients to which or to whom the 3L5-polynucleotide thus prepared is introduced are not particularly limited as long as the target gene can be intracellularly transcribed into RNA therein. The recipients mean cells, tissues, or individuals.

The cells for which the 3L5-polynucleotide is used may be any of germline cells, somatic cells, totipotent cells, pluripotent cells, cleaved cells, non-cleaved cells, parenchymal cells, epithelial cells, immortalized cells, transformed cells, nerve cells, and immunocytes.

The tissues include single cell embryos or constitutive cells, or polyploid embryos, embryonic tissues, or the like. Moreover, examples of the above differentiated cells include adipocytes, fibroblasts, myocytes, cardiomyocytes, endothelial cells, nerve cells, glial cells, blood cells, megakaryocytes, lymphocytes, macrophages, neutrophils, eosinophils, basophiles, mast cells, leukocytes, granulocytes, keratinocytes, chondrocytes, osteoblasts, osteoclasts, hepatocytes, and endocrine or exocrine cells. For example, CHO-K1-cells (RIKEN Cell bank), Drosophila S2 cells (Schneider, I. et al., J. Embryol. Exp. Morph., 27, p. 353-365 (1972)), human HeLa cells (ATCC: CCL-2), or human HEK293 cells (ATCC: CRL-1573) are preferably used as such cells.

Furthermore, specific examples of the individuals used as recipients of the 3L5-polynucleotide include plants, animals, protozoans, viruses, bacteria, and those organisms belonging to the Eumycetes. The plants may be monocots, dicots, or gymnosperms. The animals may be vertebrates or invertebrates. The vertebrates are preferably mammals including mice, rats, monkeys, dogs, and humans.

When the recipients are cells or tissues, a calcium phosphate method, electroporation, a lipofection method, viral infection, immersion in a 3L5-polynucleotide solution, or transformation, or the like is used as a method for introducing the 3L5-polynucleotide into the recipients. Moreover, examples of methods for introduction into embryos include microinjection, electroporation, and viral infection. When the recipients are plants, a method involving injection or perfusion into the cavities or interstitial cells or the like of the plants or spraying thereonto is used. Moreover, for animal individuals, a method involving systemic introduction through, for example, oral, local, subcutaneous, intramuscular, intravenous, parenteral, transvaginal, rectal, nasal, ocular, or transmucosal administration, or electroporation, viral infection, or the like is used. A method by which the 3L5-polynucleotide is directly mixed with a diet for the organisms can also be used as an oral introduction method.

In addition to these approaches, a colloidal dispersion system can be used as a method for introducing the 3L5-polynucleotide into patients.

The colloidal dispersion system is expected to have the effect of enhancing the in-vivo stability of the compound or the effect of efficiently transporting the compound to particular organs, tissues, or cells.

The colloidal dispersion system used is not limited as long as it is usually applicable. Examples thereof can include polymer complexes, nanocapsules, microspheres, beads, and water-in-oil emulsifier, micelles, mixed micelles, and lipid-based dispersion systems including liposomes. Preferably, the colloidal dispersion system is a plurality of liposomes or artificial membrane vesicles having the effect of efficiently transporting the compound to particular organs, tissues, or cells (Mannino et al., Biotechniques, 1988, 6, p. 682-; Blume and Cevc, Biochem. et Biophys. Acta, 1990, 1029, p. 91-; Lappalainen et al., Antiviral Res., 1994, 23, p. 119-; and Chonn and Cullis, Current Op. Biotech., 1995, 6, p. 698-).

Unilamellar liposomes of 0.2 to 0.4 µm in size range are capable of encapsulating a considerable amount of an aqueous buffer containing macromolecules, and the compounds are encapsulated in this aqueous inner membrane and transported in a biologically active form to brain cells (Fraley et al., Trends Biochem. Sci., 1981, 6, p. 77-80).

The liposome composition is usually a complex of lipid, particularly phospholipid, specifically phospholipid having a high phase transition temperature, with one or more steroids, particularly cholesterols.

Examples of the lipid useful for liposome production include phosphatidyl compounds such as phosphatidyl glycerol, phosphatidyl choline, phosphatidyl serine, sphingolipid, phosphatidyl ethanolamine, cerebroside, and ganglioside.

Diacyl phosphatidyl glycerol is particularly useful, wherein the lipid moiety contains 14 to 18 carbon atoms and is saturated (devoid of any internal double bonds in the chain of 14 to 18 carbon atoms) and, in particular, contains 16 to 18 carbon atoms.

Typical phospholipids encompass phosphatidyl choline, dipalmitoyl phosphatidyl choline, and distearoyl phosphatidyl choline.

Targeting by the colloidal dispersion system including liposomes may be passive or active.

Such passive targeting is achieved by use of the fundamental tendency of liposomes to be distributed to reticuloendothelial cells in organs containing sinusoids.

On the other hand, examples of active targeting can include liposome modification approaches involving binding particular ligands such as viral coat protein (Morishita et al., Proc. Natl. Acad. Sci. (U.S.A.), 1993, 90, p. 8474-), monoclonal antibodies (or appropriate binding fragment thereof), sugars, glycolipids, or proteins (or appropriate oligopeptide fragments thereof) to liposomes or changing liposome composition to achieve distribution to organs and cell types other than naturally occurring sites of localization.

The surface of the colloidal dispersion system may be modified in various ways for targeting purposes.

In the liposomal targeted delivery system, a lipid group can be incorporated into the lipid bilayer of the liposome to maintain target ligands through tight association with the lipid bilayer.

Various linking groups may be used for linking the lipid chain to the target ligands.

The target ligands binding to particular cell surface molecules predominantly found on cells desired to receive the delivery of the 3L5-polynucleotide can be, for example, (1) hormones, growth factors, or appropriate oligopeptide fragments thereof, binding to particular cell receptors predominantly expressed by the cells desired to receive the delivery, or (2) polyclonal or monoclonal antibodies or appropriate fragments thereof (e.g., Fab or F(ab')2) specifically binding to antigenic epitopes predominantly found on the target cells.

Two or more bioactive agents can also be compounded within a single liposome and administered.

A medicament for enhancing the intracellular stability of the contents and/or targeting may further be added to the colloidal dispersion system.

The amount of the 3L5-polynucleotide or pharmacologically acceptable salt thereof used differs depending on symptoms, ages, etc., 1 mg (preferably, 30 mg) as the lower limit to 2000 mg (preferably, 1500 mg) as the upper limit of the polynucleotide or the salt per dose for oral administration, 0.5 mg (preferably, 5 mg) as the lower limit to 500 mg (preferably, 250 mg) as the upper limit of the polynucleotide or the salt per dose for intravenous or subcutaneous administration, 0.5 mg (preferably, 5 mg) as the lower limit to 500 mg (preferably, 250 mg) as the upper limit of the polynucleotide or the salt per dose for intratracheal administration, or 0.05 mg (preferably, 0.5 mg) as the lower limit to 10 mg (preferably, 5 mg) as the upper limit of the polynucleotide or the salt per dose for intraocular administration is preferably administered to an adult once to three times a day according to symptoms.

Alternatively, a safer drug is preferably administered once to three times a week according to symptoms. A much safer drug is preferably administered once to three times a month according to symptoms.

Pharmaceutical compositions and formulations for local administration include transdermal patches, ointments, lotions, creams, gels, troches, suppositories, sprays, liquids, and powders.

EXAMPLES

Hereinafter, the present invention will be described more specifically with reference to Examples, Reference Examples, and Test Examples. However, the present invention is not intended to be limited to them. In the Examples below, procedures of genetic engineering were performed by the methods described in "Molecular Cloning" [Sambrook, J., Fritsch, E. F. and Maniatis, T., published in 1989 by Cold Spring Harbor Laboratory Press] or according to the instructions of the commercially available reagents or kits used, unless otherwise specified. The structural formula of X in each polynucleotide synthesized in the Examples and the molecular weight measured value of each polynucleotide measured with a mass spectrometer are shown in Tables 1 to 3.

Reference Example 1

Synthesis of HO-$G^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1t}$-H (SEQ ID NO: 1 of the Sequence Listing) (CT-169)

CT-169 was synthesized according to an RNA synthesis program on the scale of 0.2 μmol using an automatic nucleic acid synthesizer (manufactured by PerkinElmer Inc., ABI model 394 DNA/RNA synthesizer). Solvents, reagents, and phosphoramidites were used in each synthesis cycle at the same concentrations as in natural oligodeoxynucleotide synthesis.

When deoxynucleoside phosphoramidites were used, 5'-O-dimethoxytrityl-6-N-benzoyl-2'-deoxyadenosine-3'-O-(2-cyanoethyl N,N-diisopropyl)phosphoramidite, 5'-O-dimethoxytrityl-2-N-isobutyryl-2'-deoxyguanosine-3'-O-(2-cyanoethyl N,N-diisopropyl)phosphoramidite, 5'-O-dimethoxytrityl-4-N-benzoyl-2'-deoxycytidine-3'-O-(2-cyanoethyl N,N-diisopropyl)phosphoramidite, and 5'-O-dimethoxytritylthymidine-3'-O-(2-cyanoethyl N,N-diisopropyl)phosphoramidite were purchased from Proligo and appropriately adjusted for use.

When 2'-O-methyl nucleoside phosphoramidites were used, 5'-O-dimethoxytrityl-6-N-benzoyl-2'-O-methyladenosine-3'-O-(2-cyanoethyl N,N-diisopropyl)phosphoramidite, 5'-O-dimethoxytrityl-2-N-isobutyryl-2'-O-methylguanosine-3'-O-(2-cyanoethyl N,N-diisopropyl)phosphoramidite, 5'-O-dimethoxytrityl-4-N-acetyl-2'-O-methylcytidine-3'-O-(2-cyanoethyl N,N-diisopropyl)phosphoramidite, and 5'-O-dimethoxytrityl-2'-O-methyluridine-3'-O-(2-cyanoethyl N,N-diisopropyl)phosphoramidite were purchased from Glen Research Corp. and appropriately adjusted for use.

When ribonucleoside phosphoramidites were used, 5'-O-dimethoxytrityl-6-N-benzoyl-2'-O-(tert-butyldimethylsilyl)adenosine-3'-O-(2-cyanoethyl N,N-diisopropyl)phosphoramidite, 5'-O-dimethoxytrityl-2-N-dimethylformamidine-2'-O-(tert-butyldimethylsilyl)guanosine-3'-O-(2-cyanoethyl N,N-diisopropyl)phosphoramidite, 5'-O-dimethoxytrityl-4-N-acetyl-2'-O-(tert-butyldimethylsilyl)cytidine-3'-O-(2-cyanoethyl N,N-diisopropyl)phosphoramidite, and 5'-O-dimethoxytrityl-2'-O-(tert-butyldimethylsilyl)uridine-3'-O-(2-cyanoethyl N,N-diisopropyl)phosphoramidite were purchased from Proligo and appropriately adjusted for use.

When 2'-O,4'-C-ethylene nucleoside phosphoramidites were used, compounds of Example 14 (5'-O-dimethoxytrityl-2'-O,4'-C-ethylene-6-N-benzoyladenosine-3'-O-(2-cyanoethyl N,N-diisopropyl)phosphoramidite), Example 27 (5'-O-dimethoxytrityl-2'-O,4'-C-ethylene-2-N-isobutyrylguanosine-3'-O-(2-cyanoethyl N,N-diisopropyl)phosphoramidite), Example 22 (5'-O-dimethoxytrityl-2'-O,4'-C-ethylene-4-N-benzoyl-5-methylcytidine-3'-O-(2-cyanoethyl N,N-diisopropyl)phosphoramidite), and Example 9 (5'-O-dimethoxytrityl-2'-O,4'-C-ethylene-5-methyluridine-3'-O-(2-cyanoethyl N,N-diisopropyl)phosphoramidite) of Japanese Patent No. 3420984 were appropriately prepared for use.

When each polynucleotide has a 5'-terminal phosphate group moiety, PHOSPHALINK (manufactured by Applied Biosystems) was appropriately adjusted for use.

The phosphoramidites were appropriately supplied to the automatic nucleic acid synthesizer to synthesize a polynucleotide having the desired sequence. 0.5 μmol of CPG (controlled pore glass; manufactured by Applied Biosystems or Glen Research Corp.) bound with the desired nucleosides was used as a solid-phase carrier to synthesize the title polynucleotide. In the final step of the automatic nucleic acid synthesizer, acid treatment was not performed (the dimethoxytrityl group was bound to the oligonucleotide). The present polynucleotide was treated with an ammonia water and then purified by reverse-phase HPLC (LC-10VP manufactured by Shimadzu Corp., column (Merck, Chromolith Performance RP-18e (4.6×100 mm)), Solution A: 5% acetonitrile, 0.1 M aqueous triethylammonium acetate solution (TEAA), pH 7.0, Solution B: acetonitrile, B %: 10%-*60% (10 min, linear gradient); 60° C.; 2 ml/min; 260 nm) to gather peaks of the product of interest having the dimethoxytrityl group. Water was added thereto, and TEAA was distilled off under reduced pressure. When the dimethoxytrityl group was bonded thereto, an 80% aqueous acetic acid solution (2 mL) was added thereto, and the mixture was left for 20 minutes to deprotect the dimethoxytrityl group. The solvent was distilled off, and the residue was dissolved in 500 μl of water, washed with ethyl acetate, and freeze-dried to obtain the oligonucleotide of interest. Moreover, if necessary, the obtained precipitates were purified by 20% polyacrylamide gel electrophoresis containing 7 M urea (1×TBE, 600 V, 4 hours). After the electrophoresis, bands were visualized using a UV lamp, and the bands of interest were excised using a knife. 1 mL of a solution containing 0.2 M NaCl and 10 mM EDTA (pH 7.2) was added thereto, and the mixture was left overnight to elute the polynucleotide from the gel slice. The oligonucleotide was precipitated by the addition of ethanol and collected by centrifugation. The molecular weight of the present polynucleotide was identified by negative ion ESI mass spectrometry.

Molecular weight calculated value: 5767.86, measured value: 5767.78

Nucleotide sequence: comprising a sequence of nucleotide Nos. 3139-3156 of the human β-catenin gene (GenBank accession No. NM_001904.3)

Example 1

Synthesis of HO-G$^p$-C$^{m1p}$-A$^p$-C$^{m1p}$-A$^p$-A$^{m1p}$-G-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-X-P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-U$^{m1p}$-G$^p$-U$^{m1p}$-G$^p$-C$^{m1p}$-T$^p$-U$^{m1t}$-H (CT-437)

CT-437 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X.

Figure 6:
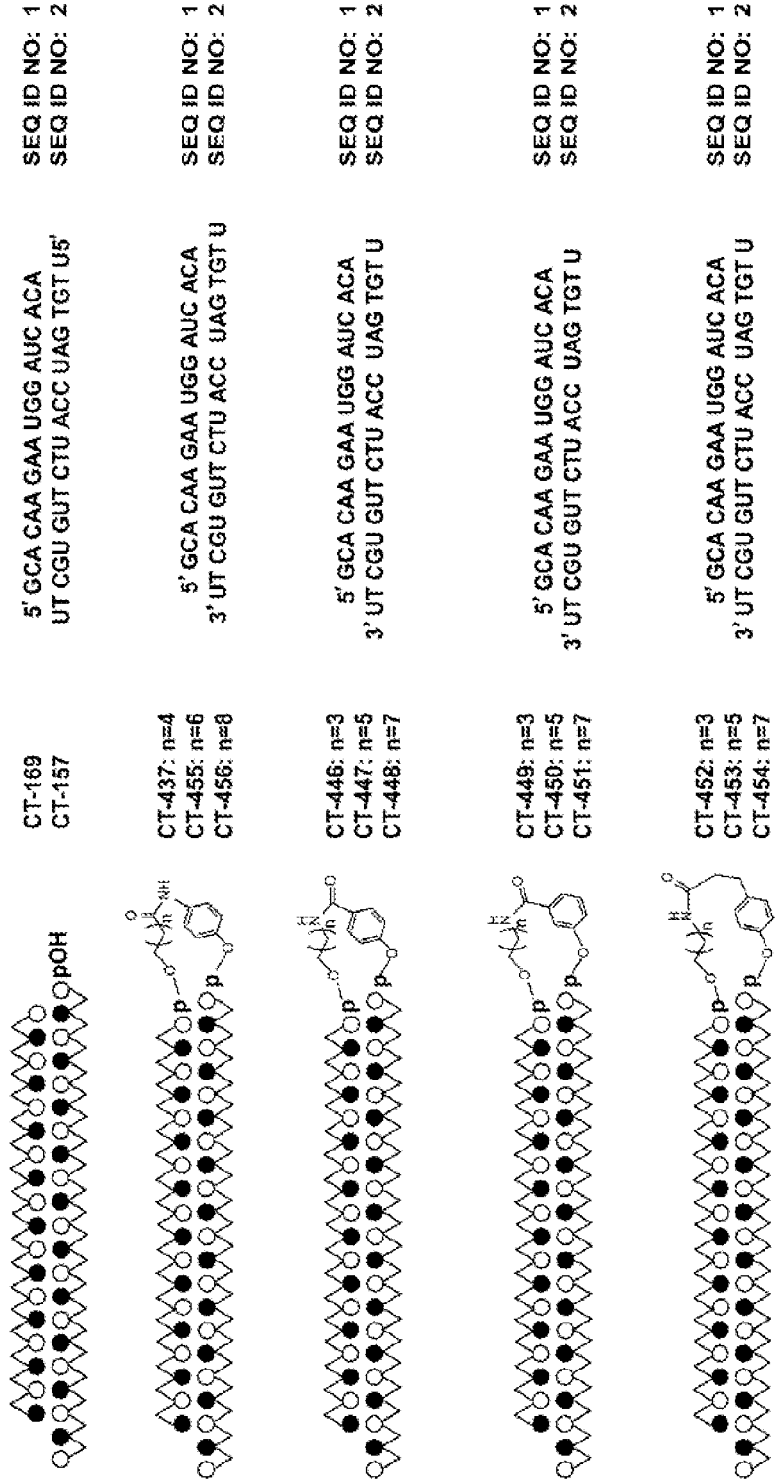
FIG. 6 is a diagram showing polynucleotides corresponding to the human β-catenin gene (hereinafter, examples of combinations of polynucleotides as sense and antisense strands will be shown in each diagram; for symbols, the filled circle (●) represents a DNA, and the open circle (○) represents a 2'-O-methyl RNA. The line between the filled circle and the open circle represents a phosphodiester bond between the nucleosides. In the diagram, p represents —P(=O)(OH)—. When p is bound, a hydrogen atom in the terminal hydroxy group of the polynucleotide is removed. When the end of the polynucleotide is unbound, the 3'-end or 5'-end of the DNA or the 2'-O-methyl RNA is an OH group. n represents the number of carbon atoms. The same holds true for FIGS. 7 and 11. The nucleotide sequence of each polynucleotide is also shown in the diagram.

CT-437 was synthesized in the same way as for Reference Example 1. For the present polynucleotide, the X moiety was coupled with an X amidite reagent prepared as follows: the compound (20 mg) obtained in Reference Example 3 was dissolved in 2 mL of acetonitrile:methylene chloride (1:1 v/v). To this solution, 2-cyanoethyl tetraisopropylphosphorodiamidite (74 μL, 0.23 mmol) and 360 μL of a 0.45 M solution of 1H-tetrazole in acetonitrile were added, and the mixture was stirred for 2 hours. The progression of the reaction was confirmed by TLC, followed by filter filtration to prepare the X amidite reagent. The structure of CT-437 is shown in FIG. 6.

Example 2

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-T$^p$-C$^{m1p}$-T$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (CT-455)

CT-455 was synthesized in the same way as for Example 1. The amidite reagent for the X moiety in the present polynucleotide was prepared using the compound (20 mg) obtained in Reference Example 4.

CT-455 is a polynucleotide in which the 3-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-455 is shown in FIG. 6.

Example 3

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (CT-456)

CT-456 was synthesized in the same way as for Example 1. The amidite reagent for the X moiety in the present polynucleotide was prepared using the compound (20 mg) obtained in Reference Example 5.

CT-456 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-456 is shown in FIG. 6.

Example 4

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-T$^p$-A$^{m1p}$-C$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (CT-446)

CT-446 was synthesized in the same way as for Example 1. The amidite reagent for the X moiety in the present polynucleotide was prepared using the compound (20 mg) obtained in Reference Example 6.

CT-446 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-446 is shown in FIG. 6.

Example 5

Synthesis of HO-G$^p$-C$^{m1p}$-A$^p$-C$^{m1p}$-A$^p$-A$^{m1p}$-G$^p$-A$^{m1p}$-U$^{m1p}$-G$^p$-G$^{m1p}$-A$^p$-U$^{m1p}$-C$^p$-A$^{m1p}$-C$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (CT-447)

CT-447 was synthesized in the same way as for Example 1. The amidite reagent for the X moiety in the present polynucleotide was prepared using the compound (20 mg) obtained in Reference Example 7.

CT-447 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-447 is shown in FIG. 6.

Example 6

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (CT-448)

CT-448 was synthesized in the same way as for Example 1. The amidite reagent for the X moiety in the present polynucleotide was prepared using the compound (20 mg) obtained in Reference Example 8.

CT-448 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-448 is shown in FIG. 6.

Example 7

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-X—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-U$^{m1t}$-H (CT-449)

CT-449 was synthesized in the same way as for Example 1. The amidite reagent for the X moiety in the present polynucleotide was prepared using the compound (20 mg) obtained in Reference Example 9.

CT-449 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-449 is shown in FIG. 6.

Example 8

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-450)

CT-450 was synthesized in the same way as for Example 1. The amidite reagent for the X moiety in the present polynucleotide was prepared using the compound (20 mg) obtained in Reference Example 10.

CT-450 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-450 is shown in FIG. 6.

Example 9

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$T^p$-$A^{m1p}$-$T^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-451)

CT-451 was synthesized in the same way as for Example 1. The amidite reagent for the X moiety in the present polynucleotide was prepared using the compound (20 mg) obtained in Reference Example 11.

CT-451 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-451 is shown in FIG. 6.

Example 10

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-452)

CT-452 was synthesized in the same way as for Example 1. The amidite reagent for the X moiety in the present polynucleotide was prepared using the compound (20 mg) obtained in Reference Example 12.

CT-452 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-452 is shown in FIG. 6.

Example 11

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-453)

CT-453 was synthesized in the same way as for Example 1. The amidite reagent for the X moiety in the present polynucleotide was prepared using the compound (20 mg) obtained in Reference Example 13.

CT-453 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-453 is shown in FIG. 6.

Example 12

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$U^{m1p}$-$T^p$-$U^{m1p}$-$G^p$-$U^{m1p}$-$G^p$-$C^{m1p}$-$T^p$-$U^{m1t}$-H (CT-454)

CT-454 was synthesized in the same way as for Example 1. The amidite reagent for the X moiety in the present polynucleotide was prepared using the compound (20 mg) obtained in Reference Example 14.

CT-454 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-454 is shown in FIG. 6.

Example 13

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-460)

CT-460 was synthesized in the same way as for Example 1. The amidite reagent for the X moiety in the present polynucleotide was prepared using the compound (20 mg) obtained in Reference Example 17.

Figure 7:
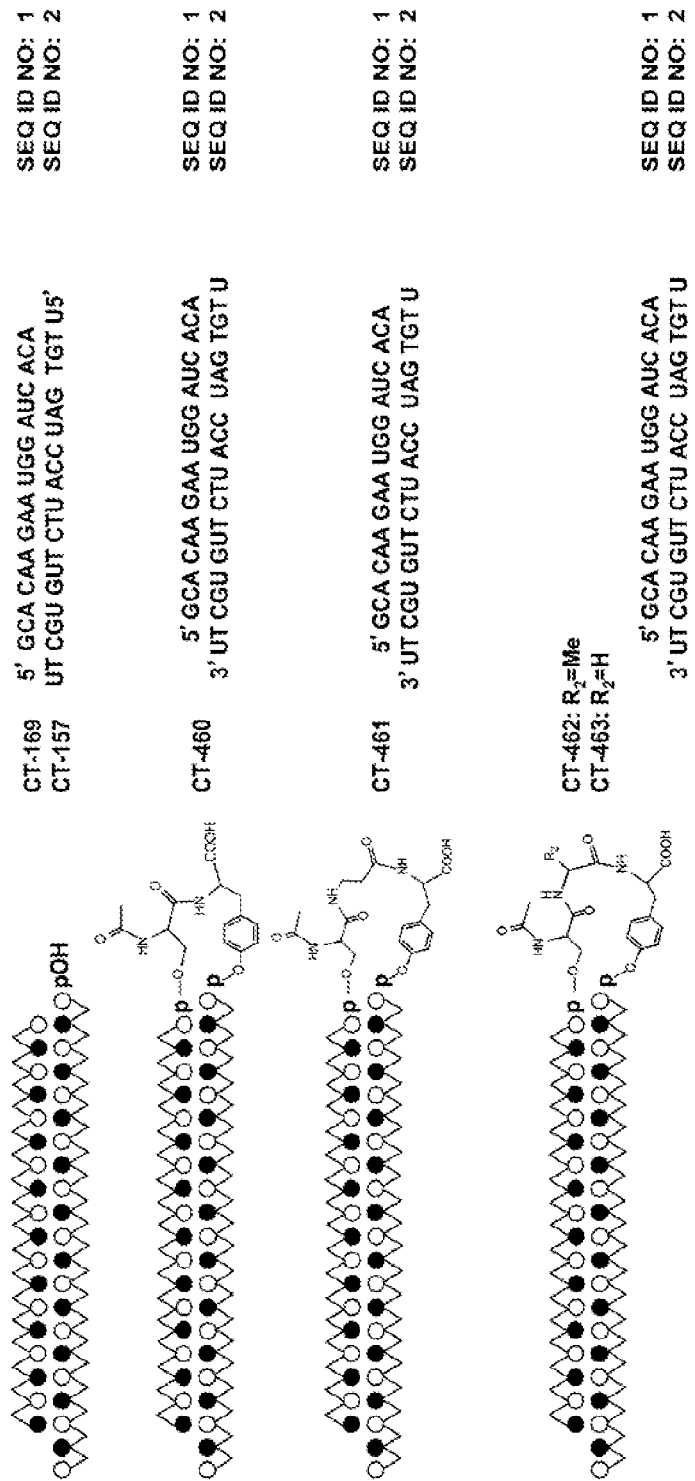
FIG. 7 is a diagram showing polynucleotides corresponding to the human β-catenin gene.

CT-460 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-460 is shown in FIG. 7.

Example 14

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-461)

CT-461 was synthesized in the same way as for Example 1. The amidite reagent for the X moiety in the present polynucleotide was prepared using the compound (20 mg) obtained in Reference Example 21.

CT-461 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-461 is shown in FIG. 7.

Example 15

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-462)

CT-462 was synthesized in the same way as for Example 1. The amidite reagent for the X moiety in the present polynucleotide was prepared using the compound (20 mg) obtained in Reference Example 22.

CT-462 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-462 is shown in FIG. 7.

Example 16

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-463)

CT-463 was synthesized in the same way as for Example 1. The amidite reagent for the X moiety in the present polynucleotide was prepared using the compound (20 mg) obtained in Reference Example 23.

CT-463 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-463 is shown in FIG. 7.

Example 17

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$U$^{m1p}$-$G^p$-$C^{m1p}$-$G^p$-$C^{m1p}$-$T^p$-$U^{m1t}$-H (CT-464)

CT-464 was synthesized in the same way as for Example 1. The amidite reagent for the X moiety in the present polynucleotide was prepared using the compound (20 mg) obtained in Reference Example 26.

Figure 11:
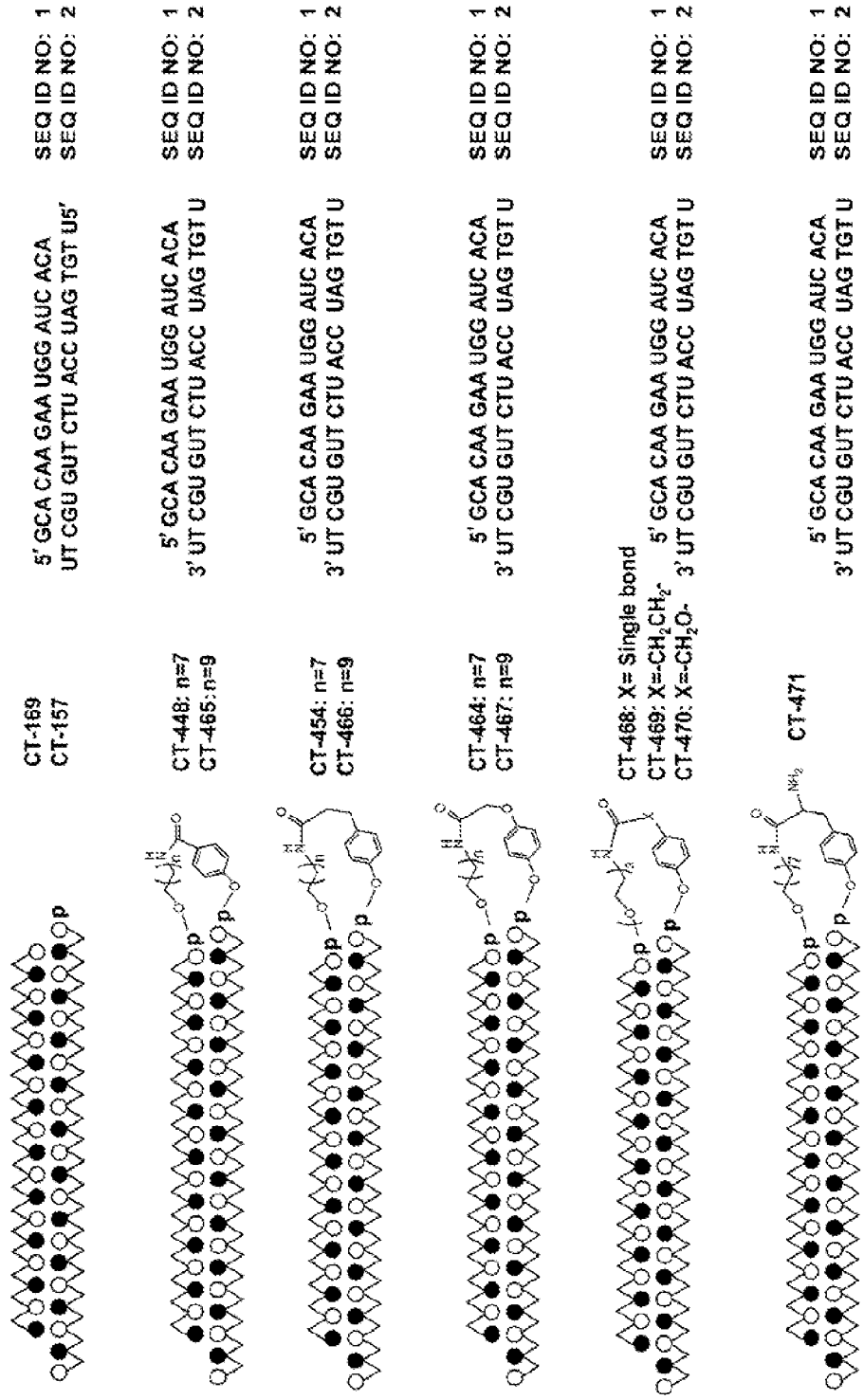
FIG. 11 is a diagram showing polynucleotides corresponding to the human β-catenin gene.

CT-464 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-464 is shown in FIG. 11.

Example 18

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-465)

CT-465 was synthesized in the same way as for Example 1. The amidite reagent for the X moiety in the present polynucleotide was prepared using the compound (20 mg) obtained in Reference Example 24.

CT-465 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-465 is shown in FIG. 11.

Example 19

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-466)

CT-466 was synthesized in the same way as for Example 1. The amidite reagent for the X moiety in the present polynucleotide was prepared using the compound (20 mg) obtained in Reference Example 25.

CT-466 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-466 is shown in FIG. 11.

Example 20

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-467)

CT-467 was synthesized in the same way as for Example 1. The amidite reagent for the X moiety in the present polynucleotide was prepared using the compound (20 mg) obtained in Reference Example 27.

CT-467 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-467 is shown in FIG. 11.

Example 21

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-468)

CT-468 was synthesized in the same way as for Example 1. The amidite reagent for the X moiety in the present polynucleotide was prepared using the compound (20 mg) obtained in Reference Example 28.

CT-468 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-468 is shown in FIG. 11.

Example 22

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-469)

CT-469 was synthesized in the same way as for Example 1. The amidite reagent for the X moiety in the present polynucleotide was prepared using the compound (20 mg) obtained in Reference Example 29.

CT-469 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-469 is shown in FIG. 11.

Example 23

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-470)

CT-470 was synthesized in the same way as for Example 1. The amidite reagent for the X moiety in the present polynucleotide was prepared using the compound (20 mg) obtained in Reference Example 30.

CT-470 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-470 is shown in FIG. 11.

Example 24

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-X—P(=O)(OH)—O—$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (CT-471)

CT-471 was synthesized in the same way as for Example 1. The amidite reagent for the X moiety in the present polynucleotide was prepared using the compound (20 mg) obtained in Reference Example 31.

CT-471 is a polynucleotide in which the 3'-terminal nucleotide of the polynucleotide represented by SEQ ID NO: 1 of the Sequence Listing is linked to the 5'-terminal nucleotide of the polynucleotide represented by SEQ ID NO: 2 through phosphodiester bonds with X. The structure of CT-471 is shown in FIG. 11.

Example 25

Synthesis of HO-$G^{rp}$-$C^{rp}$-$A^{rp}$-$C^{rp}$-$A^{rp}$-$A^{rp}$-$G^{rp}$-$A^{rp}$-$A^{rp}$-$U^{rp}$-$G^{rp}$-$G^{rp}$-$A^{rp}$-$U^{rp}$-$C^{rp}$-$A^{rp}$-$C^{rp}$-$A^{rp}$-$A^{rp}$-$U^{rp}$-$U^{rp}$-X—P(=O)(OH)—O—$U^{rp}$-$U^{rp}$-$G^{rp}$-$U^{rp}$-$G^{rp}$-$A^{rp}$-$U^{rp}$-$C^{rp}$-$C^{rp}$-$A^{rp}$-$U^{rp}$-$U^{rp}$-$C^{rp}$-$U^{rp}$-$G^p$-$U^{rp}$-$G^{rp}$-$C^{rp}$-$U^{rp}$-$U^{rt}$-H (CT-472)

CT-472 was synthesized in the same way as for Example 1. The amidite reagent for the X moiety in the present polynucleotide was prepared using the compound (20 mg) obtained in Reference Example 14.

Figure 13:
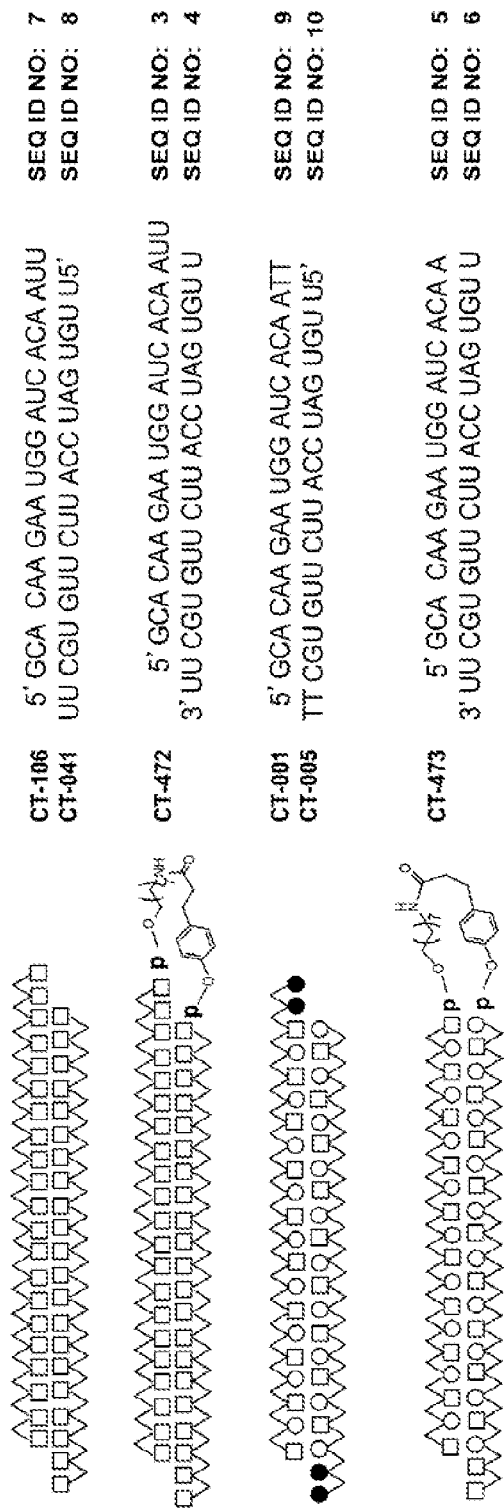
FIG. 13 is a diagram showing polynucleotides corresponding to the human β-catenin gene. For symbols, the open square (□) represents an RNA, the filled circle (●) represents a DNA, and the open circle (○) represents a 2'-O-methyl RNA. The line between the nucleosides represents a phosphodiester bond. In the diagram, p represents —P(=O)(OH)—. When p is bound, a hydrogen atom in the terminal hydroxy group of the polynucleotide is removed. When the end of the polynucleotide is unbound, the 3'-end or 5'-end of the RNA, the DNA, or the 2'-O-methyl RNA is an OH group. n represents the number of carbon atoms. The same holds true for FIGS. 15, 16, and 19. The nucleotide sequence of each polynucleotide is also shown in the diagram.

CT-472 is a polynucleotide in which the 3'-terminal nucleotide of the polynucleotide represented by SEQ ID NO: 3 of the Sequence Listing is linked to the 5'-terminal nucleotide of the polynucleotide represented by SEQ ID NO: 4 through phosphodiester bonds with X. The structure of CT-472 is shown in FIG. 13.

Example 26

Synthesis of HO-$G^{rp}$-$C^{m1p}$-$A^{rp}$-$C^{m1p}$-$A^{rp}$-$A^{m1p}$-$G^{rp}$-$A^{m1p}$-$A^{rp}$-$U^{m1p}$-$G^{rp}$-$G^{m1p}$-$A^{rp}$-$U^{m1p}$-$C^{rp}$-$A^{m1p}$-$C^{rp}$-$A^{m1p}$-$A^{rp}$-X—P(=O)(OH)—O—$U^{m1p}$-$U^{rp}$-$G^{m1p}$-$U^{rp}$-$G^{m1p}$-$A^{rp}$-$U^{m1p}$-$C^{rp}$-$C^{m1p}$-$A^{rp}$-$U^{m1p}$-$U^{rp}$-$C^{m1p}$-$U^{rp}$-$G^{m1p}$-$U^{rp}$-$G^{rp}$-$C^{m1p}$-$U^{rp}$-$U^{rt}$-H (CT-473)

CT-473 was synthesized in the same way as for Example 1. The amidite reagent for the X moiety in the present polynucleotide was prepared using the compound (20 mg) obtained in Reference Example 14.

CT-473 is a polynucleotide in which the 3'-terminal nucleotide of the polynucleotide represented by SEQ ID NO: 5 of the Sequence Listing is linked to the 5'-terminal nucleotide of the polynucleotide represented by SEQ ID NO: 6 through phosphodiester bonds with X. The structure of CT-473 is shown in FIG. 13.

The structures of the X moieties of the polynucleotides described in Examples 1 to 16 and the molecular weights of these polynucleotides are shown in Table 1. In the table, the terminal methylene group of X is bound to the 3'-end of the sense strand polynucleotide to form a phosphodiester bond, while the oxygen atom bonded to the phenyl group is bound to the 5'-end of the antisense strand polynucleotide to form a phosphodiester bond.

TABLE 1

| Example | Name | X | Molecular weight |
|---|---|---|---|
| 1 | CT-437 | 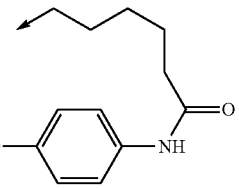 | 12746.04 |

TABLE 1-continued

| Example | Name | X | Molecular weight |
|---------|------|---|------------------|
| 2 | CT-455 | (structure, n = 6) | 12773.15 |
| 3 | CT-456 | (structure, n = 8) | 12801.69 |
| 4 | CT-446 | (structure, n = 3) | 12729.91 |
| 5 | CT-447 | (structure, n = 5) | 12759.91 |
| 6 | CT-448 | (structure, n = 7) | 12787.78 |
| 7 | CT-449 | (structure, n = 3) | 12730.76 |
| 8 | CT-450 | (structure, n = 5) | 12759.76 |
| 9 | CT-451 | (structure, n = 7) | 12786.65 |
| 10 | CT-452 | (structure, n = 3) | 12759.82 |
| 11 | CT-453 | (structure, n = 5) | 12786.29 |
| 12 | CT-454 | (structure, n = 7) | 12814.31 |
| 13 | CT-460 | (structure) | 13831.95 |

TABLE 1-continued

| Example | Name | X | Molecular weight |
|---------|------|---|------------------|
| 14 | CT-461 | [structure] | 12901.92 |
| 15 | CT-462 | [structure] | 12903.12 |
| 16 | CT-463 | [structure] | 12889.32 |

The structures of the X moieties of the polynucleotides described in Examples 17 to 26 and the molecular weights of these polynucleotides are shown in Table 2. In the table, the terminal methylene group of X is bound to the 3'-end of the sense strand polynucleotide to form a phosphodiester bond, while the oxygen atom bonded to the phenyl group is bound to the 5'-end of the antisense strand polynucleotide to form a phosphodiester bond.

TABLE 2

| Example | Name | X | Molecular weight |
|---------|------|---|------------------|
| 17 | CT-464 | [structure] n = 7 | 12816.58 |
| 18 | CT-465 | [structure] n = 9 | 12814.13 |
| 19 | CT-466 | [structure] n = 9 | 12842.97 |
| 20 | CT-467 | [structure] n = 9 | 12844.57 |
| 21 | CT-468 | [structure] | 12790.35 |
| 22 | CT-469 | [structure] | 12818.55 |
| 23 | CT-470 | [structure] | 12820.70 |
| 24 | CT-471 | [structure] n = 7 | 12829.91 |

TABLE 2-continued

| | | | |
|---|---|---|---|
| 25 | CT-472 | 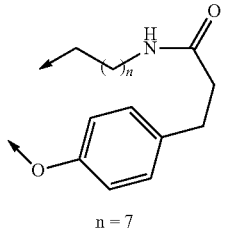 n = 7 | 13711.48 |
| 26 | CT-473 | 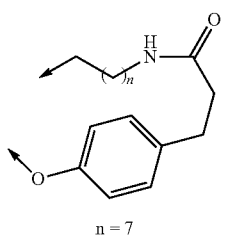 n = 7 | 13365.43 |

Reference Example 2

Synthesis of HO—P(=O)(OH)—O—U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 2 of the Sequence Listing) (CT-157)

CT-157 was synthesized in the same way as for Reference Example 1. The structure of CT-157 is shown in FIG. 6.

Nucleotide sequence: comprising a sequence complementary to nucleotide Nos. 3139-3157 of the human β-catenin gene (GenBank accession No. NM_001904.3)

Reference Example 3

6-(4,4'-dimethoxytrityloxy)hexanoic acid (722 mg, 1.67 mmol; *J. Org. Chem.*, 1995, 60, 3358-3364) was dissolved in 2 mL of methylene chloride. To the solution, 4-aminophenol (200 mg, 1.84 mmol), EDC (288 mg, 2.5 mmol), HOBT (225 mg, 2.5 mmol), and triethylamine (260 L) were added, and the mixture was stirred overnight. The completion of the reaction was confirmed by TLC. Then, the reaction solution was separated into organic and aqueous phases using methylene chloride and a 5% aqueous sodium bicarbonate solution, and the organic phase was washed with saturated saline. The organic phase was dried:over sodium sulfate, and the solvent was then concentrated under reduced pressure. The residue was purified with a silica gel column (30 g, 2% methanol/methylene chloride) to obtain the amorphous compound (649 mg).

$^1$H-NMR (400 MHz, CDCl$_3$) 7.43-6.75 (17H, m), 3.78 (6H, s), 3.08-3.02 (2H, m), 2.32-2.28 (2H, m), 1.73-1.59 (4H, m), 1.49-1.38 (2H, m)

FAB-MAS (mNBA): 525 M$^+$

Reference Example 4

8-hydroxyoctanoic acid (100 mg, 0.59 mmol) was dissolved in 1.5 mL of pyridine. To the solution, 4,4'-dimethoxytrityl chloride (237 mg, 0.7 mmol) was added, and the mixture was stirred overnight. The completion of the reaction was confirmed by TLC. Then, the reaction solution was separated into organic and aqueous phases using methylene chloride and water. The organic phase was dried over sodium sulfate, and the solvent was then concentrated under reduced pressure. The residue was purified with a silica gel column (4 g, methylene chloride) to obtain amorphous 8-(4,4'-dimethoxytrityloxy)octanoic acid (348 mg). The obtained 8-(4,4'-dimethoxytrityloxy)octanoic acid was dissolved in 1 mL of methylene chloride. To the solution, 4-aminophenol (70.9 mg, 0.64 mmol), EDC (101.6 mg, 0.88 mmol), HOBT (79 mg, 0.886 mmol), and triethylamine (92 L) were added, and the mixture was stirred overnight. The completion of the reaction was confirmed by TLC. Then, the reaction solution was purified with a silica gel column (5 g, 30%-+50% ethyl acetate/n-hexane) to obtain the amorphous compound (148 mg).

$^1$H-NMR (400 MHz, CDCl$_3$) 7.52-6.59 (17H, m), 3.79 (6H, s), 3.05-3.01 (2H, m), 2.31-2.27 (2H, m), 1.71-1.58 (4H, m), 1.35-1.24 (6H, m)

FAB-MAS (mNBA+KI): 592 (M+K)$^+$

Reference Example 5

10-(4,4'-dimethoxytrityloxy)decanoic acid (0.707 g, 1.19 mmol; Tetrahedron Letters, 1994, 35, 2353-2356) was dissolved in 2 mL of methylene chloride. To the solution, 4-aminophenol (141.8 mg, 1.28 mmol), EDC (203 mg, 1.76 mmol), HOBT (158 mg, 1.76 mmol), and triethylamine (183 L) were added, and the mixture was stirred overnight. The completion of the reaction was confirmed by TLC. Then, the reaction solution was purified with a silica gel column (7.5 g, 30%→50% ethyl acetate/n-hexane) to obtain the amorphous compound (485 mg).

$^1$H-NMR (400 MHz, CDCl$_3$) 7.52-6.59 (17H, m), 3.78 (6H, s), 3.04-3.01 (2H, m), 2.32-2.29 (2H, m), 1.74-1.56 (4H, m), 1.33-1.24 (10H, m)

FAB-MAS (mNBA): 580 (M–H)$^+$

Reference Example 6

A solution of EDC (383 mg, 2 mmol) and HOBT (67.5 mg, 0.5 mmol) dissolved in 3 mL of methylene chloride was added to 4-amino-1-butanol (160.45 mg, 1.8 mmol) and 4-hydroxybenzoic acid (207.18 mg, 1.5 mmol). Triethylamine (260 L) was further added thereto, and the mixture was shaken overnight. The completion of the reaction was confirmed by TLC. Then, the reaction solution was purified with a silica gel column (5 g, elution with methylene chloride→ethyl acetate) to obtain an amide compound in an oil form (0.20 g). This compound was dissolved in 1.5 mL of pyridine. To the solution, 4,4'-dimethoxytrityl chloride (500 mg, 1.5 mmol) was added, and the mixture was stirred at room temperature for 3 hours. The completion of the reaction was confirmed by TLC. Then, 0.5 mL of methanol was added thereto, and the reaction solution was separated into organic and aqueous phases using ethyl acetate and a 5% aqueous sodium bicarbonate solution. The solvent in the organic phase was concentrated under reduced pressure. The residue was purified with a silica gel column (10 g, 40%-+50% ethyl acetate/n-hexane) to obtain the amorphous compound (325 mg).

$^1$H-NMR (400 MHz, CDCl$_3$) 7.70-6.78 (17H, m), 6.11 (1H, brs), 5.69 (1H, s), 3.78 (6H, s), 3.44-3.41 (2H, m), 3.13-3.10 (2H, m), 1.70-1.69 (4H, m)

FAB-MAS (mNBA): 511 M$^+$

Reference Example 7

The amorphous compound was obtained (445 mg) by synthesis in the same way as for Reference Example 6 using 6-amino-1-hexanol (210.94 mg, 1.8 mmol) and 4-hydroxybenzoic acid (207.18 mg, 1.5 mmol).

$^1$H-NMR (400 MHz, CDCl$_3$) 7.67-6.79 (17H, m), 5.97 (1H, brs), 5.56 (1H, s), 3.78 (6H, s), 3.43-3.38 (2H, m), 3.06-3.02 (2H, m), 1.63-1.55 (4H, m), 1.45-1.34 (4H, m)

FAB-MAS (mNBA): 539 M$^+$

Reference Example 8

The amorphous compound was obtained (486 mg) by synthesis in the same way as for Reference Example 6 using 8-amino-1-octanol (261.43 mg, 1.8 mmol) and 4-hydroxybenzoic acid (207.18 mg, 1.5 mmol).

$^1$H-NMR (400 MHz, CDCl$_3$) 7.68-6.80 (17H, m), 5.98 (1H, brs), 5.54 (1H, s), 3.79 (6H, s), 3.44-3.39 (2H, m), 3.04-3.01 (2H, m), 1.62-1.55 (4H, m), 1.34-1.24 (8H, m)

FAB-MAS (mNBA): 567 M$^+$

Reference Example 9

The amorphous compound was obtained (566 mg) by synthesis in the same way as for Reference Example 6 using 4-amino-1-butanol (160.45 mg, 1.8 mmol) and 3-hydroxybenzoic acid (207.18 mg, 1.5 mmol).

$^1$H-NMR (400 MHz, CDCl$_3$) 7.52-6.79 (17H, m), 6.25 (1H, brs), 6.06 (1H, s), 3.78 (6H, s), 3.47-3.47-3.42 (2H, m), 3.15-3.12 (2H, m), 1.72-1.66 (4H, m)

FAB-MAS (mNBA): 511 M$^+$

Reference Example 10

The amorphous compound was obtained (580 mg) by synthesis in the same way as for Reference Example 6 using 6-amino-1-hexanol (210.94 mg, 1.8 mmol) and 3-hydroxybenzoic acid (207.18 mg, 1.5 mmol).

$^1$H-NMR (400 MHz, CDCl$_3$) 7.52-6.80 (17H, m), 6.08 (1H, brs), 6.04 (1H, s), 3.78 (6H, s), 3.45-3.40 (2H, m), 3.06-3.03 (2H, m), 1.65-1.56 (4H, m), 1.45-1.34 (4H, m)

FAB-MAS (mNBA): 539 M$^+$

Reference Example 11

The amorphous compound was obtained (675 mg) by synthesis in the same way as for Reference Example 6 using 8-amino-1-octanol (261.43 mg, 1.8 mmol) and 3-hydroxybenzoic acid (207.18 mg, 1.5 mmol).

$^1$H-NMR (400 MHz, CDCl$_3$) 7.52-6.80 (17H, m), 6.21 (1H, brs), 6.11 (1H, s), 3.78 (6H, s), 3.46-3.41 (2H, m), 3.04-3.01 (2H, m), 1.63-1.58 (4H, m), 1.39-1.33 (8H, m)

FAB-MAS (mNBA): 566 (M–H)$^+$

Reference Example 12

The amorphous compound was obtained (540 mg) by synthesis in the same way as for Reference Example 6 using 4-amino-1-butanol (160.45 mg, 1.8 mmol) and 3-(4-hydroxyphenyl)propionic acid (249.26 mg, 1.5 mmol).

$^1$H-NMR (400 MHz, CDCl$_3$) 7.52-6.68 (17H, m), 5.37 (1H, brs), 4.87 (1H, s), 3.79 (6H, s), 3.21-3.16 (2H, m), 3.06-3.03 (2H, m), 2.86 (2H, t, J=7.56 Hz), 2.35 (2H, t, J=7.56 Hz), 1.54-1.48 (4H, m)

FAB-MAS (mNBA): 540 (M+H)$^+$

Reference Example 13

The amorphous compound was obtained (559 mg) by synthesis in the same way as for Reference Example 6 using 6-amino-1-hexanol (210.94 mg, 1.8 mmol) and 3-(4-hydroxyphenyl)propionic acid (249.26 mg, 1.5 mmol).

$^1$H-NMR (400 MHz, CDCl$_3$) 7.44-6.70 (17H, m), 5.21 (1H, brs), 5.03 (1H, s), 3.79 (6H, s), 3.18-3.13 (2H, m), 3.05-3.02 (2H, m), 2.87 (2H, t, J=7.33 Hz), 2.39 (2H, t, J=7.56 Hz), 1.59-1.13 (8H, m)

FAB-MAS (mNBA): 568 (M+H)$^+$

Reference Example 14

The compound having a chewy-candy consistency was obtained (720 mg) by synthesis in the same way as for Reference Example 6 using 8-amino-1-octanol (261.43 mg, 1.8 mmol) and 3-(4-hydroxyphenyl)propionic acid (249.26 mg, 1.5 mmol)

$^1$H-NMR (400 MHz, CDCl$_3$) 7.52-6.71 (17H, m), 5.26 (1H, brs), 5.10 (1H, s), 3.78 (6H, s), 3.20-3.15 (2H, m), 3.05-3.01 (2H, m), 2.88 (2H, t, J=7.56 Hz), 2.41 (2H, t, J=7.56 Hz), 1.62-1.17 (12H, m)

FAB-MAS (mNBA): 594 (M–H)$^+$

Reference Example 15

N-(4-methoxytrityl)-L-tyrosine ethyl ester

L-tyrosine ethyl (418 mg, 2 mmol) was dissolved in 5 mL of pyridine. To the solution, 4-methoxytrityl chloride (741 mg, 2.4 mmol) was added, and the mixture was stirred at room temperature for 5 hours. The completion of the reaction was confirmed by TLC. Then, the reaction solution was separated into organic and aqueous phases using ethyl acetate and a 5% aqueous sodium bicarbonate solution. The organic phase was dried over sodium sulfate, and the solvent was then concentrated under reduced pressure. The residue was purified with a silica gel column (30 g, 30% ethyl acetate/n-hexane) to obtain the amorphous compound (687 mg).

$^1$H-NMR (400 MHz, CDCl$_3$) 7.42-6.72 (18H, m), 4.69 (1H, s), 3.76 (3H, s), 3.53-3.33 (3H, m), 2.94-2.81 (2H, m), 2.58 (1H, d), 0.88-0.85 (3H, m)

FAB-MAS (mNBA): 482 (M+H)$^+$

Reference Example 16

3-(4-methoxytrityloxy)-2-acetylamino-propionic acid (Ac-Ser(MMTr)-OH)

N-acetyl-D,L-serine (1.775 g, 12 mmol) was dissolved in 20 mL of pyridine. To the solution, 4-methoxytrityl chloride (4.1 g, 13.2 mmol) was added, and the mixture was stirred overnight at room temperature. The completion of the reaction was confirmed by TLC. Then, the reaction solution was separated into organic and aqueous phases using ethyl acetate and a 5% aqueous sodium bicarbonate solution. The organic phase was dried over sodium sulfate, and the solvent was then concentrated under reduced pressure. The residue was purified with a silica gel column (120 g, 30% acetone/n-hexane) to obtain the amorphous compound (3.93 g).

$^1$H-NMR (400 MHz, CDCl$_3$) 7.41-6.81 (14H, m), 6.15 (1H, d, J=7.33 Hz), 4.70-4.66 (1H, m), 3.78 (3H, s), 3.77-3.73 (1H, m), 3.42-3.38 (1H, m), 2.02 (3H, s)

FAB-MAS (mNBA): 419 M$^+$

Reference Example 17

Ac-Ser(MMTr)-Tyr-OEt

The compound of Reference Example 16 (629 mg, 1.5 mmol Ac-Ser(MMTr)-OH) was dissolved in 3 mL of methylene chloride. To the solution, L-tyrosine ethyl (334 mg, 1.6 mmol), EDC (383 mg, 2 mmol), HOBT (67.5 mg, 0.5 mmol), and triethylamine (260 μL) were added, and the mixture was stirred for 4 hours. The reaction solution was purified with a silica gel column (15 g, 40%→50% ethyl acetate/n-hexane) to obtain the amorphous compound (460 mg).

$^1$H-NMR (400 MHz, CDCl$_3$) 7.40-6.61 (18H, m), 6.11-6.06 (1H, m), 4.87-4.77 (1H, m), 4.56-4.48 (1H, m), 4.19-4.05 (2H, m), 3.79, 3.78 (3H, ds), 3.73-3.59 (1H, m), 3.19-2.96 (3H, m), 1.93, 1.91 (1H, ds), 1.28-1.22 (3H, m)

FAB-MAS (mNBA): 611 (M+H)$^+$

Reference Example 18 t-Boc-βAla-Tyr-OEt

The amorphous compound was obtained (497 mg) by synthesis in the same way as for Reference Example 17 using N-t-Boc-β-alanine (283 mg, 1.5 mmol, t-Boc-βAla-OH) and L-tyrosine ethyl (376 mg, 1.8 mmol, H-Tyr-OEt).

$^1$H-NMR (400 MHz, CDCl$_3$) 6.97-6.74 (4H, m), 6.03 (1H, brs), 5.11 (1H, brs), 4.80 (1H, q, J=6.72 Hz), 4.22-4.15 (2H, m), 3.37-3.36 (2H, m), 3.10-3.01 (2H, m), 2.38 (2H, m), 1.41 (9H, s), 1.29-1.23 (3H, m)

FAB-MAS (mNBA): 381 (M+H)$^+$

Reference Example 19 t-Boc-Ala-Tyr-OEt

The amorphous compound was obtained (490 mg) by synthesis in the same way as for Reference Example 17 using N-t-Boc-alanine (283 mg, 1.5 mmol, t-Boc-Ala-OH) and L-tyrosine ethyl (376 mg, 1.8 mmol).

$^1$H-NMR (400 MHz, CDCl$_3$) 6.98-6.71 (4H, m), 6.49 (1H, d), 5.16 (1H, s), 4.95-4.76 (1H, m), 4.20-4.13 (3H, m), 3.11-2.99 (2H, m), 1.41 (9H, s), 1.33, 1.31 (3H, ds), 1.28-1.21 (3H, m)

FAB-MAS (mNBA): 381 (M+H)$^+$

Reference Example 20 t-Boc-Gly-Tyr-OEt

The amorphous compound was obtained (434 mg) by synthesis in the same way as for Reference Example 17 using N-t-Boc-glycine (263 mg, 1.5 mmol) and L-tyrosine ethyl (376 mg, 1.8 mmol).

$^1$H-NMR (400 MHz, CDCl$_3$) 6.98-6.72 (4H, m), 6.46 (1H, d), 5.06 (1H, brs), 4.84-4.79 (1H, m), 4.21-4.13 (2H, m), 3.85-3.72 (2H, m), 3.10-3.01 (2H, m), 1.41 (9H, s), 1.29-1.24 (3H, m), 1.28-1.21 (3H, m)

FAB-MAS (mNBA): 367 (M+H)$^+$

Reference Example 21

Ac-Ser (MMTr)-βAla-Tyr-OEt

The compound obtained in Reference Example 18 (490 mg, 1.29 mmol) was dissolved in 4 mL of methylene chloride. To the solution, 4 mL of TFA was added, and the mixture was left at room temperature for 15 minutes. Then, the solvent was concentrated under reduced pressure. The residue was dissolved in methylene chloride (3 mL) and triethylamine (260 L). To the solution, the compound obtained in Reference Example 16 (544 mg, 1.3 mmol), EDC (383 mg, 2 mmol), HOBT (67.5 mg, 0.5 mmol), and triethylamine (260 L) were added, and the mixture was stirred overnight. The reaction solution was purified with a silica gel column (20 g, 80% ethyl acetate/n-hexane→ethyl acetate) to obtain the amorphous compound (469 mg).

$^1$H-NMR (400 MHz, CDCl$_3$) 7.41-6.71 (18H, m), 4.91-4.75 (1H, m), 4.54-4.44 (1H, m), 4.26-4.15 (2H, m), 3.78 (3H, s), 3.46-2.20 (8H, m), 2.02, 1.98 (3H, ds), 1.34-1.24 (3H, m)

FAB-MAS (mNBA): 682 (M+H)$^+$

Reference Example 22

Ac-Ser (MMTr)-Ala-Tyr-OEt

The compound in a white solid form was obtained (448 mg) by synthesis in the same way as for Reference Example 21 using the compound of Reference Example 19 (485 mg, 1.26 mmol) and the compound obtained in Reference Example 16 (544 mg, 1.3 mmol).

$^1$H-NMR (400 MHz, CDCl$_3$) 7.41-6.49 (18H, m), 4.81-4.71 (1H, m), 4.56-4.43 (2H, m), 4.21-4.11 (2H, m), 3.79, 3.78 (3H, ds), 3.46-2.83 (4H, m), 2.01, 1.94 (3H, ds), 1.37-1.17 (6H, m)

FAB-MAS (mNBA): 682 (M+H)$^+$

Reference Example 23

Ac-Ser(MMTr)-Gly-Tyr-OEt

The compound in a white solid form was obtained (486 mg) by synthesis in the same way as for Reference Example 21 using the compound obtained in Reference Example 20 (430 mg, 1.17 mmol) and the compound obtained in Reference Example 16 (544 mg, 1.3 mmol).

$^1$H-NMR (400 MHz, DMSO-d$_6$) 9.22 (1H, s), 8.41-8.34 (1H, m), 8.24-8.20 (1H, m), 8.08-8.05 (1H, m), 7.38-6.63 (18H, m), 4.62-4.58 (1H, m), 4.39-4.33 (1H, m), 4.04-3.97 (2H, m), 3.92-3.61 (2H, m), 3.74 (3H, s), 3.09-3.08 (1H, m), 2.86-2.50 (1H, m), 1.85 (3H, s), 1.11-1.06 (3H, m)

FAB-MAS (mNBA): 668 (M+H)$^+$

Reference Example 24

The amorphous compound was obtained (568 mg) by synthesis in the same way as for Reference Example 6 using 10-amino-1-decanol (260 mg, 1.5 mmol) and 4-hydroxybenzoic acid (299 mg, 1.8 mmol).

$^1$H-NMR (400 MHz, CDCl$_3$) 7.67-6.80 (17H, m), 6.01-5.99 (2H, m), 3.78 (6H, s), 3.45-3.40 (2H, m), 3.02 (2H, t, J=6.64 Hz), 1.63-1.24 (14H, m)

FAB-MAS (mNBA): 595 M$^+$

Reference Example 25

The compound having a chewy-candy consistency was obtained (411 mg) by synthesis in the same way as for Reference Example 6 using 10-amino-1-decanol (260 mg, 1.5 mmol) and 3-(4-hydroxyphenyl)propionic acid (249 mg, 1.8 mmol).

$^1$H-NMR (400 MHz, CDCl$_3$) 7.45-6.71 (17H, m), 5.27 (1H, brs), 5.03 (1H, s), 3.79 (6H, s), 3.21-3.16 (2H, m), 3.03 (2H, t, J=6.64 Hz), 2.88 (2H, t, J=7.56 Hz), 2.41 (2H, t, J=7.56 Hz), 1.62-1.17 (14H, m)

FAB-MAS (mNBA): 646 (M+Na)$^+$

Reference Example 26

The compound having a chewy-candy consistency was obtained (489 mg) by synthesis in the same way as for Reference Example 6 using 8-amino-1-octanol (218 mg, 1.5 mmol) and (4-hydroxyphenoxy)acetic acid (303 mg, 1.8 mmol).

$^1$H-NMR (400 MHz, CDCl$_3$) 7.45-6.74 (17H, m), 6.56 (1H, brs), 4.95 (1H, s), 4.46 (2H, s), 3.79 (6H, s), 3.34-3.29 (2H, m), 3.03 (2H, t, J=6.64 Hz), 1.63-1.24 (12H, m)

FAB-MAS (mNBA): 596 (M−H)$^+$

Reference Example 27

The compound having a chewy-candy consistency was obtained (579 mg) by synthesis in the same way as for Reference Example 6 using 10-amino-1-decanol (260 mg, 1.5 mmol) and (4-hydroxyphenoxy)acetic acid (303 mg, 1.8 mmol).

$^1$H-NMR (400 MHz, CDCl$_3$) 7.45-6.75 (17H, m), 6.56 (1H, brs), 5.02 (1H, s), 4.42 (2H, s), 3.79 (6H, s), 3.35-3.30 (2H, m), 3.03 (2H, t, J=6.64 Hz), 1.63-1.24 (14H, m)

FAB-MAS (mNBA): 624 (M−H)$^+$

Reference Example 28

The amorphous compound was obtained (520 mg) by synthesis in the same way as for Reference Example 6 using (PEO)$_3$-mono-amine (CHEM-IPEX INTERNATIONAL, 224 mg, 1.5 mmol) and 4-hydroxybenzoic acid (299 mg, 1.8 mmol).

$^1$H-NMR (400 MHz, CDCl$_3$) 7.58-6.64 (17H, m), 6.61 (1H, brs), 5.81 (1H, s), 3.78 (6H, s), 3.71-3.60 (10H, m), 3.23 (2H, t, J=5.27 Hz)

FAB-MAS (mNBA): 571 M$^+$

Reference Example 29

The compound having a chewy-candy consistency was obtained (543 mg) by synthesis in the same way as for Reference Example 6 using (PEO)$_3$-mono-amine (CHEM-IPEX INTERNATIONAL, 224 mg, 1.5 mmol) and 3-(4-hydroxyphenyl)propionic acid (249 mg, 1.8 mmol).

$^1$H-NMR (400 MHz, CDCl$_3$) 7.46-6.68 (17H, m), 5.88 (1H, brs), 5.30 (1H, s), 3.77 (6H, s), 3.67-3.64 (4H, m), 3.58-3.56 (2H, m), 3.51-3.47 (2H, m), 3.43-3.38 (2H, m), 3.26-3.23 (2H, m), 2.83-2.81 (2H, m), 2.27 (2H, t, J=7.79 Hz)

FAB-MAS (mNBA): 622 (M+Na)$^+$

Reference Example 30

The compound having a chewy-candy consistency was obtained (471 mg) by synthesis in the same way as for Reference Example 6 using (PEO)$_3$-mono-amine (CHEM-IPEX INTERNATIONAL, 224 mg, 1.5 mmol) and (4-hydroxyphenoxy)acetic acid (303 mg, 1.8 mmol).

$^1$H-NMR (400 MHz, CDCl$_3$) 7.52-6.68 (18H, m), 5.05 (1H, s), 4.39 (2H, s), 3.78 (6H, s), 3.67-3.51 (10H, m), 3.23 (2H, t, J=5.27 Hz)

FAB-MAS (mNBA): 600 (M−H)$^+$

Reference Example 31

The amorphous compound was obtained (358 mg) by synthesis in the same way as for Reference Example 6 using 8-amino-1-octanol (218 mg, 1.5 mmol) and N-[(9H-fluorene-9-ylmethoxy)carbonyl]-L-tyrosine (N-Fmoc-L-tyrosine, 726 mg, 1.8 mmol).

$^1$H-NMR (400 MHz, CDCl$_3$) 7.77-6.71 (25H, m), 5.46 (1H, brs), 5.39 (1H, brs), 5.06 (1H, s), 4.43-4.18 (4H, m), 3.78 (6H, s), 3.12-3.02 (6H, m), 1.62-1.12 (12H, m)

FAB-MAS (mNBA): 833 M$^+$

Reference Example 32

Synthesis of HO-G$^{rp}$-C$^{rp}$-A$^{rp}$-C$^{rp}$-A$^{rp}$-A$^{rp}$-G$^{rp}$-A$^{rp}$-A$^{rp}$-U$^{rp}$-G$^{rp}$-G$^{rp}$-A$^{rp}$-U$^{rp}$-C$^{rp}$-A$^{rp}$-C$^{rp}$-A$^{rp}$-A$^{rp}$-U$^{rp}$-U$^{rt}$-H (SEQ ID NO: 7 of the Sequence Listing) (CT-106)

CT-106 was synthesized in the same way as for Reference Example 1. However, the protected polynucleotide analog having the sequence of interest was treated with 2 mL of an ammonia water:ethanol solution (3:1 v/v) at 55° C. for 16 hours to excise the oligomer from the support and to remove the cyanoethyl group acting as a protective group for the phosphate group and the protective group on the nucleobase. CPG was removed by filtration. After washing with ethanol, the filtrate and the wash were combined, and the solvent was distilled off under reduced pressure. To the residue, 0.3 mL of triethylamine trihydrofluoride was added, and the mixture was left at room temperature for 19 hours, followed by purification. The structure of CT-106 is shown in FIG. 13. Molecular weight: calculated value: 6727.16, measured value: 6726.73

Nucleotide sequence: comprising a sequence of nucleotide Nos. 3139-3157 of the human β-catenin gene (GenBank accession No. NM_001904.3)

Reference Example 33

Synthesis of HO—U$^{rp}$-U$^{rp}$-G$^{rp}$-U$^{rp}$-G$^{rp}$-A$^{rp}$-U$^{rp}$-C$^{rp}$-C$^{rp}$-A$^{rp}$-U$^{rp}$-U$^{rp}$-C$^{rp}$-U$^{rp}$-U$^{rp}$-G$^{rp}$-U$^{rp}$-G$^{rp}$-C$^{rp}$-U$^{rp}$-U$^{rt}$-H (SEQ ID NO: 8 of the Sequence Listing) (CT-041)

CT-041 was synthesized in the same way as for Reference Example 32. The structure of CT-041 is shown in FIG. 13.

Molecular weight: calculated value: 6565.88, measured value: 6565.34

Nucleotide sequence: comprising a sequence complementary to nucleotide Nos. 3139-3157 of the human 3-catenin gene (GenBank accession No. NM_001904.3)

Reference Example 34

CT-001

Synthesis of HO-G$^{rp}$-C$^{m1p}$-A$^{rp}$-C$^{m1p}$-A$^{rp}$-A$^{m1p}$-G$^{rp}$-A$^{m1p}$-A$^{rp}$-U$^{m1p}$-G$^{rp}$-G$^{m1p}$-A$^{rp}$-U$^{m1p}$-C$^{rp}$-A$^{m1p}$-C$^{rp}$-A$^{m1p}$-A$^{rp}$-T$^p$-T$^t$-H (SEQ ID NO: 9 of the Sequence Listing) (CT-001)

CT-001 was synthesized in the same way as for Reference Example 32. The structure of CT-001 is shown in FIG. 13.

Molecular weight: calculated value: 6849.46, measured value: 6850.8

Nucleotide sequence: comprising a sequence of nucleotide Nos. 3139-3157 of the human β-catenin gene (GenBank accession No. NM_001904.3)

Reference Example 35

CT-005

Synthesis of HO—U$^{m1p}$-U$^{rp}$-G$^{m1p}$-U$^{rp}$-G$^{m1p}$-A$^{rp}$-U$^{m1p}$-C$^{rp}$-C$^{m1p}$-A$^{rp}$-U$^{m1p}$-U$^{rp}$-C$^{m1p}$-U$^{rp}$-U$^{m1p}$-G$^{rp}$-U$^{m1p}$-G$^{rp}$-C$^{m1p}$-T$^p$-T$^t$-H (SEQ ID NO: 10 of the Sequence Listing) (CT-005)

CT-005 was synthesized in the same way as for Reference Example 32. The structure of CT-005 is shown in FIG. 13.

Molecular weight: calculated value: 6702.20, measured value: 6702.2

Nucleotide sequence: comprising a sequence complementary to nucleotide Nos. 3139-3157 of the human 3-catenin gene (GenBank accession No. NM_001904.3)

83

Figure 5:
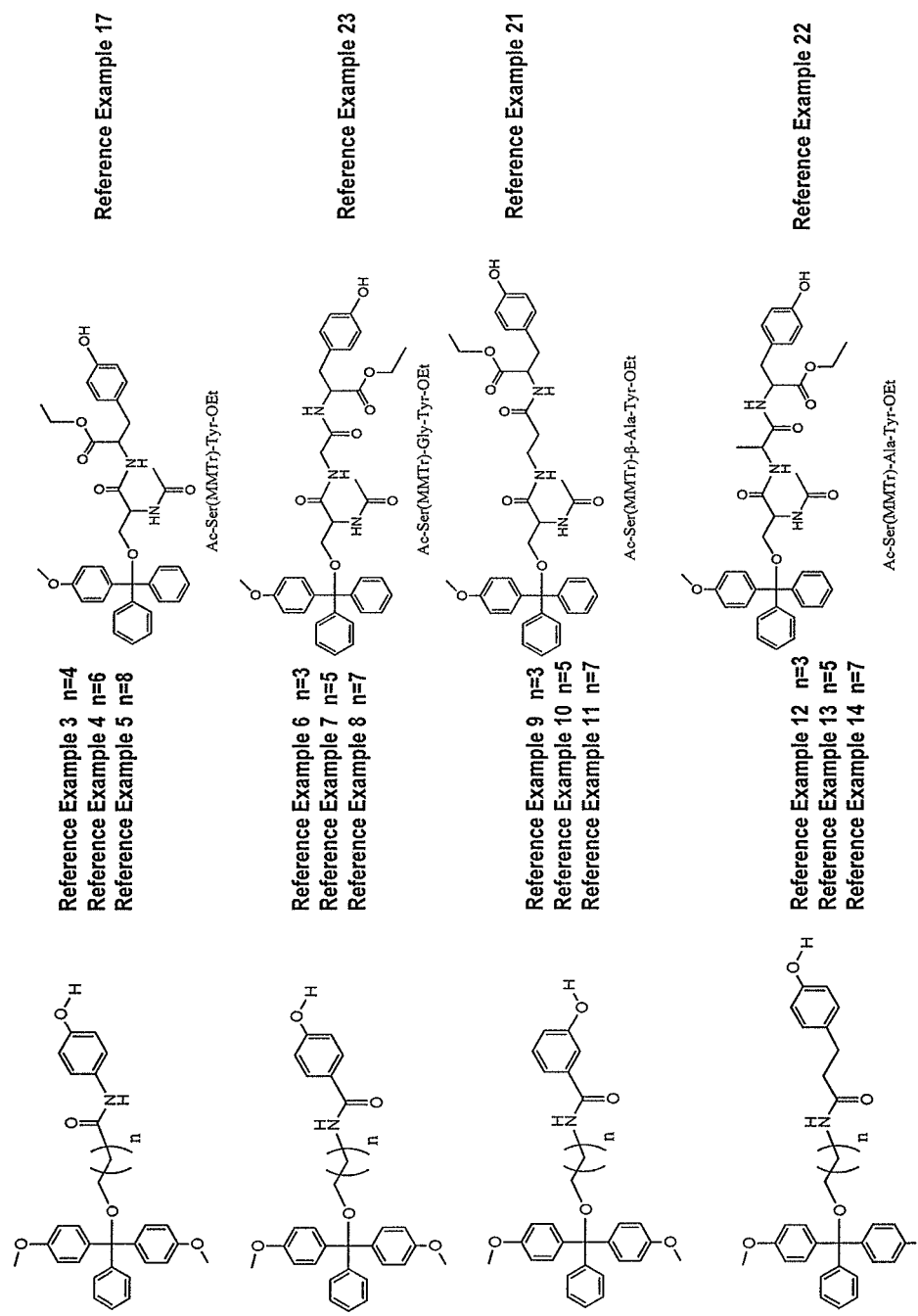
FIG. 5 is a diagram showing the structures of compounds described in Reference Examples 3 to 14, 17, and 21 to 23.
Figure 10:
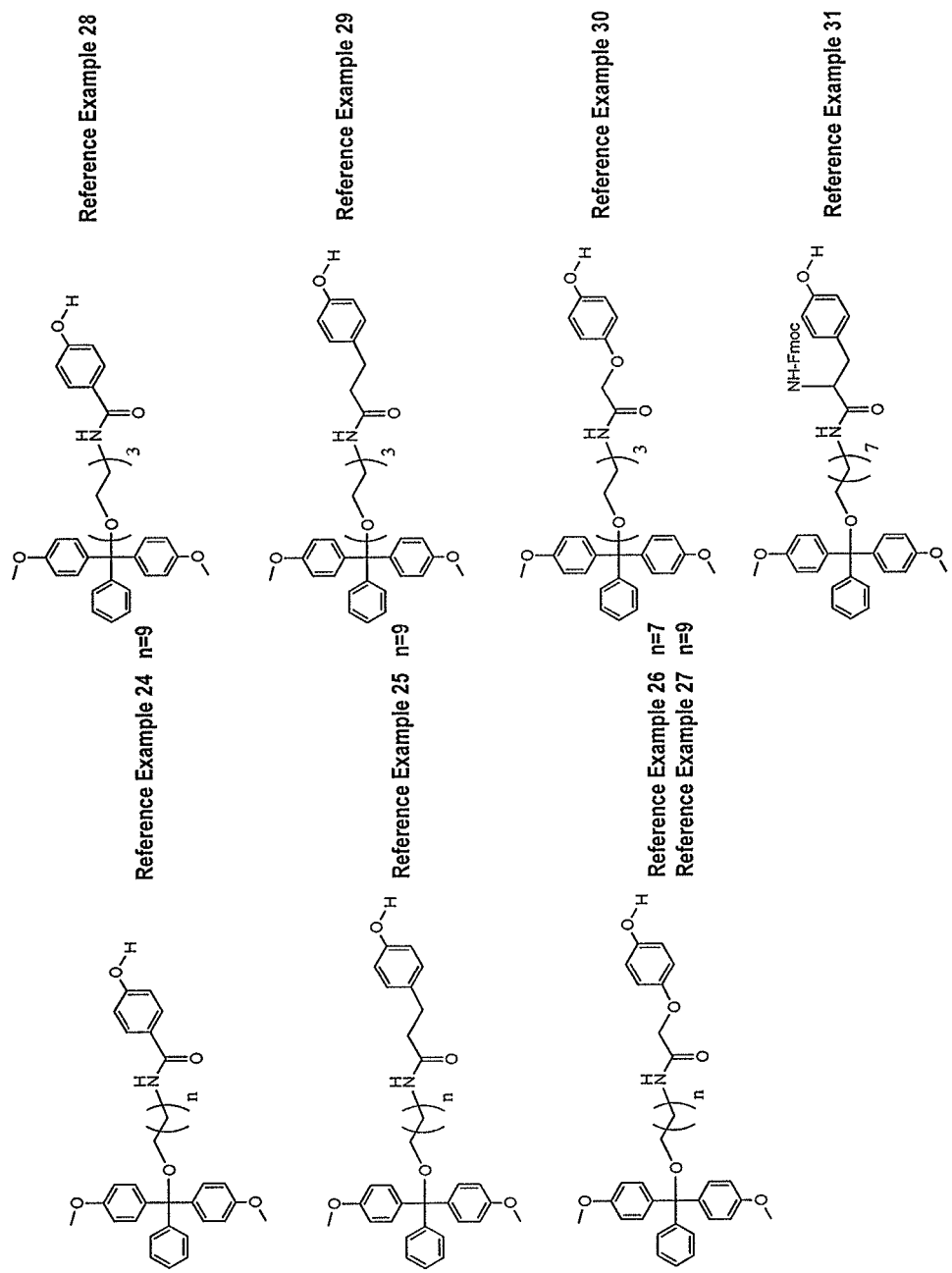
FIG. 10 is a diagram showing the structures of compounds described in Reference Examples 24 to 31.

The structures of the compounds described in Reference Examples 3 to 14, 17, and 21 to 23 are shown in FIG. 5. The structures of the compounds described in Reference Examples 24 to 31 are shown in FIG. 10.

Example 27

Annealing for Formation of Double-Strand Structure

Each of sense and antisense strands was placed in the combinations of the above Reference Examples 1 and 2 into one tube at concentrations of 300 µmol and dried under reduced pressure. 30 µL of an siRNA suspension buffer (QIAGEN) was added thereto, and the mixture was heated at 65° C. for 1 minute and then left at room temperature for 5 minutes for annealing of the sense and antisense strands to obtain a 10 µM double-stranded polynucleotide solution.

Each double-stranded polynucleotide may be indicated only in the combination of sense and antisense strands, i.e., for example, the double-stranded polynucleotide consisting of the combination CT-169/CT-157 may be simply referred to as "CT-169/CT-157" or "CT169/157".)

Double-stranded polynucleotides and 3L5-polynucleotides in which the 5'-end of the antisense strand and the 3'-end of the sense strand are linked via a linker through phosphodiester bonds can be obtained by the present methods, as shown in FIGS. 6 and 7.

Test Example 1

The intensity of human β-catenin gene expression inhibitory activity was compared among single-stranded or double-stranded polynucleotides as follows.

(1) Transfection

A human colon cancer SW480 cell strain (derived from human adenocarcinoma of the large intestine) was adjusted to a concentration of 100000 cells/mL in an RPMI1640 medium (manufactured by Invitrogen Corp.) containing 10% fetal bovine serum. Then, the solution was seeded at a concentration of 1 mL/well onto a 12-well flat-bottomed plate (manufactured by Corning Inc.) and cultured at 37° C. for 1 day under 5.0% $CO_2$ gas. 7.5 µL of a lipofection reagent Lipofectamine RNAiMAX (manufactured by Invitrogen Corp.) and a single-stranded or double-stranded polynucleotide solution at a final concentration of 0.3, 0.03, or 0.003 nM were mixed in an OPTI-MEM medium and left standing at room temperature for 20 minutes. The mixture was added to each well, and the culture was further continued for 3 days.

(2) Real-Time PCR

After the transfection, the culture supernatant was removed from each well, and mRNA was extracted using RNeasy Mini kit (manufactured by QIAGEN). cDNA was prepared from 0.5 g of RNA using the obtained mRNA and iScript™ cDNA Synthesis kit (manufactured by QIAGEN) according to the description of the instruction. Next, the mRNA was quantified by real-time PCR as follows using PCR primers for the human β-catenin gene (primer set ID: HA135664, manufactured by TAKARA BIO INC.), PCR primers for the human GAPDH gene (primer set ID: HA067812, manufactured by TAKARA BIO INC.) as an internal standard, and a real-time PCR kit (manufactured by QIAGEN) containing reagents necessary for PCR.

84

```
β-catenin gene ID: HA135664
Forward primer
                                  (SEQ ID NO: 11)
5'-TCTGAGGACAAGCCACAAGATTACA-3'

Reverse primer
                                  (SEQ ID NO: 12)
5'-TGGGCACCAATATCAAGTCCAA-3'

GAPDH gene ID: HA067812
Forward primer
                                  (SEQ ID NO: 13)
5'-GCACCGTCAAGGCTGAGAAC-3'

Reverse primer
                                  (SEQ ID NO: 14)
5'-TGGTGAAGACGCCAGTGGA-3'
```

25 µL of 2× QuantiTect SYBR GREEN PCR Master Mix included in the real-time PCR kit, 18 µL of RNase-Free Water, 5 µL each PCR primer (final concentration: 0.3 µM), and 2 µL of the prepared cDNA solution per well of a 96-well PCR plate (manufactured by Applied Biosystems) were added to bring the solution to the total volume of 50 µL. The plate was loaded in Mx3000P (manufactured by STRATAGENE), followed by PCR under the following conditions:

PCR initial activation at 95° C. for 15 minutes

PCR at 94° C. for 15 seconds

56° C. for 30 seconds

72° C. for 30 seconds

This PCR cycle was repeated 40 times. A calibration curve was prepared using 5-fold dilution series of cDNA prepared from mRNA extracted from cells (═NC) treated only with the lipofection reagent. Based on the calibration curve, human β-catenin and human GAPDH in each transfectant were quantified, and a relative amount determined by dividing the amount of the human catenin gene by the amount of human GAPDH was plotted in a graph. Real-time PCR was conducted on N=2, and average thereof is shown in the graph (the structures and nucleotide sequences of the polynucleotides are shown in FIGS. 6 and 7).

(3) Real-Time PCR Analysis (a) Gene Inhibitory Activity Analysis—1—

CT-169/CT-157, CT-437, CT-455, CT-456, CT-446, CT-447, CT-448, CT-449, CT-450, CT-451, CT-452, CT-453, CT-454, and, CT-461 (for their structures, see FIGS. 6 and 7) were examined for their β-catenin gene expression inhibitory activities.

Figure 8:
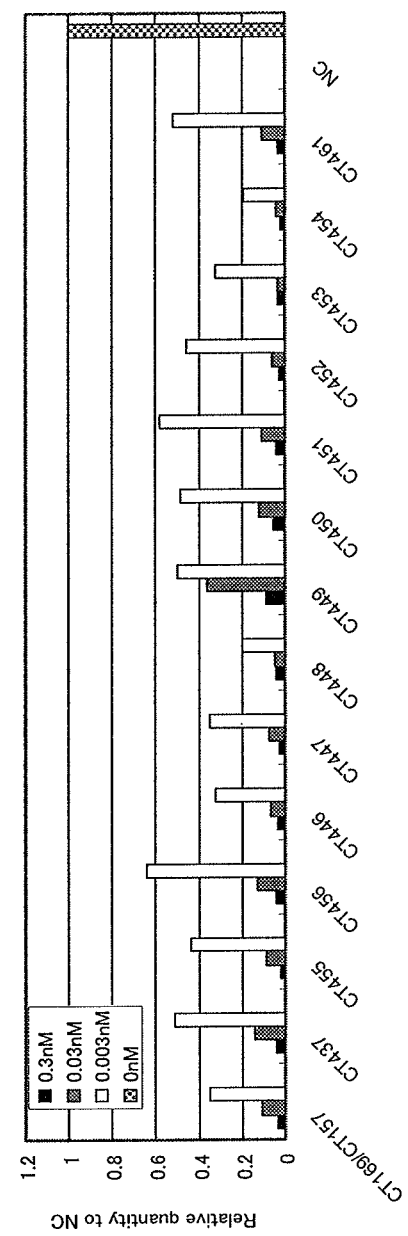
FIG. 8 is a diagram showing the gene inhibitory activities of polynucleotides analyzed by real-time PCR.

As shown in FIG. 8, CT-437, CT-455, CT-456, CT-446, CT-447, CT-448, CT-449, CT-450, CT-451, CT-452, CT-453, CT-454, and, CT-461 strongly inhibited the expression of the β-catenin gene at a level equivalent to CT-169/CT-157. CT-448 and CT-454 exhibited stronger activity than that of CT-169/CT-157. This shows that a single-stranded polynucleotide in which the 5'-end of the antisense strand and the 3'-end of the sense strand are linked via phosphate groups using a modified phenyl group has a strong gene expression inhibitory activity.

Test Example 2

The intensity of human β-catenin gene expression inhibitory activity was compared between single-stranded and double-stranded polynucleotides in the same way as for Test Example 1.

Real-Time PCR Analysis a) Gene Inhibitory Activity Analysis—1—

CT-169/CT-157, CT-460, CT-461, CT-462, and CT-463 (for their structures, see FIG. 7) were examined for their β-catenin gene expression inhibitory activities.

Figure 9:
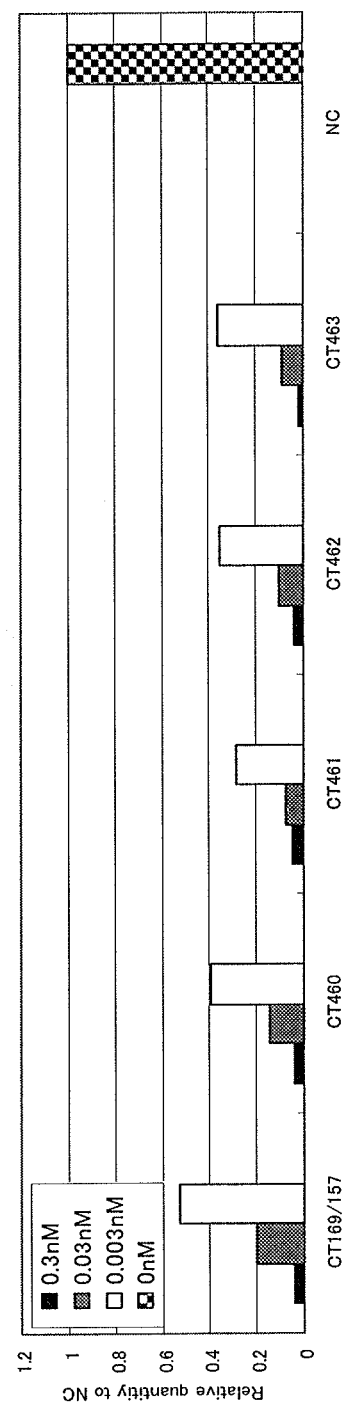
FIG. 9 is a diagram showing the gene inhibitory activities of polynucleotides analyzed by real-time PCR.

As shown in FIG. 9, CT-460, CT-461, CT-462, and CT-463 more strongly inhibited the expression of the β-catenin gene than CT-169/CT-157. This shows that a single-stranded polynucleotide in which the 5'-end of the antisense strand and the 3'-end of the sense strand are linked via phosphate groups using a modified phenyl group has a strong gene expression inhibitory activity.

Test Example 3

The intensity of human β-catenin gene expression inhibitory activity was compared between single-stranded and double-stranded polynucleotides.

(1) Transfection

A human colon cancer SW480 cell strain (derived from human adenocarcinoma of the large intestine) was adjusted to a concentration of 100000 cells/mL in an RPMI1640 medium (manufactured by Invitrogen Corp.) containing 10% fetal bovine serum. Then, the solution was seeded at a concentration of 1 mL/well onto a 12-well flat-bottomed plate (manufactured by Corning Inc.). Next, 7.5 μL of a lipofection reagent Lipofectamine RNAiMAX (manufactured by Invitrogen Corp.) and a single-stranded or double-stranded polynucleotide solution at a final concentration of 0.3, 0.03, or 0.003 nM were mixed in an OPTI-MEM medium and left standing at room temperature for 20 minutes. The mixture was added to each well, and the culture was continued at 37° C. for 3 days under 5.0% $CO_2$ gas.

(2) Real-Time PCR

Real-time PCR was performed in the same way as for Test Example 1.

(3) Real-Time PCR Analysis a) Gene Inhibitory Activity Analysis—1—

CT-169/CT-157, CT-448, CT-454, CT-464, CT-465, CT-466, CT-467, CT-468, CT-469, CT-470, and, CT-471 (for their structures, see FIG. 11) were examined for their β-catenin gene expression inhibitory activities.

Figure 12:
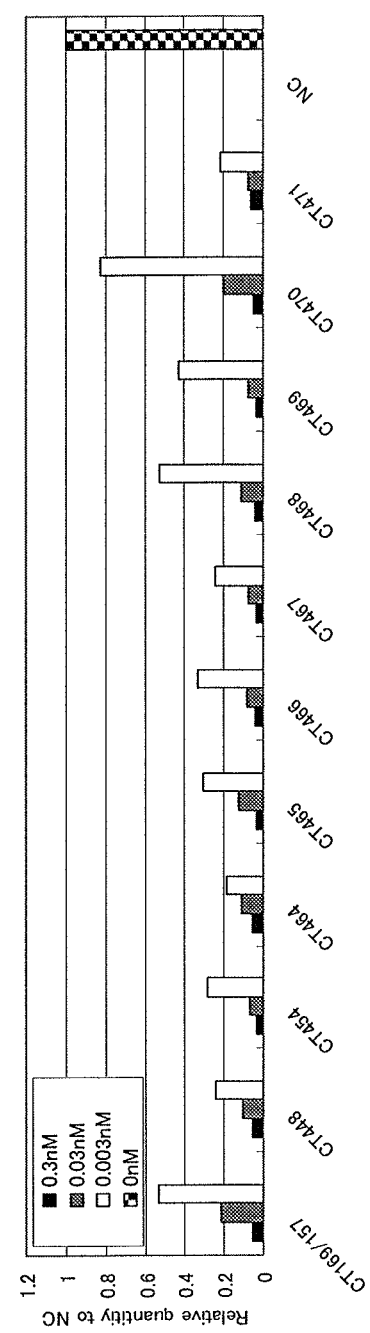
FIG. 12 is a diagram showing the gene inhibitory activities of polynucleotides analyzed by real-time PCR.

As shown in FIG. 12, CT-470 strongly inhibited the expression of the J-catenin gene at a level equivalent to CT-169/CT-157. CT-448, CT-454, CT-464, CT-465, CT-466, CT-467, CT-468, CT-469, and, CT-471 exhibited stronger activity than that of CT-169/CT-157. This shows that a single-stranded polynucleotide in which the 5'-end of the antisense strand and the 3'-end of the sense strand are linked via phosphate groups using a modified phenyl group has a strong gene expression inhibitory activity.

Gene Inhibitory Activity Analysis—2—

CT-106/CT-041 and CT-472 (for their structures, see FIG. 13) were examined for their β-catenin gene expression inhibitory activities.

Figure 14:
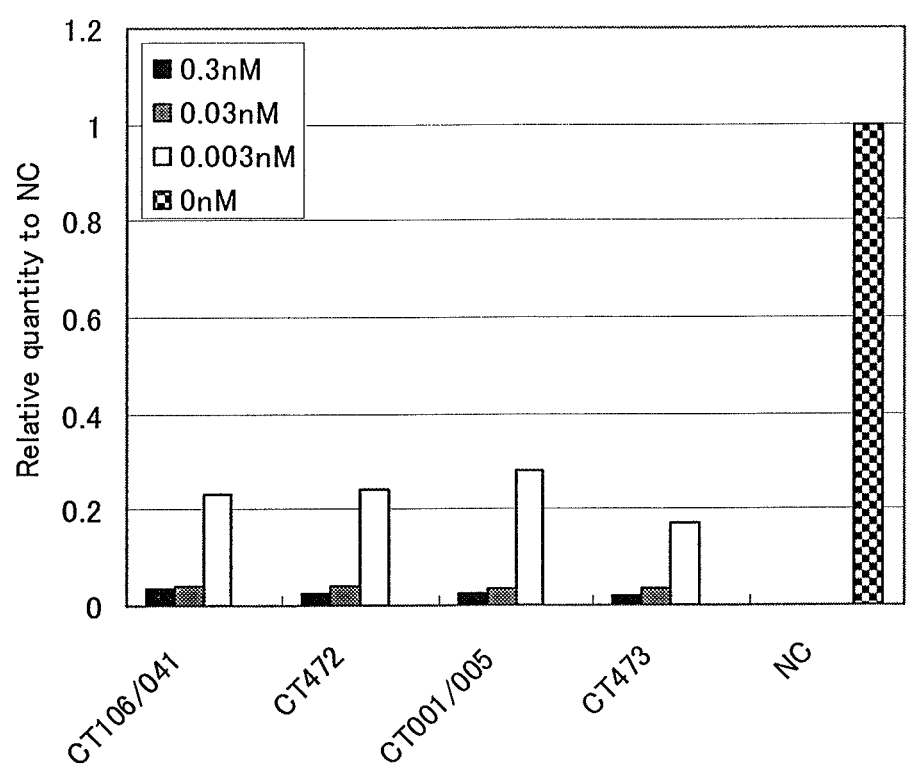
FIG. 14 is a diagram showing the gene inhibitory activities of polynucleotides analyzed by real-time PCR.

As shown in FIG. 14, CT-472 strongly inhibited the expression of the β-catenin gene at a level equivalent to CT-106/CT-041. This shows that a single-stranded polynucleotide in which the 5'-end of the antisense strand and the 3'-end of the sense strand are linked via phosphate groups using a modified phenyl group has a strong gene expression inhibitory activity.

c) Gene Inhibitory Activity Analysis—3—

CT-001/CT-005 and CT-473 (for their structures, see FIG. 13) were examined for their β-catenin gene expression inhibitory activities.

As shown in FIG. 14, CT-473 more strongly inhibited the expression of the β-catenin gene than CT-001/CT-005. This shows that a single-stranded polynucleotide in which the 5'-end of the antisense strand and the 3'-end of the sense strand are linked via phosphate groups using a modified phenyl group has a strong gene expression inhibitory activity.

Example 27

Synthesis of HO-$G^p$-$C^{m1p}$-$T^p$-$C^{m1p}$-$G^p$-$U^{m1p}$-$C^p$-$U^{m1p}$-$A^p$-$U^{m1p}$-$G^p$-$A^{m1p}$-$C^p$-$A^{m1p}$-$A^p$-$G^{m1p}$-$T^p$-$A^{m1p}$-X—P(=O)(OH)—O—$U^{m1p}$-$T^p$-$A^{m1p}$-$C^p$-$U^{m1p}$-$T^p$-$G^{m1p}$-$T^p$-$C^{m1p}$-$A^p$-$U^{m1p}$-$A^p$-$G^{m1p}$-$A^p$-$C^{m1p}$-$G^p$-$A^{m1p}$-$G^p$-$C^{m1p}$-$G^p$-$C^{m1p}$-$T^p$-$U^{m1t}$-H (PK-009)

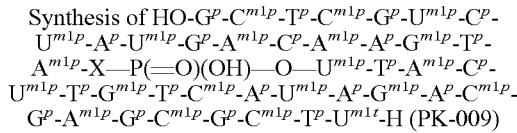

PK-009 was synthesized in the same way as for Example 1. The amidite reagent for the X moiety in the present polynucleotide was prepared using the compound (20 mg) obtained in Reference Example 14.

Figure 15:
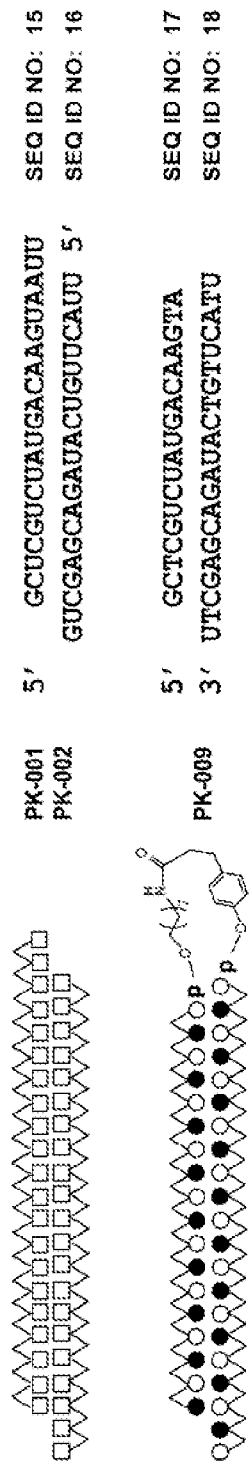
FIG. 15 is a diagram showing polynucleotides corresponding to the mouse PKR gene.

PK-009 is a polynucleotide in which the 3'-terminal nucleotide of the polynucleotide represented by SEQ ID NO: 17 of the Sequence Listing is linked to the 5'-terminal nucleotide of the polynucleotide represented by SEQ ID NO: 18 through phosphodiester bonds with X. The structure of PK-009 is shown in FIG. 15.

Example 28

Synthesis of HO—$C^p$-$G^{m1p}$-A-$G^{m1p}$-$A^p$-$C^{m1p}$-$A^p$-$C^{m1p}$-$A^p$-$U^{m1p}$-$G^p$-$G^{m1p}$-$G^p$-$U^{m1p}$-$G^p$-$C^{m1p}$-$T^p$-$A^{m1p}$-X—P(=O)(OH)—O—$U^{m1p}$-$T^p$-$A^{m1p}$-$G^p$-$C^{m1p}$-$A^p$-$C^{m1p}$-$C^p$-$C^{m1p}$-$A^p$-$U^{m1p}$-$G^p$-$U^{m1p}$-$G^p$-$U^{m1p}$-$C^p$-$U^{m1p}$-$C^p$-$G^{m1p}$-$T^p$-$U^{m1t}$-H (HS-005)

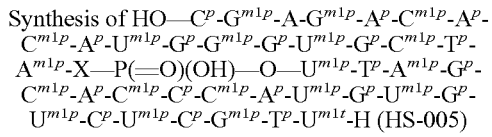

HS-005 was synthesized in the same way as for Example 1. The amidite reagent for the X moiety in the present polynucleotide was prepared using the compound (20 mg) obtained in Reference Example 14.

Figure 16:
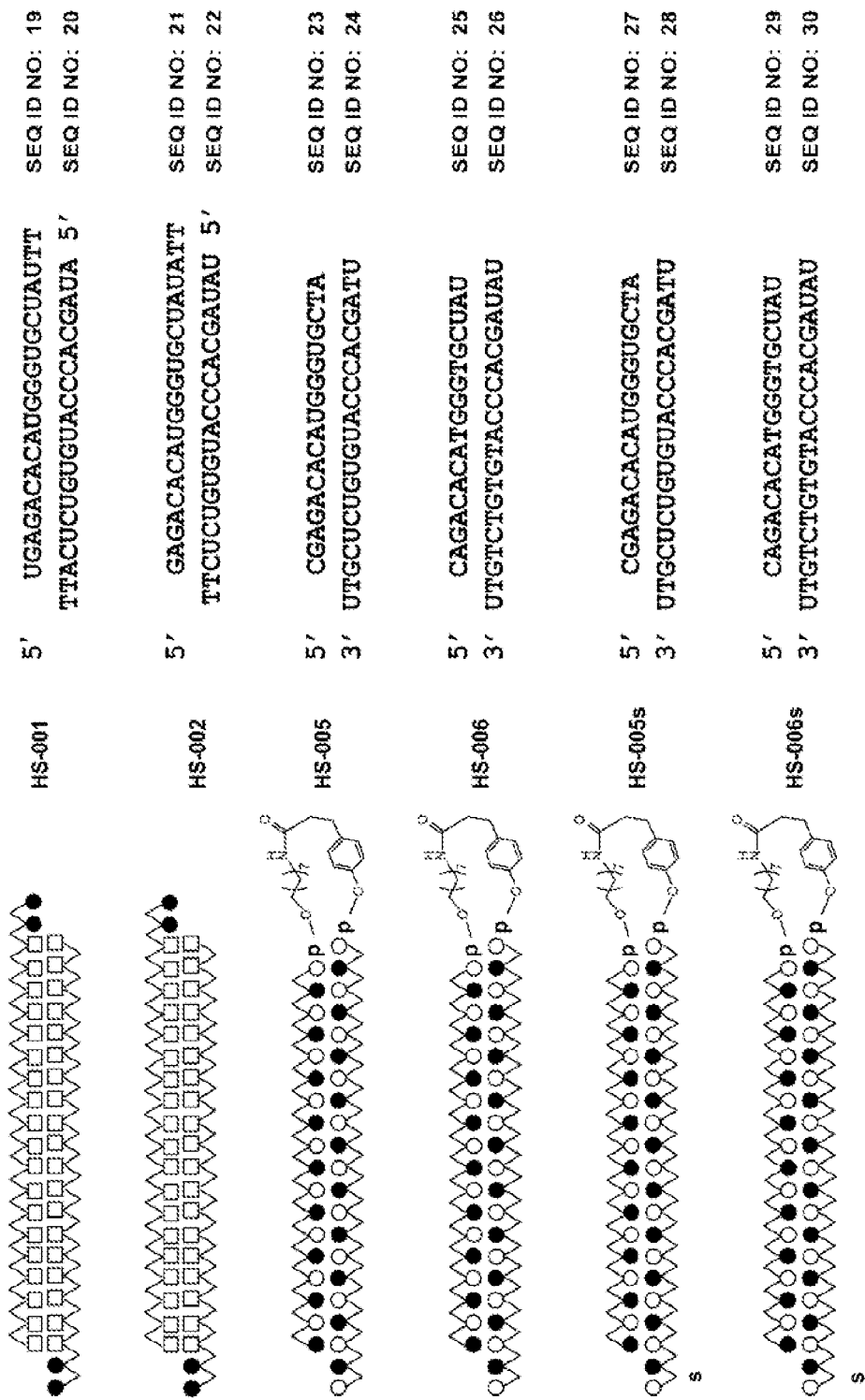
FIG. 16 is a diagram showing polynucleotides corresponding to the rat and human Hsp47 gene. In the diagram, s represents a phosphorothioate bond.

HS-005 is a polynucleotide in which the 3'-terminal nucleotide of the polynucleotide represented by SEQ ID NO: 23 of the Sequence Listing is linked to the 5'-terminal nucleotide of the polynucleotide represented by SEQ ID NO: 24 through phosphodiester bonds with X. The structure of HS-005 is shown in FIG. 16.

Example 29

Synthesis of HO—$C^p$-$A^{m1p}$-$G^p$-$A^{m1p}$-$C^p$-$A^{m1p}$-$C^p$-$A^{m1p}$-$T^p$-$G^{m1p}$-$G^p$-$G^{m1p}$-$T^p$-$G^{m1p}$-$C^p$-$U^{m1p}$-$A^p$-$U^{m1p}$-X—P(=O)(OH)—O—$U^{m1p}$-$A^p$-$U^{m1p}$-$A^p$-$G^{m1p}$-$C^p$-$A^{m1p}$-$C^p$-$C^{m1p}$-$C^p$-$A^{m1p}$-$T^p$-$G^{m1p}$-$T^p$-$G^{m1p}$-$T^p$-$C^{m1p}$-$T^p$-$G^{m1p}$-$T^p$-$U^{m1t}$-H (HS-006)

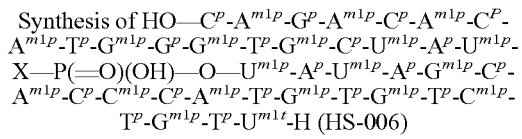

HS-006 was synthesized in the same way as for Example 1. The amidite reagent for the X moiety in the present polynucleotide was prepared using the compound (20 mg) obtained in Reference Example 14.

HS-006 is a polynucleotide in which the 3'-terminal nucleotide of the polynucleotide represented by SEQ ID NO: 25 of the Sequence Listing is linked to the 5'-terminal nucleotide of the polynucleotide represented by SEQ ID NO: 26 through phosphodiester bonds with X. The structure of HS-006 is shown in FIG. 16.

Example 30

Synthesis of HO—$C^p$-$G^{m1p}$-$A^p$-$A^{m1p}$-$A^p$-$C^{m1p}$-$A^p$-$C^{m1p}$-$A^p$-$U^{m1p}$-$G^p$-$G^{m1p}$-$G^p$-$U^{m1p}$-$G^p$-$C^{m1p}$-$T^p$-$A^{m1p}$-X—P(=O)(OH)—O—$U^{m1p}$-$T^p$-$A^{m1p}$-$G^p$-$C^{m1p}$-$A^p$-$C^{m1p}$-$C^p$-$C^{m1p}$-$A^p$-$U^{m1p}$-$G^p$-$U^{m1p}$-$G^p$-$U^{m1p}$-$C^p$-$U^{m1p}$-$C^p$-$G^{m1p}$-$T^s$-$U^{m1t}$-H (HS-005s)

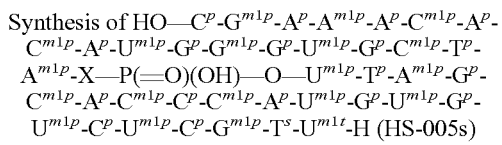

HS-005 was synthesized in the same way as for Example 1. The amidite reagent for the X moiety in the present polynucleotide was prepared using the compound (20 mg) obtained in Reference Example 14. The phosphorothioate bond moiety in the present polynucleotide was prepared by treating with a 0.2 M phenylacetyl disulfide/pyridine-acetonitrile (1:1 v/v) solution for 3 minutes.

HS-005s is a polynucleotide in which the 3'-terminal nucleotide of the polynucleotide represented by SEQ ID NO: 27 of the Sequence Listing is linked to the 5'-terminal nucleotide of the polynucleotide represented by SEQ ID NO: 28 through phosphodiester bonds with X. The structure of HS-005s is shown in FIG. 16.

Example 31

Synthesis of HO—$C^p$-$A^{m1p}$-$G^p$-$A^{m1p}$-$C^p$-$A^{m1p}$-$T^p$-$G^{m1p}$-$G^p$-$G^{m1p}$-$T^p$-$G^{m1p}$-$C^p$-$U^{m1p}$-$A^p$-$U^{m1p}$-X—P(=O)(OH)—O—$U^{m1p}$-$A^p$-$U^{m1p}$-$A^p$-$G^{m1p}$-$C^p$-$A^{m1p}$-$C^p$-$C^{m1p}$-$C^p$-$A^{m1p}$-$T^p$-$G^{m1p}$-$T^p$-$G^{m1p}$-$T^p$-$C^{m1p}$-$T^p$-$G^{m1p}$-$T^s$-$U^{m1t}$-H (HS-006s)

HS-006s was synthesized in the same way as for Example 1. The amidite reagent for the X moiety in the present polynucleotide was prepared using the compound (20 mg) obtained in Reference Example 14. The phosphorothioate bond moiety in the present polynucleotide was prepared by treating with a 0.2 M phenylacetyl disulfide/pyridine-acetonitrile (1:1 v/v) solution for 3 minutes.

HS-006s is a polynucleotide in which the 3-terminal nucleotide of the polynucleotide represented by SEQ ID NO: 29 of the Sequence Listing is linked to the 5'-terminal nucleotide of the polynucleotide represented by SEQ ID NO: 30 through phosphodiester bonds with X. The structure of HS-006s is shown in FIG. 16.

Example 32

Synthesis of HO—$C^p$-$G^{m1p}$-$A^p$-$C^{m1p}$-$A^p$-$G^{m1p}$-$G^p$-$C^{m1p}$-$C^p$-$U^{m1p}$-$C^p$-$U^{m1p}$-$A^p$-$C^{m1p}$-$A^p$-$A^{m1p}$-$C^p$-$U^{m1p}$-X—P(=O)(OH)—O—$U^{m1p}$-$A^p$-$G^{m1p}$-$T^p$-$U^{m1p}$-$G^p$-$U^{m1p}$-$A^p$-$G^{m1p}$-$A^p$-$G^{m1p}$-$G^p$-$C^{m1p}$-$C^p$-$U^{m1p}$-$G^p$-$U^{m1p}$-$C^p$-$G^{m1p}$-$T^p$-$U^{m1t}$-H (HS-012)

HS-012 was synthesized in the same way as for Example 1. The amidite reagent for the X moiety in the present polynucleotide was prepared using the compound (20 mg) obtained in Reference Example 14.

Figure 19:
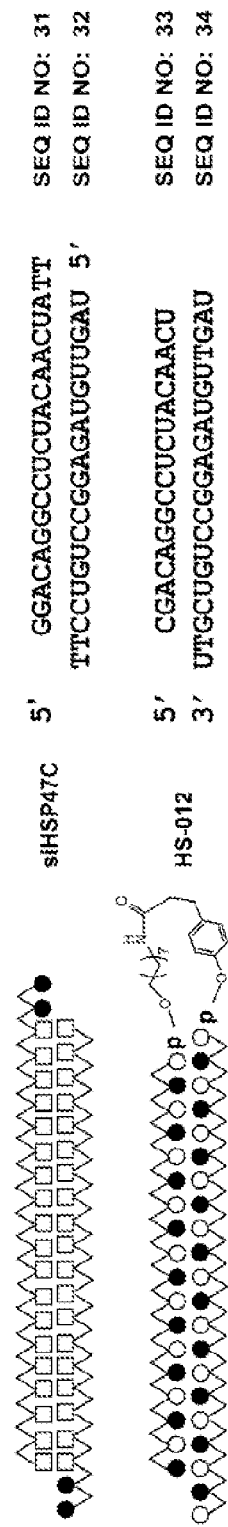
FIG. 19 is a diagram showing polynucleotides corresponding to the rat and human Hsp47 gene.

HS-012 is a polynucleotide in which the 3'-terminal nucleotide of the polynucleotide represented by SEQ ID NO: 33 of the Sequence Listing is linked to the 5'-terminal nucleotide of the polynucleotide represented by SEQ ID NO: 34 through phosphodiester bonds with X. The structure of HS-012 is shown in FIG. 19.

The structures of the X moieties of the polynucleotides described in Examples 27 to 32 and the molecular weights of these polynucleotides are shown in Table 3. In the table, the terminal methylene group of X is bound to the 3'-end of the sense strand polynucleotide to form a phosphodiester bond, while the oxygen atom bonded to the phenyl group is bound to the 5'-end of the antisense strand polynucleotide to form a phosphodiester bond.

TABLE 3

| Example | Name | X | Molecular weight |
|---|---|---|---|
| 27 | PK-009 | 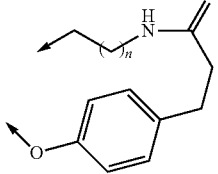 n = 7 | 12829.88 |
| 28 | HS-005 | 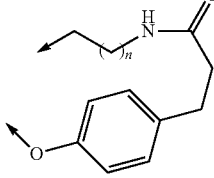 n = 7 | 12817.68 |
| 29 | HS-006 | 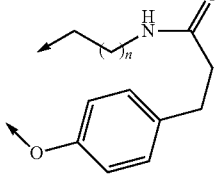 n = 7 | 12859.22 |
| 30 | HS-005s | 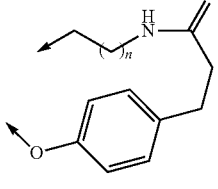 n = 7 | 12834.64 |
| 31 | HS-006s | 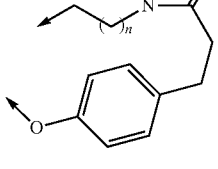 n = 7 | 12875.57 |
| 32 | HS-012 | 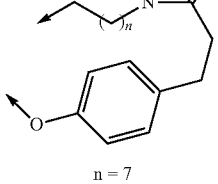 n = 7 | 12803.87 |

Reference Example 36

Synthesis of HO-$G^{rp}$-$C^{rp}$-$U^{rp}$-$C^{rp}$-$G^{rp}$-$U^{rp}$-$C^{rp}$-$U^{rp}$-$A^{rp}$-$U^{rp}$-$G^{rp}$-$A^{rp}$-$C^{rp}$-$A^{rp}$-$A^{rp}$-$G^{rp}U^{rp}$-$A^{rp}$-$A^{rp}$-$U^{rp}$-$U^{rt}$-H (SEQ ID NO: 15 of the Sequence Listing) (PK-001)

PK-001 was synthesized in the same way as for Reference Example 32. The structure of PK-001 is shown in FIG. 15.

Molecular weight: calculated value: 6658.04, measured value: 6658.23

Nucleotide sequence: comprising a sequence of nucleotide Nos. 743-762 of the RNA-dependent protein kinase gene (GenBank accession No. NM_011163)

Reference Example 37

Synthesis of HO-$U^{rp}$-$U^{rp}$-$A^{rp}$-$C^{rp}$-$U^{rp}$-$U^{rp}$-$G^{rp}$-$U^{rp}$-$C^{rp}$-$A^{rp}$-$U^{rp}$-$A^{rp}$-$G^{rp}$-$A^{rp}$-$C^{rp}$-$G^{rp}$-$A^{rp}$-$G^{rp}$-$C^{rp}$-$U^{rp}$-$G^{t}$-H (SEQ ID NO: 16 of the Sequence Listing) (PK-002)

PK-002 was synthesized in the same way as for Reference Example 32. The structure of PK-002 is shown in FIG. 15.

Molecular weight: calculated value: 6674.04, measured value: 6673.91

Nucleotide sequence: comprising a sequence complementary to nucleotide Nos. 743-762 of the RNA-dependent protein kinase gene (GenBank accession No. NM_011163)

Reference Example 38

Synthesis of HO—$U^{rp}$-$G^{rp}$-$A^{rp}$-$G^{rp}$-$A^{rp}$-$C^{rp}$-$A^{rp}$-$C^{rp}$-$A^{rp}$-$U^{rp}$-$G^{rp}$-$G^{rp}$-$G^{rp}$-$U^{rp}$-$G^{rp}$-$C^{rp}$-$U^{rp}$-$A^{rp}$-$U^{rp}$-T-$T^{t}$-H (SEQ ID NO: 19 of the Sequence Listing) (Sense Strand of HS-001)

The sense strand of HS-001 was synthesized in the same way as for Reference Example 32. The structure of the sense strand of HS-001 is shown in FIG. 16.

Molecular weight: calculated value: 6710.12, measured value: 6710.37

Nucleotide sequence: comprising a sequence of nucleotide Nos. 1601-1619 of the heat shock protein 47 gene (GenBank accession No. NM_001235)

Reference Example 39

Synthesis of HO-$A^{rp}$-$U^{rp}$-$A^{rp}$-$G^{rp}$-$C^{rp}$-$A^{rp}$-$C^{rp}$-$C^{rp}$-$C^{rp}$-$A^{rp}$-$U^{rp}$-$G^{rp}$-$U^{rp}$-$G^{rp}$-$U^{rp}$-$C^{rp}$-$U^{rp}$-$C^{rp}$-$A^{rp}$-$T^{p}$-$T^{t}$-H (SEQ ID NO: 20 of the Sequence Listing) (Antisense Strand of HS-001)

The sense strand of HS-001 was synthesized in the same way as for Reference Example 32. The structure of the antisense strand of HS-001 is shown in FIG. 16. Molecular weight: calculated value: 6590.04, measured value: 6589.88

Nucleotide sequence: comprising a sequence complementary to nucleotide Nos. 1601-1619 of the heat shock protein 47 gene (GenBank accession No. NM_001235)

Reference Example 40

Synthesis of HO-$G^{rp}$-$A^{rp}$-$G^{rp}$-$A^{rp}$-$C^{rp}$-$A^{rp}$-$C^{rp}$-$A^{rp}$-$U^{rp}$-$G^{rp}$-$G^{rp}$-$G^{rp}$-$U^{rp}$-$G^{rp}$-$C^{rp}$-$U^{rp}$-$U^{rp}$-$U^{rp}$-$A^{rp}$-$T^{p}$-$T^{t}$-H (SEQ ID NO: 21 of the Sequence Listing) (sense strand of HS-002)

The sense strand of HS-002 was synthesized in the same way as for Reference Example 32. The structure of the sense strand of HS-002 is shown in FIG. 16.

Molecular weight: calculated value: 6733.16, measured value: 6733.22

Nucleotide sequence: comprising a sequence of nucleotide Nos. 1602-1619 of the heat shock protein 47 gene (GenBank accession No. NM_001235)

Reference Example 41

Synthesis of HO—$U^{rp}$-$A^{rp}$-$U^{rp}$-$A^{rp}$-$G^{rp}$-$C^{rp}$-$A^{rp}$-$C^{rp}$-$C^{rp}$-$A^{rp}$-$U^{rp}$-$G^{rp}$-$U^{rp}$-$G^{rp}$-$U^{rp}$-$C^{rp}$-$U^{rp}$-$C^{rp}$-$T^{p}$-$T^{t}$-H (SEQ ID NO: 22 of the Sequence Listing) (Antisense Strand of HS-002)

The sense strand of HS-002 was synthesized in the same way as for Reference Example 32. The structure of the antisense strand of HS-002 is shown in FIG. 16.

Molecular weight: calculated value: 6567.00, measured value: 6566.99

Nucleotide sequence: comprising a sequence complementary to nucleotide Nos. 1602-1619 of the heat shock protein 47 gene (GenBank accession No. NM_001235)

Test Example 4

A method for determining the mouse PKR (Eif2ak2) gene expression inhibitory activities of single-stranded and double-stranded polynucleotides will now be explained.

The single-stranded and double-stranded polynucleotides described in FIG. 15 can separately be introduced to mouse embryonic fibroblasts using a lipofection reagent Lipofectamine RNAiMAX (manufactured by Invitrogen Corp.).

24 to 48 hours after the transfection, total RNA is extracted from each cell using RNeasy Mini kit (manufactured by QIAGEN). The mRNA is reverse-transcribed into cDNA using SuperScript III First-Strand Synthesis Super Mix for qRT-PCR (manufactured by Invitrogen Corp.). The expression levels of the PKR gene and an internal standard 36B4 gene are measured with a quantitative PCR system (Applied Biosystems) using SYBR Green. Primers 5'-AAAACAAG-GTGGATTGTCACACG-3' and 5'-GTTGGGCTCACACT-GTTCATAAT-3' for PKR and 5'-CACTGGTCTAGGAC-CCGAGAA-3' and 5'-AGGGGGAGATGTTCAGCATGT-3' for 36B4 are used according to the reference (Nakamura T, et al., Cell, 140, 338-348 (2010)). The PKR mRNA level of each sample can be divided by the 36B4 mRNA level of this sample for correction to thereby determine the relative intensity of gene silencing by each single-stranded or double-stranded polynucleotide.

Test Example 5

Rat Hsp47 (Serpinh1) gene expression inhibitory activities of single-stranded and double-stranded polynucleotides were determined as follows:
(1) Transfection
200 μL of an OPTI-MEM medium (manufactured by Invitrogen Corp) and a single-stranded or double-stranded polynucleotide solution (final concentration: 1 and 0.1 nM) were added to each well of a 12-well flat-bottomed plate (manufactured by Sumitomo Bakelite Co., Ltd.). AllStars Negative Control siRNA purchased from Qiagen was used as a negative control. 1.2 µL of a lipofection reagent Lipofectamine RNAiMAX (manufactured by Invitrogen Corp.) was added and mixed into each well, and the mixture was left standing at room temperature for 10 to 20 minutes. Meanwhile, a rat NRK-52E cell strain was adjusted to a concentration of 62500 cells/mL in a Dulbecco's modified Eagle's medium (manufactured by Invitrogen Corp.) containing 10% fetal bovine serum. Then, the cells were seeded at a concentration of 1 mL/well onto the plate containing the diluted lipofection reagent-polynucleotide solution and cultured at 37° C. under 5.0% $CO_2$ conditions.

(2) Real-Time PCR 27 hours after the transfection, total RNA was extracted from each cell using RNeasy Mini kit (manufactured by QIAGEN). After reverse transcription into cDNA using SuperScript III First-Strand Synthesis Super Mix for qRT-PCR (manufactured by Invitrogen Corp.), the Hsp47 mRNA level was measured by quantitative PCR using a TaqMan probe. Primers and a probe included in the TaqMan Gene Expression Assay (manufactured by Applied Biosystems, Assay ID Rn00567777 ml) were used for the Hsp47 gene. The TaqMan reaction was performed using ABI Prism 7900HT Sequence detection system (manufactured by Applied Biosystems). The ribosomal RNA (rRNA) expression level of the same sample was measured as an internal standard. TaqMan Ribosomal RNA Control Reagents VIC™ Probe (manufactured by Applied Biosystems, catalog No: 4308329) was used as primers and a probe for the rRNA assay.

Figure 17:
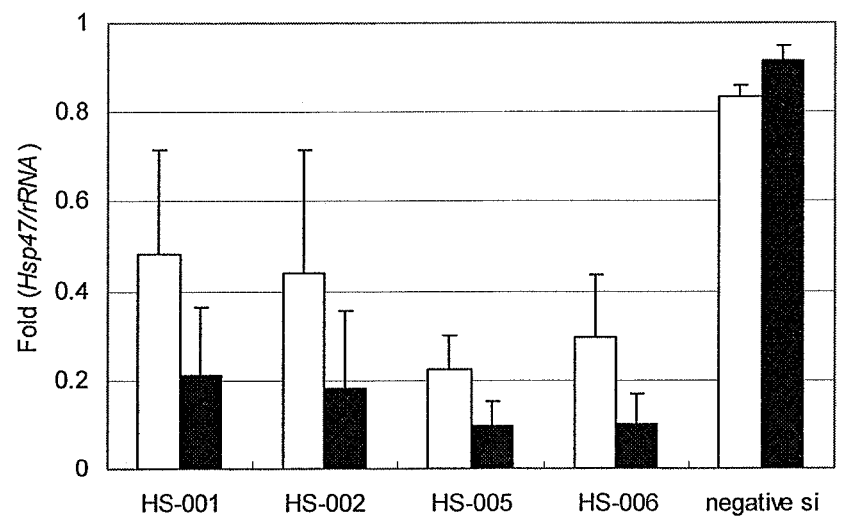
FIG. 17 is a diagram showing the gene inhibitory activities of polynucleotides analyzed by real-time PCR. The open bar represents a polynucleotide concentration of 0.1 nM. The filled bar represents a polynucleotide concentration of 1 nM. The same holds true for FIGS. 18 and 20.

The Hsp47 mRNA level of each sample was divided by the rRNA level of this sample. A relative value was plotted on FIG. 17 with the value of the cell supplemented with only a transfection reagent and with no polynucleotide as 1 (in the diagram, negative si was indicated when AllStars Negative Control siRNA (catalog No: 1027280) was used). FIG. 17 shows a mean of results of three independent experiments and its S.D. value (the structure and nucleotide sequence of each polynucleotide is shown in FIG. 16).

(2) Real-Time PCR Analysis (a) Gene Inhibitory Activity Analysis—1—

The double-stranded polynucleotide HS-001, the double-stranded polynucleotide HS-002, the single-stranded polynucleotide HS-005, and the single-stranded polynucleotide HS-006 (for their structures, see FIG. 16) were examined for their rat Hsp47 gene expression inhibitory activities.

As shown in FIG. 17, HS-005 more strongly inhibited the expression of the rat Hsp47 gene than HS-001. HS-006 more strongly inhibited the expression of the rat Hsp47 gene than HS-002. In this test, AllStars Negative Control siRNA exhibited no Hsp47 gene inhibitory activity. This shows that a single-stranded polynucleotide in which the 5'-end of the antisense strand and the 3'-end of the sense strand are linked via phosphate groups using a modified phenyl group has stronger gene expression inhibitory activity than that of a double-stranded polynucleotide.

Test Example 6

The rat Hsp47 (Serpinh1) gene expression inhibitory activities of single-stranded and double-stranded polynucleotides were determined.

(1) Transfection

Transfection was performed in the same way as for Test Example 5 using the double-stranded polynucleotides HS-001 and HS-002 and the single-stranded polynucleotides HS-005s and HS-006s (for their structures, see FIG. 16). However, each nucleic acid was introduced, in half the amount as in Test Example 5, into NRK-52E cells in a system using a 24-well flat-bottomed plate (manufactured by Sumitomo Bakelite Co., Ltd.).

(2) Real-Time PCR

Real-time PCR was performed in the same way as for Test Example 5.

(a) Gene Inhibitory Activity Analysis—1—

The double-stranded polynucleotides HS-001 and HS-002 and the single-stranded polynucleotides HS-005s and HS-006s were examined for their rat Hsp47 gene expression inhibitory activities.

Figure 18:
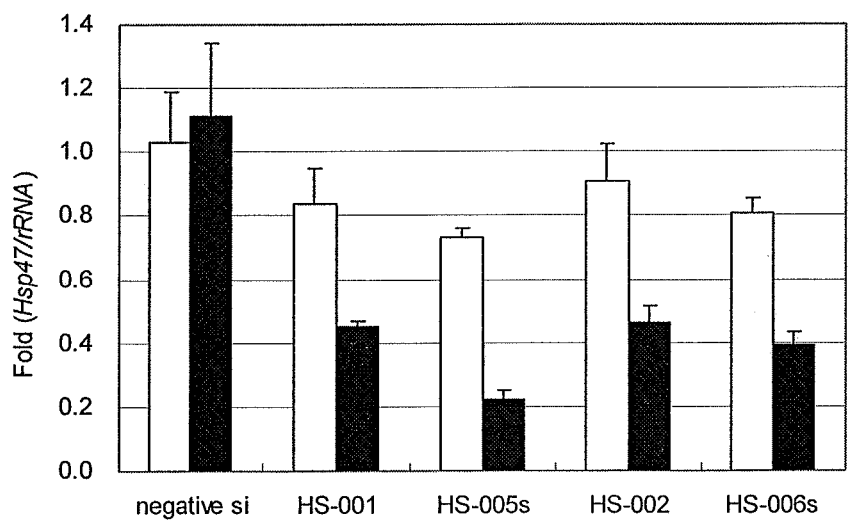
FIG. 18 is a diagram showing the gene inhibitory activities of polynucleotides analyzed by real-time PCR.

As shown in FIG. 18, HS-005s and HS-006s strongly inhibited the expression of the rat Hsp47 gene at a level equivalent to or higher than HS-001 and HS-002. This shows that a single-stranded polynucleotide in which the 5'-end of the antisense strand and the 3'-end of the sense strand are linked via phosphate groups using a modified phenyl group has a stronger gene expression inhibitory activity than that of a double-stranded polynucleotide.

Test Example 7

The rat Hsp47 (Serpinh1) gene expression inhibitory activities of single-stranded and double-stranded polynucleotides were determined.

(1) Transfection

Transfection was performed in the same way as for Test Example 6 using a double-stranded polynucleotide siHSP47C (SEQ ID NOs: 31 and 32 of the Sequence Listing; for its structure, see FIG. 19) described in International Publication No. WO 2011/072082 and the single-stranded polynucleotide HS-012 (for its structure, see FIG. 19). siHSP47C sense strand: 5'-GGACAGGCCUCUACAACUATT-3' (SEQ ID NO: 31)

siHSP47C antisense strand: 5'-UAGUUGUAGAGGCCU-GUCCTT-3' (SEQ ID NO: 32)

(2) Real-Time PCR

Real-time PCR was performed in the same way as for Test Example 5.

(a) Gene Inhibitory Activity Analysis—1—

The double-stranded polynucleotide siHSP47C and the single-stranded polynucleotide HS-012 were examined for their rat Hsp47 gene expression inhibitory activities.

Figure 20:
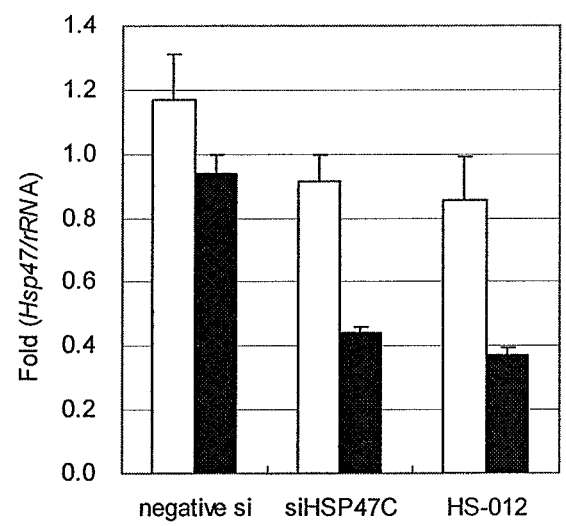
FIG. 20 is a diagram showing the gene inhibitory activities of polynucleotides analyzed by real-time PCR.

As shown in FIG. 20, HS-012 strongly inhibited the expression of the rat Hsp47 gene at a level equivalent to or higher than siHSP47C. This shows that a single-stranded polynucleotide in which the 5'-end of the antisense strand and the 3'-end of the sense strand are linked via phosphate groups using a modified phenyl group has a stronger gene expression inhibitory activity than that of a double-stranded polynucleotide.

INDUSTRIAL APPLICABILITY

The present invention could provide a single-stranded polynucleotide that has an RNA interference effect and/or a gene expression inhibitory effect. The present invention could also provide a single-stranded polynucleotide that is resistant to RNase and has an RNA interference effect and/or a gene expression inhibitory effect.

The single-stranded polynucleotide can be used in the functional analysis of genes, pharmaceutical compositions, etc. However, the industrial field of the present single-stranded polynucleotide is not limited as long as it can be used therein.

FREE TEXT OF SEQUENCE LISTING

SEQ ID NO: 1: CT-169
SEQ ID NO: 2: CT-157
SEQ ID NO: 3: Sense strand region of CT-472
SEQ ID NO: 4: Antisense strand region of CT-472
SEQ ID NO: 5: Sense strand region of CT-473
SEQ ID NO: 6: Antisense strand region of CT-473
SEQ ID NO: 7: CT-106
SEQ ID NO: 8: CT-041
SEQ ID NO: 9: CT-001
SEQ ID NO: 10: CT-005
SEQ ID NO: 11: β-catenin gene forward primer
SEQ ID NO: 12: β-catenin gene reverse primer
SEQ ID NO: 13: GAPDH gene forward primer
SEQ ID NO: 14: GAPDH gene reverse primer
SEQ ID NO: 15: PK-001
SEQ ID NO: 16: PK-002
SEQ ID NO: 17: Sense strand region of PK-009
SEQ ID NO: 18: Antisense strand region of PK-009
SEQ ID NO: 19: Sense strand of HS-001
SEQ ID NO: 20: Antisense strand of HS-001
SEQ ID NO: 21: Sense strand of HS-002
SEQ ID NO: 22: Antisense strand of HS-002
SEQ ID NO: 23: Sense strand region of HS-005
SEQ ID NO: 24: Antisense strand region of HS-005
SEQ ID NO: 25: Sense strand region HS-006
SEQ ID NO: 26: Antisense strand region of HS-006
SEQ ID NO: 27: Sense strand region of HS-005s
SEQ ID NO: 28: Antisense strand region of HS-005s
SEQ ID NO: 29: Sense strand region of HS-006s
SEQ ID NO: 30: Antisense strand region of HS-006s
SEQ ID NO: 31: Sense strand of siHSP47C
SEQ ID NO: 32: Antisense strand of siHSP47C
SEQ ID NO: 33: Sense strand region of HS-012
SEQ ID NO: 34: Antisense strand region of HS-012

The invention claimed is:

1. A polynucleotide or a salt thereof, the polynucleotide comprising:
   a sense strand polynucleotide corresponding to a target gene, and
   an antisense strand polynucleotide having a nucleotide sequence complementary to the sense strand polynucleotide and having a structure represented by the following formula:

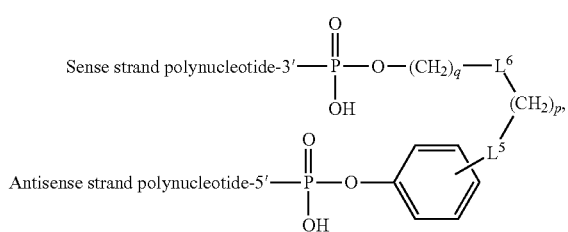

wherein
the 5'-end of the antisense strand polynucleotide and the 3'-end of the sense strand polynucleotide are linked via a linker through phosphodiester bonds,
p is an integer of 0 to 4,
q is an integer of 4 to 10,
$L^5$ is a single bond or —O—,
$L^6$ is —(C=O)—NH— or —NH—(C=O)—, wherein —(C=O)—NH— and —NH—(C=O)— are written starting from the bond with $(CH_2)_p$, and
$L^5$ is bonded to the benzene ring at the para or meta position,
provided that if $L^5$ is —O—, then p represents an integer of 1 to 4.

2. The polynucleotide or a salt thereof of claim 1, wherein the sum of p and q is an integer of 4 or larger, $L^5$ is a single bond, $L^6$ is —(C=O)—NH—, and $L^5$ is bonded to the benzene ring at the para position.

3. The polynucleotide or a salt thereof of claim 1, wherein the sum of p and q is an integer of 8 or larger, $L^5$ is a single bond, $L^6$ is —(C=O)—NH—, and $L^5$ is bonded to the benzene ring at the para position.

4. The polynucleotide or a salt thereof of claim 1, wherein p is 0 or 2, q is an integer of 6 or larger, $L^5$ is a single bond, $L^6$ is —(C=O)—NH—, and $L^5$ is bonded to the benzene ring at the para position.

5. The polynucleotide or a salt thereof of claim 1, wherein p is 0 or 2, q is 6 or 8, $L^5$ is a single bond, $L^6$ is —(C=O)—NH—, and $L^5$ is bonded to the benzene ring at the para position.

6. The polynucleotide or a salt thereof of claim 1, wherein p is 0 or 2, q is 8, $L^5$ is a single bond, $L^6$ is —(C=O)—NH—, and $L^5$ is bonded to the benzene ring at the para position.

7. The polynucleotide or a salt thereof of claim 1, wherein p is 2, q is 8, $L^5$ is a single bond, $L^6$ is —(C=O)—NH—, and $L^5$ is bonded to the benzene ring at the para position.

8. A method for producing a compound represented by the following formula (XI):

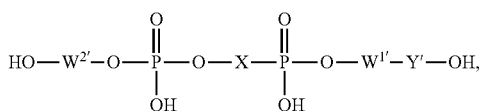
(XI)

wherein
the compound is a polynucleotide comprising a sense strand polynucleotide corresponding to a target gene, and an antisense strand polynucleotide having a nucleotide sequence complementary to the sense strand polynucleotide, wherein the 5'-end of the antisense strand polynucleotide and the 3'-end of the sense strand polynucleotide are linked via X through phosphodiester bonds;
$W^{2'}$ is a sense strand polynucleotide without 5'-terminal and 3'-terminal hydroxy groups;
$W^{1'}$-$Y'$ is an antisense strand polynucleotide without 5'-terminal and 3'-terminal hydroxy groups; and
X is the formula (XII):

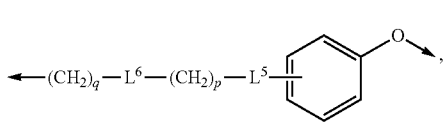
(XII)

wherein
p is an integer of 0 to 4;
q is an integer of 4 to 10;
$L^5$ is a single bond or —O—;
$L^6$ is —(C=O)—NH— or —NH—(C=O)—, wherein —(C=O)—NH— and —NH—(C=O)— are written starting from the bond with $(CH_2)_p$;
$L^5$ is bonded to the benzene ring at the para or meta position;
provided that if $L^5$ is —O—, then p is an integer of 1 to 4;
the terminal methylene group is bound to the 3'-end of the sense strand polynucleotide to form a phosphodiester bond; and
the oxygen atom bonded to the phenyl group is bound to the 5'-end of the antisense strand polynucleotide to form a phosphodiester bond;
the method comprising the steps of:
(i) reacting the hydroxy group of a compound represented by the formula Tr-O—X—H, wherein Tr is a protective group for the hydroxy group, —$(CH_2)_q$— in X is bonded to Tr-O— and the oxygen atom bonded to the phenyl group is bonded to hydrogen,
with a compound represented by the formula (XIII):

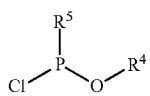
(XIII)

or the formula (XIV):

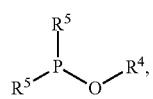
(XIV)

wherein $R^4$ is a 2-cyanoethyl group, a methyl group, a methanesulfonylethyl group, a 2,2,2-trichloroethyl group, or a 4-chlorophenylmethyl group, and $R^5$ is a morpholino group, a diisopropylamino group, a diethylamino group, or a dimethylamino group,
to produce a compound represented by the formula (XV):

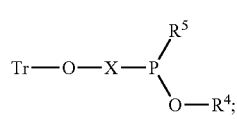
(XV)

(ii) reacting the compound obtained in step (i) with a compound represented by the formula HO—W'—Y-CPG, wherein W'—Y is a protected antisense strand polynucleotide without 5'-terminal and 3'-terminal hydroxy groups, and CPG represents a polymer support having a linker capable of binding to the polynucleotide,
by a phosphoramidite method and subsequently producing a moiety represented by the formula $Tr^1$-O—$W^2$—O—P(=O)($OR^4$)—O—, wherein $Tr^1$ is a protective group for the hydroxy group, and $W^2$ represents a protected sense strand polynucleotide without 5'-terminal and 3'-terminal hydroxy groups,
by a phosphoramidite method to produce a compound represented by the formula (XVI):

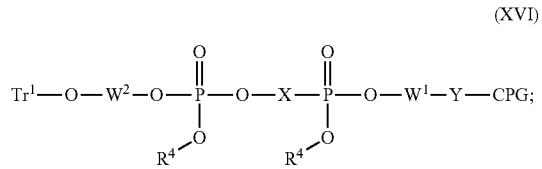
(XVI)

and
(iii) excising the compound obtained in step (ii) from CPG and removing the protective group.

9. The method of claim 8, wherein Tr and $Tr^1$ are the same or different and are a 4-methoxytrityl group, a 4,4'-dimethoxytrityl group, a pixyl group, a trityl group, a levulinyl group, or a bis(trimethylsilyloxy)(cyclohexyloxy)silyl group.

10. The method of claim 8, wherein Tr and $Tr^1$ are the same or different and are a 4-methoxytrityl group or a 4,4'-dimethoxytrityl group, the sum of p and q is an integer of 4 or larger, $L^5$ is a single bond, $L^6$ is —(C=O)—NH—, and $L^5$ is bonded to the benzene ring at the para position.

11. The method of claim 8, wherein Tr and $Tr^1$ are the same or different and are a 4-methoxytrityl group or a 4,4'-dimethoxytrityl group, the sum of p and q is an integer of 8 or larger, $L^5$ is a single bond, $L^6$ is —(C=O)—NH—, and $L^5$ is bonded to the benzene ring at the para position.

12. The method of claim 8, wherein Tr and $Tr^1$ are the same or different and are a 4-methoxytrityl group or a 4,4'-dimethoxytrityl group, p is 0 or 2, q is an integer of 6 or larger, $L^5$ is a single bond, $L^6$ is —(C=O)—NH—, and $L^5$ is bonded to the benzene ring at the para position.

13. The method of claim 8, wherein Tr and Tr$^1$ are the same or different and are a 4-methoxytrityl group or a 4,4'-dimethoxytrityl group, p is 0 or 2, q is 6 or 8, L$^5$ is a single bond, L$^6$ is —(C=O)—NH—, and L$^5$ is bonded to the benzene ring at the para position.

14. The method of claim 8, wherein Tr and Tr$^1$ are the same or different and are a 4-methoxytrityl group or a 4,4'-dimethoxytrityl group, p is 0 or 2, q is 8, L$^5$ is a single bond, L$^6$ is —(C=O)—NH—, and L$^5$ is bonded to the benzene ring at the para position.

15. The method of claim 8, wherein Tr and Tr$^1$ are the same or different and are a 4-methoxytrityl group or a 4,4'-dimethoxytrityl group, p is 2, q is 8, L$^5$ is a single bond, L$^6$ is —(C=O)—NH—, and L$^5$ is bonded to the benzene ring at the para position.

16. The method of claim 8, wherein each of Tr and Tr$^1$ is a 4,4'-dimethoxytrityl group, p is 2, q is 8, L$^5$ is a single bond, L$^6$ is —(C=O)—NH—, and L$^5$ is bonded to the benzene ring at the para position.

17. The method of claim 8, wherein R$^4$ is a 2-cyanoethyl group or a methyl group, and R$^5$ is a morpholino group or a diisopropylamino group.

18. The method of claim 8, wherein the compound represented by the formula (XIII) is chloro(morpholino)methoxyphosphine, chloro(morpholino)cyanoethoxyphosphine, chloro(diisopropylamino)methoxyphosphine, or chloro(diisopropylamino)cyanoethoxyphosphine.

19. The method of claim 8, wherein the compound represented by the formula (XIV) is bis(diisopropylamino)cyanoethoxyphosphine.

20. A polynucleotide selected from the following:

HO—C$^p$-G$^{m1p}$-A$^p$-G$^{m1p}$-A$^p$-C$^{m1p}$-A$^p$-C$^{m1p}$-A$^p$-U$^{m1p}$-G$^p$-G$^{m1p}$-G$^p$-U$^{m1p}$-G$^p$-C$^{m1p}$-T$^p$-A$^{m1p}$-X—P(=O)(OH)—O-U$^{m1p}$-T$^p$-A$^{m1p}$-G$^p$-C$^{m1p}$-A$^p$-C$^{m1p}$-C$^p$-C$^{m1p}$-A$^p$-U$^{m1p}$-G$^p$-U$^{m1p}$-G$^p$-U$^{m1p}$-C$^p$-U$^{m1p}$-C$^p$-G$^{m1p}$-T$^p$-U$^{m1t}$-H (HS-005) (SEQ ID NO: 23 linked to SEQ ID NO: 24 by —X—P(=O)(OH)—O—), HO—C$^p$-A$^{m1p}$-G$^p$-A$^{m1p}$-C$^p$-A$^{m1p}$-C$^p$-A$^{m1p}$-T$^p$-G$^{m1p}$-G$^p$-G$^{m1p}$-T$^p$-G$^{m1p}$-C$^p$-U$^{m1p}$-A$^p$-U$^{m1p}$-X—P(=O)(OH)—O-U$^{m1p}$-A$^p$-U$^{m1p}$-A$^p$-G$^{m1p}$-C$^p$-A$^{m1p}$-C$^p$-C$^{m1p}$-C$^p$-A$^{m1p}$-T$^p$-G$^{m1p}$-T$^p$-G$^{m1p}$-T$^p$-C$^{m1p}$-T$^p$-G$^{m1p}$-T$^p$-U$^{m1t}$-H (HS-006) (SEQ ID NO: 25 linked to SEQ ID NO: 26 by —X—P(=O)(OH)—O—), HO—C$^p$-G$^{m1p}$-A$^p$-G$^{m1p}$-A$^p$-C$^{m1p}$-A$^p$-C$^{m1p}$-A$^p$-U$^{m1p}$-G$^p$-G$^{m1p}$-G$^p$-U$^{m1p}$-G$^p$-C$^{m1p}$-T$^p$-A$^{m1p}$-X—P(=O)(OH)—O-U$^{m1p}$-T$^p$-A$^{m1p}$-G$^p$-C$^{m1p}$-A$^p$-C$^{m1p}$-C$^p$-C$^{m1p}$-A$^p$-U$^{m1p}$-G$^p$-U$^{m1p}$-G$^p$-U$^{m1p}$-C$^p$-U$^{m1p}$-C$^p$-G$^{m1p}$-T$^s$-U$^{m1t}$-H (HS-005s) (SEQ ID NO: 27 linked to SEQ ID NO: 28 by —X—P(=O)(OH)—O—), or HO—C$^p$-A$^{m1p}$-G$^p$-A$^{m1p}$-C$^p$-A$^{m1p}$-C$^p$-A$^{m1p}$-T$_p$-G$^{m1p}$-G$^p$-G$^{m1p}$-T$^p$-G$^{m1p}$-C$^p$-U$^{m1p}$-A$^p$-U$^{m1p}$-X—P(=O)(OH)—O—U$^{m1p}$-A$^p$-U$^{m1p}$-A$^p$-G$^{m1p}$-C$^p$-A$^{m1p}$-C$^p$-C$^{m1p}$-C$^p$-A$^{m1p}$-T$^p$-G$^{m1p}$-T$^p$-G$^{m1p}$-T$^p$-C$^{m1p}$-T$^p$-G$^{m1p}$-T$^s$-U$^{m1t}$-H (HS-006s) (SEQ ID NO: 29 linked to SEQ ID NO: 30 by —X—P(=O)(OH)—O—), or a salt thereof, wherein each of A$^p$, G$^p$, C$^p$, T$^p$, T$^s$, A$^{m1p}$, G$^{m1p}$, C$^{m1p}$, U$^{m1p}$, and U$^{m1t}$ is a nucleoside or a nucleotide having a structure represented by the following formulas:

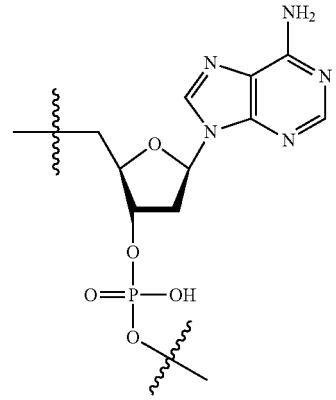

A$^p$

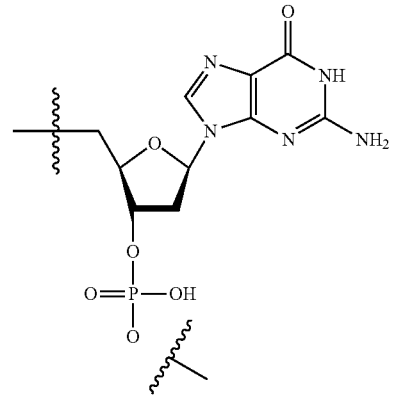

G$^p$

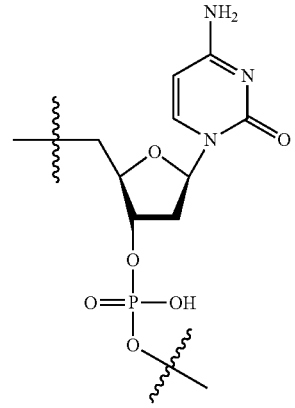

C$^p$

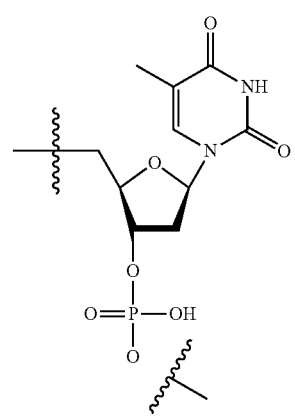

T$^p$

-continued $T^s$
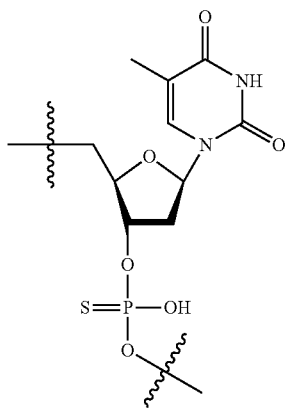

$A^{m1p}$
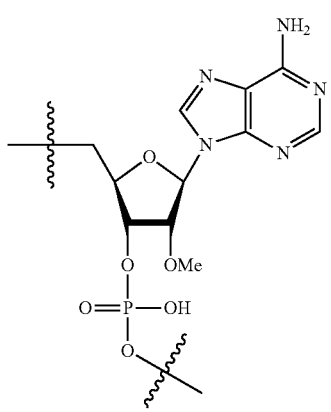

$G^{m1p}$
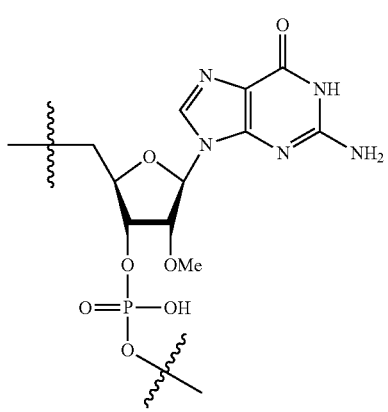

$C^{m1p}$
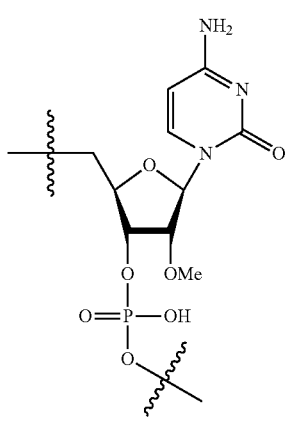

-continued $U^{m1p}$
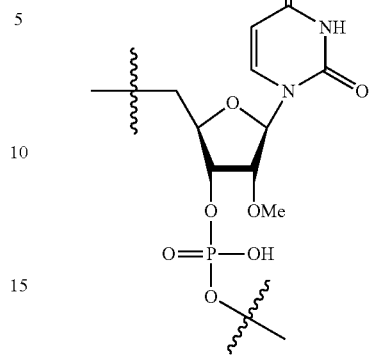

$U^{m1t}$
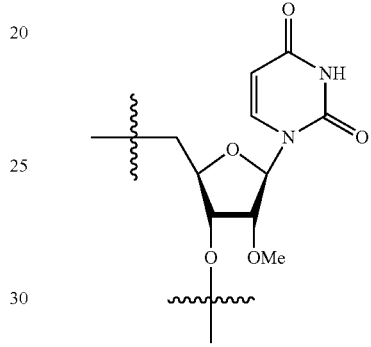

the sequence upstream from X is a sense strand polynucleotide corresponding to a target gene;

the sequence downstream from X is a polynucleotide having an antisense strand polynucleotide having a nucleotide sequence complementary to the sense strand polynucleotide;

X is a linker having a structure represented by the formula (XVII):

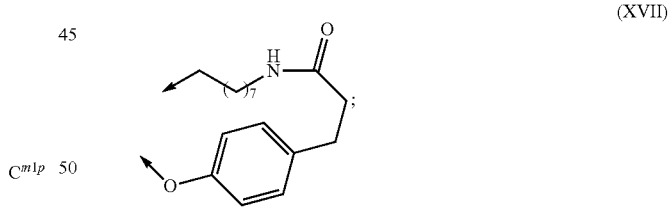

(XVII)

the terminal methylene group is bound to the 3'-end of the sense strand polynucleotide to form a phosphodiester bond; and the oxygen atom bonded to the phenyl group is bound to the 5'-end of the antisense strand polynucleotide to form a phosphodiester bond.

21. A pharmaceutical composition comprising a polynucleotide or a salt thereof of claim 20 and a pharmaceutically acceptable carrier.

22. A method of inhibiting the expression of the Hsp47 gene, comprising administering a polynucleotide or a salt thereof of claim 20 to a mammal.

* * * * *

UNITED STATES PATENT AND TRADEMARK OFFICE
CERTIFICATE OF CORRECTION

PATENT NO. : 8,987,226 B2
APPLICATION NO. : 13/991209
DATED : March 24, 2015
INVENTOR(S) : Koizumi et al.

Page 1 of 2

It is certified that error appears in the above-identified patent and that said Letters Patent is hereby corrected as shown below:

In the Claims

Claim 8, column 124, lines 24-25, delete "pound represented by the formula HO-W'-Y-CPG, wherein W'-Y is a protected antisense strand poly-" and insert therefor -- pound represented by the formula HO-W$^1$-Y-CPG, wherein W$^1$-Y is a protected antisense strand poly- --.

Claim 20, column 125, line 56, delete "HO-C$^p$-A$^{m1p}$-G$^p$-A$^{m1p}$-C$^p$-A$^{m1p}$-C$^p$-A$^{m1p}$-T$_p$-G$^{m1p}$-G$^p$-" and insert therefor -- HO-C$^p$-A$^{m1p}$-G$^p$-A$^{m1p}$-C$^p$-A$^{m1p}$-C$^p$-A$^{m1p}$-T$^p$-G$^{m1p}$-G$^p$ --.

Claim 20, column 126, delete formula G$^p$:

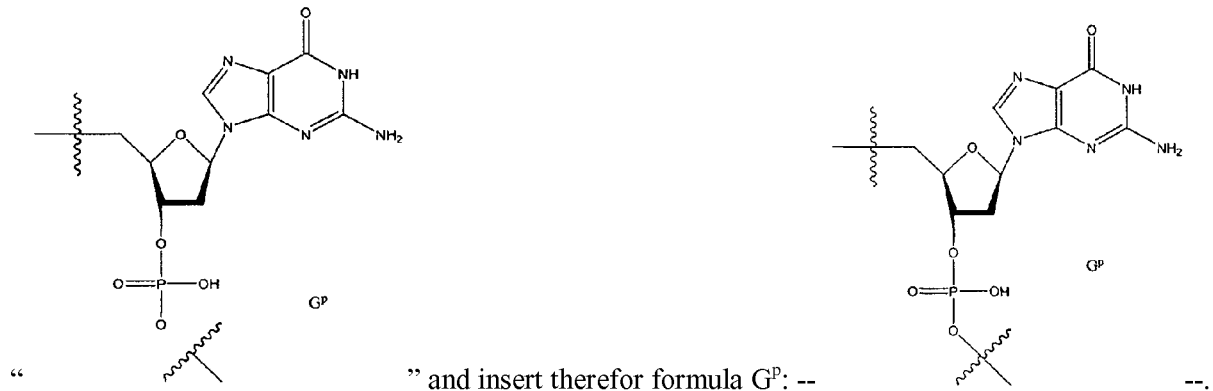

Signed and Sealed this
Eighth Day of September, 2015

Michelle K. Lee
*Director of the United States Patent and Trademark Office*

CERTIFICATE OF CORRECTION (continued)
U.S. Pat. No. 8,987,226 B2

Claim 20, column 126, delete formula $T^p$:

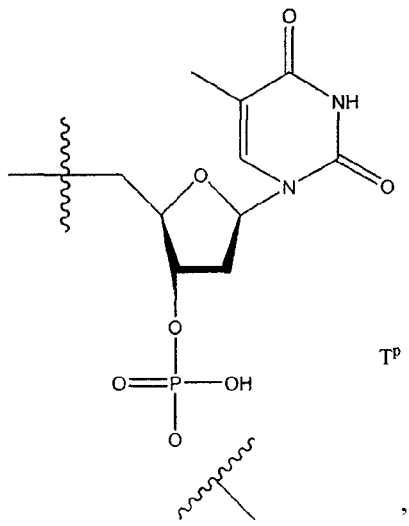

" and insert therefor formula $T^p$:

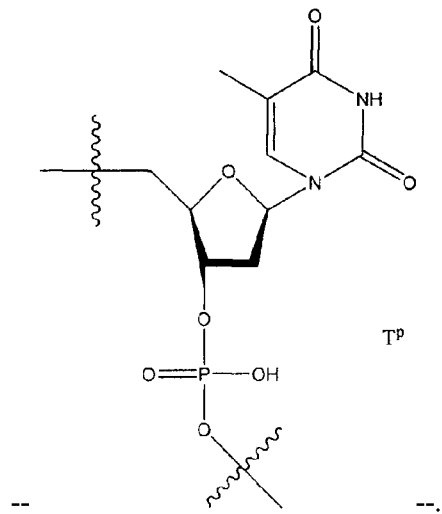

--.

```
                        SEQUENCE LISTING

<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: sense strand
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 1
gcacaagaau ggaucaca                                                18

<210> SEQ ID NO 2
<211> LENGTH: 21
```

```
<212> TYPE: DNA
<213> ORGANISM: Artificial Sequence
<220> FEATURE:
<223> OTHER INFORMATION: antisense strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 2
utgtgaucca utctugugct u                                              21

<210> SEQ ID NO 3
<211> LENGTH: 21
<212> TYPE: RNA
<213> ORGANISM: Artificial Sequence
<220> FEATURE:
<223> OTHER INFORMATION: sense strand region of CT-472

<400> SEQUENCE: 3
gcacaagaau ggaucacaau u                                              21

<210> SEQ ID NO 4
<211> LENGTH: 21
<212> TYPE: RNA
<213> ORGANISM: Artificial Sequence
<220> FEATURE:
<223> OTHER INFORMATION: antisense strand region of CT-472

<400> SEQUENCE: 4
uugugaucca uucuugugcu u                                              21

<210> SEQ ID NO 5
```

```
<211> LENGTH: 19
<212> TYPE: DNA
<213> ORGANISM: Artificial Sequence
<220> FEATURE:
<223> OTHER INFORMATION: sense strand region of CT-473
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 5
gcacaagaau ggaucacaa                                                  19

<210> SEQ ID NO 6
<211> LENGTH: 21
<212> TYPE: DNA
<213> ORGANISM: Artificial Sequence
<220> FEATURE:
<223> OTHER INFORMATION: antisense strand region of CT-473
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
```

```
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 6
uugugaucca uucuugugcu u                                           21

<210> SEQ ID NO 7
<211> LENGTH: 21
<212> TYPE: RNA
<213> ORGANISM: Artificial Sequence
<220> FEATURE:
<223> OTHER INFORMATION: CT-106

<400> SEQUENCE: 7
gcacaagaau ggaucacaau u                                           21

<210> SEQ ID NO 8
<211> LENGTH: 21
<212> TYPE: RNA
<213> ORGANISM: Artificial Sequence
<220> FEATURE:
<223> OTHER INFORMATION: CT-041

<400> SEQUENCE: 8
uugugaucca uucuugugcu u                                           21

<210> SEQ ID NO 9
<211> LENGTH: 21
<212> TYPE: DNA
<213> ORGANISM: Artificial Sequence
<220> FEATURE:
<223> OTHER INFORMATION: CT-001
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
```

```
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 9
gcacaagaau ggaucacaat t                                              21

<210> SEQ ID NO 10
<211> LENGTH: 21
<212> TYPE: DNA
<213> ORGANISM: Artificial Sequence
<220> FEATURE:
<223> OTHER INFORMATION: CT-005
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 10
uugugaucca uucuugugct t                                              21

<210> SEQ ID NO 11
<211> LENGTH: 25
<212> TYPE: DNA
<213> ORGANISM: Artificial
<220> FEATURE:
<223> OTHER INFORMATION: beta-catenin forward primer

<400> SEQUENCE: 11
tctgaggaca agccacaaga ttaca                                          25

<210> SEQ ID NO 12
<211> LENGTH: 22
```

```
<212> TYPE: DNA
<213> ORGANISM: Artificial
<220> FEATURE:
<223> OTHER INFORMATION: beta-catenin reverse primer

<400> SEQUENCE: 12
tgggcaccaa tatcaagtcc aa                                              22

<210> SEQ ID NO 13
<211> LENGTH: 20
<212> TYPE: DNA
<213> ORGANISM: Artificial
<220> FEATURE:
<223> OTHER INFORMATION: GAPDH forward primer

<400> SEQUENCE: 13
gcaccgtcaa ggctgagaac                                                 20

<210> SEQ ID NO 14
<211> LENGTH: 19
<212> TYPE: DNA
<213> ORGANISM: Artificial
<220> FEATURE:
<223> OTHER INFORMATION: GAPDH reverse primer

<400> SEQUENCE: 14
tggtgaagac gccagtgga                                                  19

<210> SEQ ID NO 15
<211> LENGTH: 21
<212> TYPE: RNA
<213> ORGANISM: Artificial Sequence
<220> FEATURE:
<223> OTHER INFORMATION: PK-001

<400> SEQUENCE: 15
gcucgucuau gacaaguaau u                                               21

<210> SEQ ID NO 16
<211> LENGTH: 21
<212> TYPE: RNA
<213> ORGANISM: Artificial Sequence
<220> FEATURE:
<223> OTHER INFORMATION: PK-002

<400> SEQUENCE: 16
uuacuuguca uagacgagcu g                                               21

<210> SEQ ID NO 17
<211> LENGTH: 18
<212> TYPE: DNA
<213> ORGANISM: Artificial Sequence
<220> FEATURE:
<223> OTHER INFORMATION: sense strand region of PK-009
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
```

```
<223> OTHER INFORMATION: um
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: 2'-O-methyladenosine

<400> SEQUENCE: 17
gctcgucuau gacaagta                                                 18

<210> SEQ ID NO 18
<211> LENGTH: 21
<212> TYPE: DNA
<213> ORGANISM: Artificial Sequence
<220> FEATURE:
<223> OTHER INFORMATION: antisense strand region of PK-009
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 18
```

-continued utacutgtca uagacgagct u                                             21

<210> SEQ ID NO 19
<211> LENGTH: 21
<212> TYPE: DNA
<213> ORGANISM: Artificial Sequence
<220> FEATURE:
<223> OTHER INFORMATION: sense strand of HS-001

<400> SEQUENCE: 19
ugagacacau gggugcuaut t                                             21

<210> SEQ ID NO 20
<211> LENGTH: 21
<212> TYPE: DNA
<213> ORGANISM: Artificial Sequence
<220> FEATURE:
<223> OTHER INFORMATION: antisense strand of HS-001

<400> SEQUENCE: 20
auagcaccca ugugucucat t                                             21

<210> SEQ ID NO 21
<211> LENGTH: 21
<212> TYPE: DNA
<213> ORGANISM: Artificial Sequence
<220> FEATURE:
<223> OTHER INFORMATION: sense strand of HS-002

<400> SEQUENCE: 21
gagacacaug ggugcuauat t                                             21

<210> SEQ ID NO 22
<211> LENGTH: 21
<212> TYPE: DNA
<213> ORGANISM: Artificial Sequence
<220> FEATURE:
<223> OTHER INFORMATION: antisense strand of HS-002

<400> SEQUENCE: 22
uauagcaccc augugucuct t                                             21

<210> SEQ ID NO 23
<211> LENGTH: 18
<212> TYPE: DNA
<213> ORGANISM: Artificial Sequence
<220> FEATURE:
<223> OTHER INFORMATION: sense strand region of HS-005
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: um
<220> FEATURE:

```
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 23
cgagacacau gggugcta                                                 18

<210> SEQ ID NO 24
<211> LENGTH: 21
<212> TYPE: DNA
<213> ORGANISM: Artificial Sequence
<220> FEATURE:
<223> OTHER INFORMATION: antisense strand region of HS-005
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 24 utagcacccca ugugucucgt u                                            21

<210> SEQ ID NO 25
<211> LENGTH: 18
```

```
<212> TYPE: DNA
<213> ORGANISM: Artificial Sequence
<220> FEATURE:
<223> OTHER INFORMATION: sense strand region of HS-006
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: um

<400> SEQUENCE: 25
cagacacatg ggtgcuau                                              18

<210> SEQ ID NO 26
<211> LENGTH: 21
<212> TYPE: DNA
<213> ORGANISM: Artificial Sequence
<220> FEATURE:
<223> OTHER INFORMATION: antisense strand region of HS-006
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
```

```
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 26
uauagcaccc atgtgtctgt u                                              21

<210> SEQ ID NO 27
<211> LENGTH: 18
<212> TYPE: DNA
<213> ORGANISM: Artificial Sequence
<220> FEATURE:
<223> OTHER INFORMATION: sense strand region of HS-005s
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 27
cgagacacau ggguqcta                                                  18

<210> SEQ ID NO 28
<211> LENGTH: 21
<212> TYPE: DNA
<213> ORGANISM: Artificial Sequence
<220> FEATURE:
<223> OTHER INFORMATION: antisense strand region of HS-005s
<220> FEATURE:
<221> NAME/KEY: modified_base
```

```
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 28
utagcaccca ugugucucgt u                                            21

<210> SEQ ID NO 29
<211> LENGTH: 18
<212> TYPE: DNA
<213> ORGANISM: Artificial Sequence
<220> FEATURE:
<223> OTHER INFORMATION: sense strand region of HS-006s
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (12)..(12)
<223> OTHER INFORMATION: gm
<220> FEATURE:
```

```
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: um

<400> SEQUENCE: 29
cagacacatg ggtgcuau                                                      18

<210> SEQ ID NO 30
<211> LENGTH: 21
<212> TYPE: DNA
<213> ORGANISM: Artificial Sequence
<220> FEATURE:
<223> OTHER INFORMATION: antisense strand region of HS-006s
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 30
uauagcaccc atgtgtctgt u                                                  21

<210> SEQ ID NO 31
<211> LENGTH: 21
<212> TYPE: DNA
<213> ORGANISM: Artificial Sequence
<220> FEATURE:
<223> OTHER INFORMATION: sense strand of siHSP47C
```

-continued

<400> SEQUENCE: 31
ggacaggccu cuacaacuat t         21

<210> SEQ ID NO 32
<211> LENGTH: 21
<212> TYPE: DNA
<213> ORGANISM: Artificial Sequence
<220> FEATURE:
<223> OTHER INFORMATION: antisense strand of siHSP47C

<400> SEQUENCE: 32
uaguuguaga ggccugucct t         21

<210> SEQ ID NO 33
<211> LENGTH: 18
<212> TYPE: DNA
<213> ORGANISM: Artificial Sequence
<220> FEATURE:
<223> OTHER INFORMATION: sense strand region of HS-012
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: um

<400> SEQUENCE: 33
cgacaggccu cuacaacu         18

<210> SEQ ID NO 34
<211> LENGTH: 21
<212> TYPE: DNA
<213> ORGANISM: Artificial Sequence
<220> FEATURE:
<223> OTHER INFORMATION: antisense strand region of HS-012
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)

```
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 34
uagtuguaga ggccugucgt u                                              21
```